(12) United States Patent
Crawford et al.

(10) Patent No.: US 12,161,427 B2
(45) Date of Patent: Dec. 10, 2024

(54) SURGICAL NAVIGATION SYSTEM WITH FLAT PANEL REGISTRATION FIXTURE

(71) Applicant: GLOBUS MEDICAL, INC., Audubon, PA (US)

(72) Inventors: Neil R. Crawford, Chandler, AZ (US); Rand Kmiec, Nashua, NH (US)

(73) Assignee: Globus Medical, Inc., Audubon, PA (US)

( * ) Notice: Subject to any disclaimer, the term of this patent is extended or adjusted under 35 U.S.C. 154(b) by 277 days.

(21) Appl. No.: 17/805,895

(22) Filed: Jun. 8, 2022

(65) Prior Publication Data

US 2023/0397957 A1 Dec. 14, 2023

(51) Int. Cl.

| | |
|---|---|
| *A61B 6/00* | (2024.01) |
| *A61B 34/20* | (2016.01) |
| *A61B 90/00* | (2016.01) |
| *A61B 90/30* | (2016.01) |
| *G06T 7/00* | (2017.01) |
| *G06T 7/38* | (2017.01) |

(52) U.S. Cl.
CPC ............ *A61B 34/20* (2016.02); *A61B 6/5211* (2013.01); *A61B 90/39* (2016.02); *G06T 7/0012* (2013.01); *G06T 7/38* (2017.01); *A61B 2034/2055* (2016.02); *A61B 2034/2065* (2016.02); *A61B 2090/376* (2016.02); *A61B 2090/3966* (2016.02); *A61B 2090/3983* (2016.02); *G06T 2207/10124* (2013.01)

(58) Field of Classification Search
CPC ....... A61B 6/5211; A61B 6/582; A61B 6/583; A61B 6/584; A61B 6/587; A61B 34/20; A61B 34/30; A61B 90/39; A61B 2034/2055; A61B 2034/2065; A61B 2090/363; A61B 2090/376; A61B 2090/3762; A61B 2090/3966; A61B 2090/3983; G06T 7/0012; G06T 7/38; G06T 2207/10124

See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |

(Continued)

FOREIGN PATENT DOCUMENTS

| | | |
|---|---|---|
| EP | 4197478 A1 | 6/2023 |
| JP | 2018051306 A | 4/2018 |

OTHER PUBLICATIONS

US 8,231,638 B2, 07/2012, Swarup et al. (withdrawn)

*Primary Examiner* — Mark R Gaworecki

(57) ABSTRACT

A registration fixture for registration of a medical image to a three-dimensional tracking space, includes a base frame, an orientation plate, and a registration plate. The base frame is adapted to be mounted to an x-ray medical imaging device. The orientation plate is attached to the base frame and has a first set of radiopaque markers arranged along at least four radial lines which extend from a center location. The radial lines are angularly spaced apart about the center location. At least three of the radiopaque markers are arranged along each of the radial lines. The registration plate is attached to the base frame and spaced apart from the orientation plate. The registration plate includes a second set of radiopaque markers arranged along a circle.

20 Claims, 51 Drawing Sheets

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,967,982 A * | 10/1999 | Barnett ............... A61B 34/20 606/130 |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |

(56) References Cited

U.S. PATENT DOCUMENTS

| | | | |
|---|---|---|---|
| 7,726,171 B2 | 6/2010 | Langlotz et al. | |
| 7,742,801 B2 | 6/2010 | Neubauer et al. | |
| 7,751,865 B2 | 7/2010 | Jascob et al. | |
| 7,760,849 B2 | 7/2010 | Zhang | |
| 7,762,825 B2 | 7/2010 | Burbank et al. | |
| 7,763,015 B2 | 7/2010 | Cooper et al. | |
| 7,787,699 B2 | 8/2010 | Mahesh et al. | |
| 7,796,728 B2 | 9/2010 | Bergfjord | |
| 7,813,838 B2 | 10/2010 | Sommer | |
| 7,818,044 B2 | 10/2010 | Dukesherer et al. | |
| 7,819,859 B2 | 10/2010 | Prisco et al. | |
| 7,824,401 B2 | 11/2010 | Manzo et al. | |
| 7,831,294 B2 | 11/2010 | Viswanathan | |
| 7,834,484 B2 | 11/2010 | Sartor | |
| 7,835,557 B2 | 11/2010 | Kendrick et al. | |
| 7,835,778 B2 | 11/2010 | Foley et al. | |
| 7,835,784 B2 | 11/2010 | Mire et al. | |
| 7,840,253 B2 | 11/2010 | Tremblay et al. | |
| 7,840,256 B2 | 11/2010 | Lakin et al. | |
| 7,843,158 B2 | 11/2010 | Prisco | |
| 7,844,320 B2 | 11/2010 | Shahidi | |
| 7,853,305 B2 | 12/2010 | Simon et al. | |
| 7,853,313 B2 | 12/2010 | Thompson | |
| 7,865,269 B2 | 1/2011 | Prisco et al. | |
| D631,966 S | 2/2011 | Perloff et al. | |
| 7,879,045 B2 | 2/2011 | Gielen et al. | |
| 7,881,767 B2 | 2/2011 | Strommer et al. | |
| 7,881,770 B2 | 2/2011 | Melkent et al. | |
| 7,886,743 B2 | 2/2011 | Cooper et al. | |
| RE42,194 E | 3/2011 | Foley et al. | |
| RE42,226 E | 3/2011 | Foley et al. | |
| 7,900,524 B2 | 3/2011 | Calloway et al. | |
| 7,907,166 B2 | 3/2011 | Lamprecht et al. | |
| 7,909,122 B2 | 3/2011 | Schena et al. | |
| 7,925,653 B2 | 4/2011 | Saptharishi | |
| 7,930,065 B2 | 4/2011 | Larkin et al. | |
| 7,935,130 B2 | 5/2011 | Williams | |
| 7,940,999 B2 | 5/2011 | Liao et al. | |
| 7,945,012 B2 | 5/2011 | Ye et al. | |
| 7,945,021 B2 | 5/2011 | Shapiro et al. | |
| 7,953,470 B2 | 5/2011 | Vetter et al. | |
| 7,954,397 B2 | 6/2011 | Choi et al. | |
| 7,971,341 B2 | 7/2011 | Dukesherer et al. | |
| 7,974,674 B2 | 7/2011 | Hauck et al. | |
| 7,974,677 B2 | 7/2011 | Mire et al. | |
| 7,974,681 B2 | 7/2011 | Wallace et al. | |
| 7,979,157 B2 | 7/2011 | Anvari | |
| 7,983,733 B2 | 7/2011 | Viswanathan | |
| 7,988,215 B2 | 8/2011 | Seibold | |
| 7,996,110 B2 | 8/2011 | Lipow et al. | |
| 8,004,121 B2 | 8/2011 | Sartor | |
| 8,004,229 B2 | 8/2011 | Nowlin et al. | |
| 8,010,177 B2 | 8/2011 | Csavoy et al. | |
| 8,019,045 B2 | 9/2011 | Kato | |
| 8,021,310 B2 | 9/2011 | Sanborn et al. | |
| 8,035,685 B2 | 10/2011 | Jensen | |
| 8,046,054 B2 | 10/2011 | Kim et al. | |
| 8,046,057 B2 | 10/2011 | Clarke | |
| 8,052,688 B2 | 11/2011 | Wolf, II | |
| 8,054,184 B2 | 11/2011 | Cline et al. | |
| 8,054,752 B2 | 11/2011 | Druke et al. | |
| 8,057,397 B2 | 11/2011 | Li et al. | |
| 8,057,407 B2 | 11/2011 | Martinelli et al. | |
| 8,062,288 B2 | 11/2011 | Cooper et al. | |
| 8,062,375 B2 | 11/2011 | Glerum et al. | |
| 8,066,524 B2 | 11/2011 | Burbank et al. | |
| 8,073,335 B2 | 12/2011 | Labonville et al. | |
| 8,079,950 B2 | 12/2011 | Stern et al. | |
| 8,086,299 B2 | 12/2011 | Adler et al. | |
| 8,092,370 B2 | 1/2012 | Roberts et al. | |
| 8,098,914 B2 | 1/2012 | Liao et al. | |
| 8,100,950 B2 | 1/2012 | St. Clair et al. | |
| 8,105,320 B2 | 1/2012 | Manzo | |
| 8,108,025 B2 | 1/2012 | Csavoy et al. | |
| 8,109,877 B2 | 2/2012 | Moctezuma de la Barrera et al. | |
| 8,112,292 B2 | 2/2012 | Simon | |
| 8,116,430 B1 | 2/2012 | Shapiro et al. | |
| 8,120,301 B2 | 2/2012 | Goldberg et al. | |
| 8,121,249 B2 | 2/2012 | Wang et al. | |
| 8,123,675 B2 | 2/2012 | Funda et al. | |
| 8,133,229 B1 | 3/2012 | Bonutti | |
| 8,142,420 B2 | 3/2012 | Schena | |
| 8,147,494 B2 | 4/2012 | Leitner et al. | |
| 8,150,494 B2 | 4/2012 | Simon et al. | |
| 8,150,497 B2 | 4/2012 | Gielen et al. | |
| 8,150,498 B2 | 4/2012 | Gielen et al. | |
| 8,165,658 B2 | 4/2012 | Waynik et al. | |
| 8,170,313 B2 | 5/2012 | Kendrick et al. | |
| 8,179,073 B2 | 5/2012 | Farritor et al. | |
| 8,182,476 B2 | 5/2012 | Julian et al. | |
| 8,184,880 B2 | 5/2012 | Zhao et al. | |
| 8,202,278 B2 | 6/2012 | Orban, III et al. | |
| 8,204,575 B2 * | 6/2012 | Stetz | A61B 90/39 600/426 |
| 8,208,708 B2 | 6/2012 | Homan et al. | |
| 8,208,988 B2 | 6/2012 | Jensen | |
| 8,219,177 B2 | 7/2012 | Smith et al. | |
| 8,219,178 B2 | 7/2012 | Smith et al. | |
| 8,220,468 B2 | 7/2012 | Cooper et al. | |
| 8,224,024 B2 | 7/2012 | Foxlin et al. | |
| 8,224,484 B2 | 7/2012 | Swarup et al. | |
| 8,225,798 B2 | 7/2012 | Baldwin et al. | |
| 8,228,368 B2 | 7/2012 | Zhao et al. | |
| 8,231,610 B2 | 7/2012 | Jo et al. | |
| 8,263,933 B2 | 7/2012 | Hartmann et al. | |
| 8,239,001 B2 | 8/2012 | Verard et al. | |
| 8,241,271 B2 | 8/2012 | Millman et al. | |
| 8,248,413 B2 | 8/2012 | Gattani et al. | |
| 8,256,319 B2 | 9/2012 | Cooper et al. | |
| 8,271,069 B2 | 9/2012 | Jascob et al. | |
| 8,271,130 B2 | 9/2012 | Hourtash | |
| 8,281,670 B2 | 10/2012 | Larkin et al. | |
| 8,282,653 B2 | 10/2012 | Nelson et al. | |
| 8,301,226 B2 | 10/2012 | Csavoy et al. | |
| 8,311,611 B2 | 11/2012 | Csavoy et al. | |
| 8,320,991 B2 | 11/2012 | Jascob et al. | |
| 8,332,012 B2 | 12/2012 | Kienzle, III | |
| 8,333,755 B2 | 12/2012 | Cooper et al. | |
| 8,335,552 B2 | 12/2012 | Stiles | |
| 8,335,557 B2 | 12/2012 | Maschke | |
| 8,348,931 B2 | 1/2013 | Cooper et al. | |
| 8,353,963 B2 | 1/2013 | Glerum | |
| 8,358,818 B2 | 1/2013 | Miga et al. | |
| 8,359,730 B2 | 1/2013 | Burg et al. | |
| 8,374,673 B2 | 2/2013 | Adcox et al. | |
| 8,374,723 B2 | 2/2013 | Zhao et al. | |
| 8,379,791 B2 | 2/2013 | Forthmann et al. | |
| 8,386,019 B2 | 2/2013 | Camus et al. | |
| 8,392,022 B2 | 3/2013 | Ortmaier et al. | |
| 8,394,099 B2 | 3/2013 | Patwardhan | |
| 8,395,342 B2 | 3/2013 | Prisco | |
| 8,398,634 B2 | 3/2013 | Manzo et al. | |
| 8,400,094 B2 | 3/2013 | Schena | |
| 8,414,957 B2 | 4/2013 | Enzerink et al. | |
| 8,418,073 B2 | 4/2013 | Mohr et al. | |
| 8,450,694 B2 | 5/2013 | Baviera et al. | |
| 8,452,447 B2 | 5/2013 | Nixon | |
| RE44,305 E | 6/2013 | Foley et al. | |
| 8,462,911 B2 | 6/2013 | Vesel et al. | |
| 8,465,476 B2 | 6/2013 | Rogers et al. | |
| 8,465,771 B2 | 6/2013 | Wan et al. | |
| 8,467,851 B2 | 6/2013 | Mire et al. | |
| 8,467,852 B2 | 6/2013 | Csavoy et al. | |
| 8,469,947 B2 | 6/2013 | Devengenzo et al. | |
| RE44,392 E | 7/2013 | Hynes | |
| 8,483,434 B2 | 7/2013 | Buehner et al. | |
| 8,483,800 B2 | 7/2013 | Jensen et al. | |
| 8,486,532 B2 | 7/2013 | Enzerink et al. | |
| 8,489,235 B2 | 7/2013 | Moll et al. | |
| 8,500,722 B2 | 8/2013 | Cooper | |
| 8,500,728 B2 | 8/2013 | Newton et al. | |
| 8,504,201 B2 | 8/2013 | Moll et al. | |
| 8,506,555 B2 | 8/2013 | Ruiz Morales | |
| 8,506,556 B2 | 8/2013 | Schena | |

(56) References Cited

U.S. PATENT DOCUMENTS

| | | |
|---|---|---|
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 10,799,298 B2 | 10/2020 | Crawford et al. |
| 2001/0036302 A1 | 11/2001 | Miller |
| 2002/0035321 A1 | 3/2002 | Bucholz et al. |
| 2003/0095637 A1 | 5/2003 | Sabczynski et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2005/0281385 A1* | 12/2005 | Johnson .............. A61B 34/20 378/163 |
| 2006/0100610 A1 | 5/2006 | Wallace et al. |
| 2006/0173329 A1 | 8/2006 | Marquart et al. |

(56) References Cited

U.S. PATENT DOCUMENTS

| | | |
|---|---|---|
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |

(56) References Cited

U.S. PATENT DOCUMENTS

| | | |
|---|---|---|
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0228208 A1* | 8/2016 | Samsonov ............ A61B 6/025 |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2019/0328482 A1* | 10/2019 | Izmirli ................ A61B 6/0492 |
| 2020/0397370 A1* | 12/2020 | Eslami ................ A61B 90/06 |
| 2022/0142730 A1* | 5/2022 | Wolf .................... A61B 90/361 |
| 2022/0304750 A1* | 9/2022 | Wan .................... A61B 17/3403 |
| 2022/0346831 A1* | 11/2022 | Wan .................... A61B 90/39 |

* cited by examiner

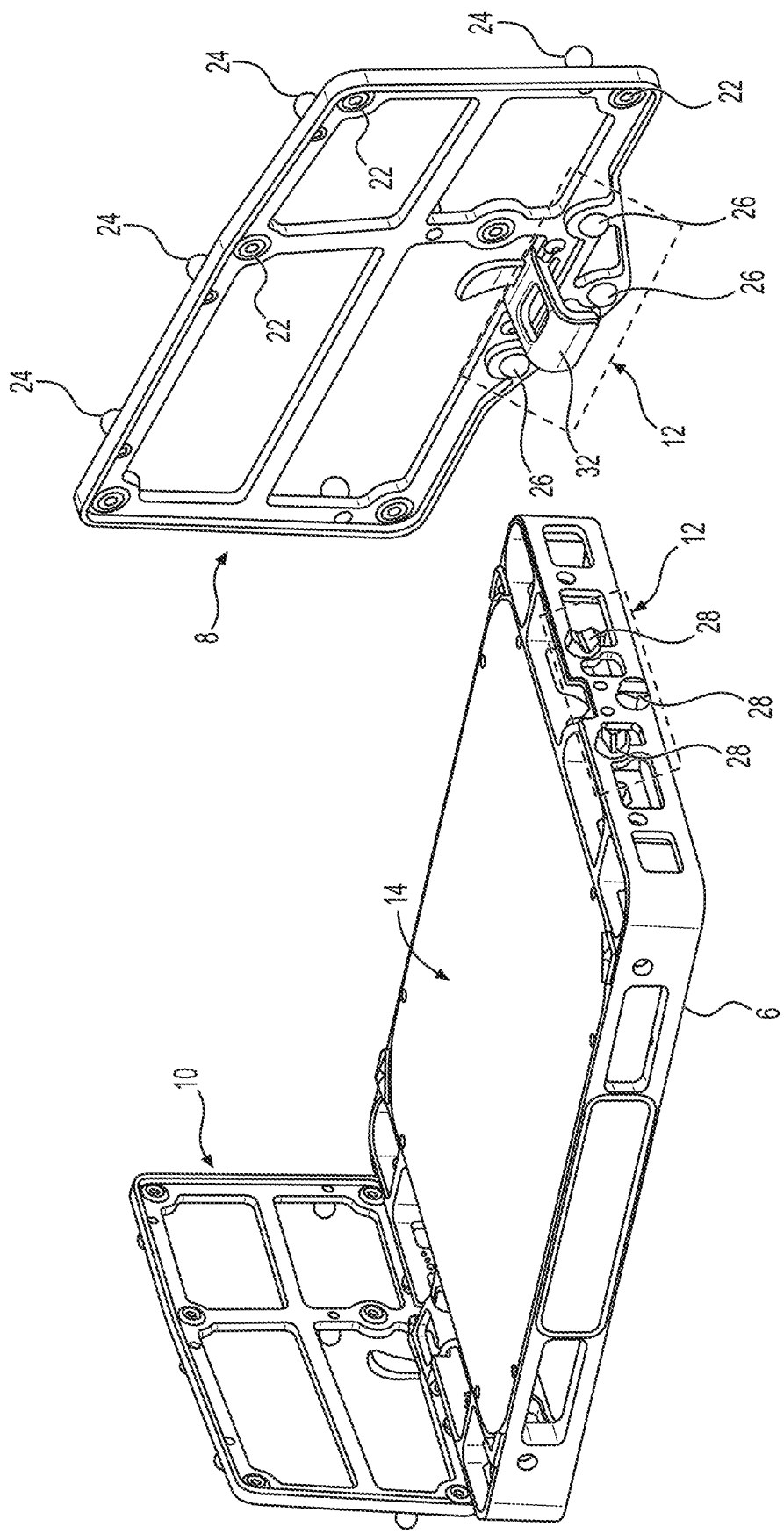

SURGICAL NAVIGATION SYSTEM WITH FLAT PANEL REGISTRATION FIXTURE

FIELD

The present disclosure relates to position recognition systems, and in particular, the registration of a medical image to a three-dimensional tracking space.

BACKGROUND

Surgical navigation requires registration of a medical image or a set of medical images to a three-dimensional tracking space, such that a surgical device detected as a rigid body in the tracking space can then be displayed as a graphic overlaid on the medical images in the correct position relative to the patient's anatomy. This process is one-way registration of the image to the tracking coordinate system. In robotic navigation, two-way co-registration of the image and tracking coordinate systems is also necessary to allow positioning of a rigid body from the image coordinate system to the tracking coordinate system. In practice, a desired trajectory is overlaid on the medical image, defining a medical object (e.g., surgical screw) as a rigid body in the medical image coordinate system, where co-registration allows the rigid body to be simultaneously defined in the tracking space. Since the robot is calibrated so that its position in the tracking space is known, the robot can then move to a known position along the desired trajectory to hold a tool for surgery that will allow a screw, needle, or other instrument to follow the desired trajectory.

The process of co-registering a three-dimensional image volume such as a computed tomography (CT) scan with the tracking space is possible because the CT image volume and the camera space are both well defined. The positions of fiducials in the image volume can be detected accurately by image processing and the positions of tracking markers in the camera space can be detected accurately by stereophotogrammetry. A registration fixture containing both tracking markers and imaging fiducials in a known relative position can therefore provide the required co-registration when working with a three-dimensional image. However, when working from multiple two-dimensional (2D) images the process of registering these images with the tracking space becomes challenging.

In the current pre-operative CT robotic/navigation workflow, a preoperative 3D CT is registered to the tracking camera's coordinate system using a pair of 2D tracked fluoro images. For each fluoro image, the locations of the image plane and emitter are optically tracked via a fixture attached to the fluoro unit. The algorithm works by generating synthetic fluoro shots (digitally reconstructed radiographs ((DRRs)) mathematically by simulating the X-ray path through the CT volume. When a match is found between the actual X-ray images and DRRs, registration is achieved because the locations of the image plane and emitter are simultaneously known relative to the CT volume and relative to the cameras.

One part of the above algorithm for registering the CT image to the tracking cameras is to accurately track the location of the image plane and emitter relative to the patient tracker so that the DRRs are generated with correct corresponding configuration of the virtual emitter and virtual collector relative to the CT volume. The way that the existing software tracks the image plane is by tracking a fixture directly attached to the face of the image collector of the C-arm. The emitter location is then accurately determined by implementing a commonly used "pinhole camera" algorithm where the shadows of two planes of BBs passing through the fixture are analyzed to determine where the emitter must have been relative to the collector to create such shadows.

One underlying assumption of the CT-fluoro registration process is that the far BB plane of the tracked fluoro fixture, which is up against the physical collector of the C-arm, can be considered to be coincident with the X-ray image plane, even though the BB plane is really several centimeters from the hardware that detects the X-rays. The reason this simplification is valid is that the only effect moving the BB plane away from the imaging hardware has been to magnify the image uniformly. That is, if it were possible to move the collector linearly away from the emitter, leaving the fluoro fixture in the same place relative to the emitter, equivalent shadows of BBs would be generated at different collector distances with the only difference between the images from the different collector locations being the increasing image magnification. FIG. 17 illustrates key dimensions looking at a plane perpendicular to the collector plate's plane, and with BBs in the field of view whose shadows appear on the collector plate. The resolution of the X-ray images (pixels per mm) is unknown when taking X-ray shots and is not important in the registration process, so any magnification from where the image plane is actually linearly offset relative to the fixture plane can be unimportant.

SUMMARY

Some embodiments of the present disclosure are directed to a registration fixture is provided for registration of a medical image to a three-dimensional tracking space. The registration fixture includes a base frame, an orientation plate, and a registration plate. The base frame is adapted to be mounted to an x-ray medical imaging device. The orientation plate is attached to the base frame and has a first set of radiopaque markers arranged along at least four radial lines which extend from a center location. The radial lines are angularly spaced apart about the center location. At least three of the radiopaque markers are arranged along each of the radial lines. The registration plate is attached to the base frame and spaced apart from the orientation plate. The registration plate has a second set of radiopaque markers arranged along a circle.

Some embodiments of the present disclosure are directed to a surgical navigation system for registration of a medical image to a three-dimensional tracking space. The surgical navigation system includes at least one processor and at least one memory storing instructions executable by the at least one processor to perform operations. The operations include to obtain an image generated by an x-ray medical imaging device. The operations identify in the image a first set of radiopaque markers based on recognizing the first set of radiopaque markers are arranged along at least four radial lines which extend from a center location, based on recognizing the radial lines are angularly spaced apart about the center location, and based on recognizing at least three of the radiopaque markers are arranged along each of the radial lines. The operations identify in the image locations of a second set of radiopaque markers based on recognizing the second set of radiopaque markers are arranged along a circle, where the first set of radiopaque markers are on an orientation plate, the second set of radiopaque markers are on a registration plate spaced apart from the orientation plate, and the orientation plate and the registration plate are attached to a base frame of a fixture mounted to the x-ray medical image device. The operations register the image to a three-dimensional tracking space based on comparison of locations of the first set radiopaque markers in the image to locations of the second set radiopaque markers in the image.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures:

FIG. 41 is a perspective view of a base frame and a side frame of the registration fixture of FIG. 38 prior to assembly.

Figure 1:
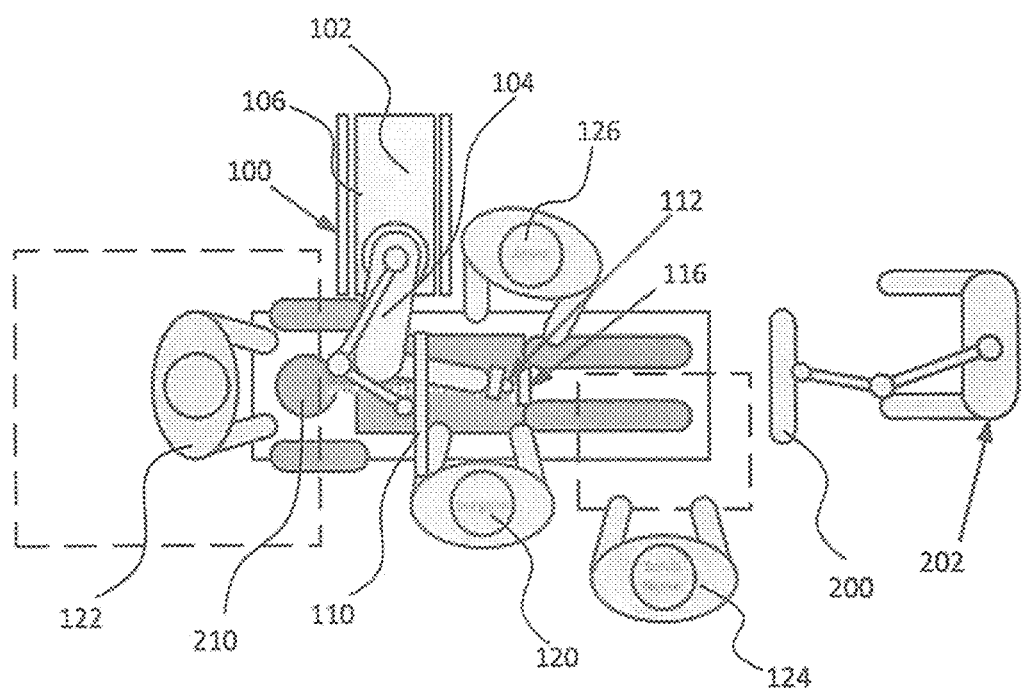
FIG. 1 is an overhead view of a potential arrangement for locations of the robotic system, patient, surgeon, and other medical personnel during a surgical procedure.

While the invention has been described in connection with certain preferred embodiments, other embodiments would be understood by one of ordinary skill in the art and are encompassed herein.

DETAILED DESCRIPTION

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
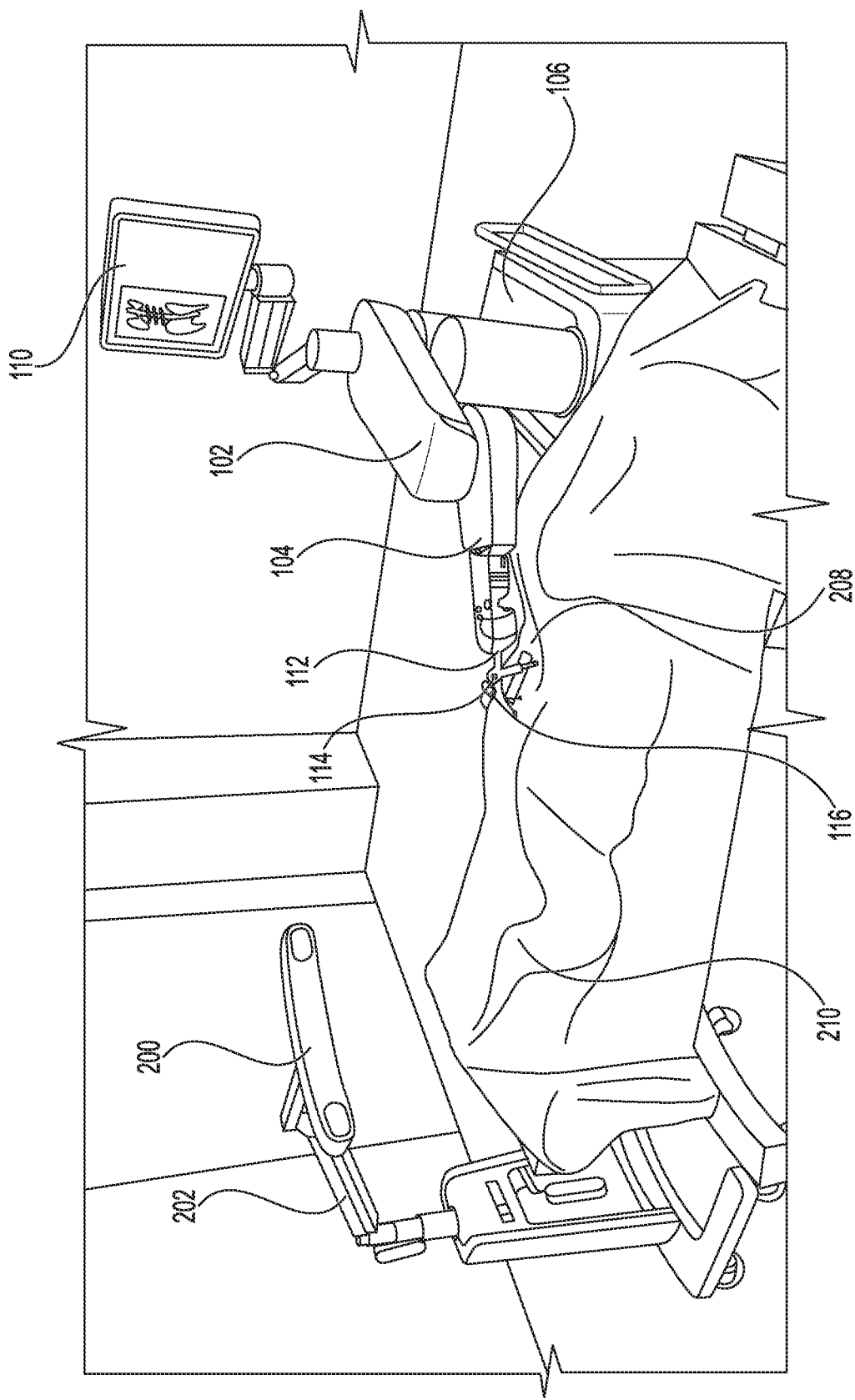
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screwdriver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
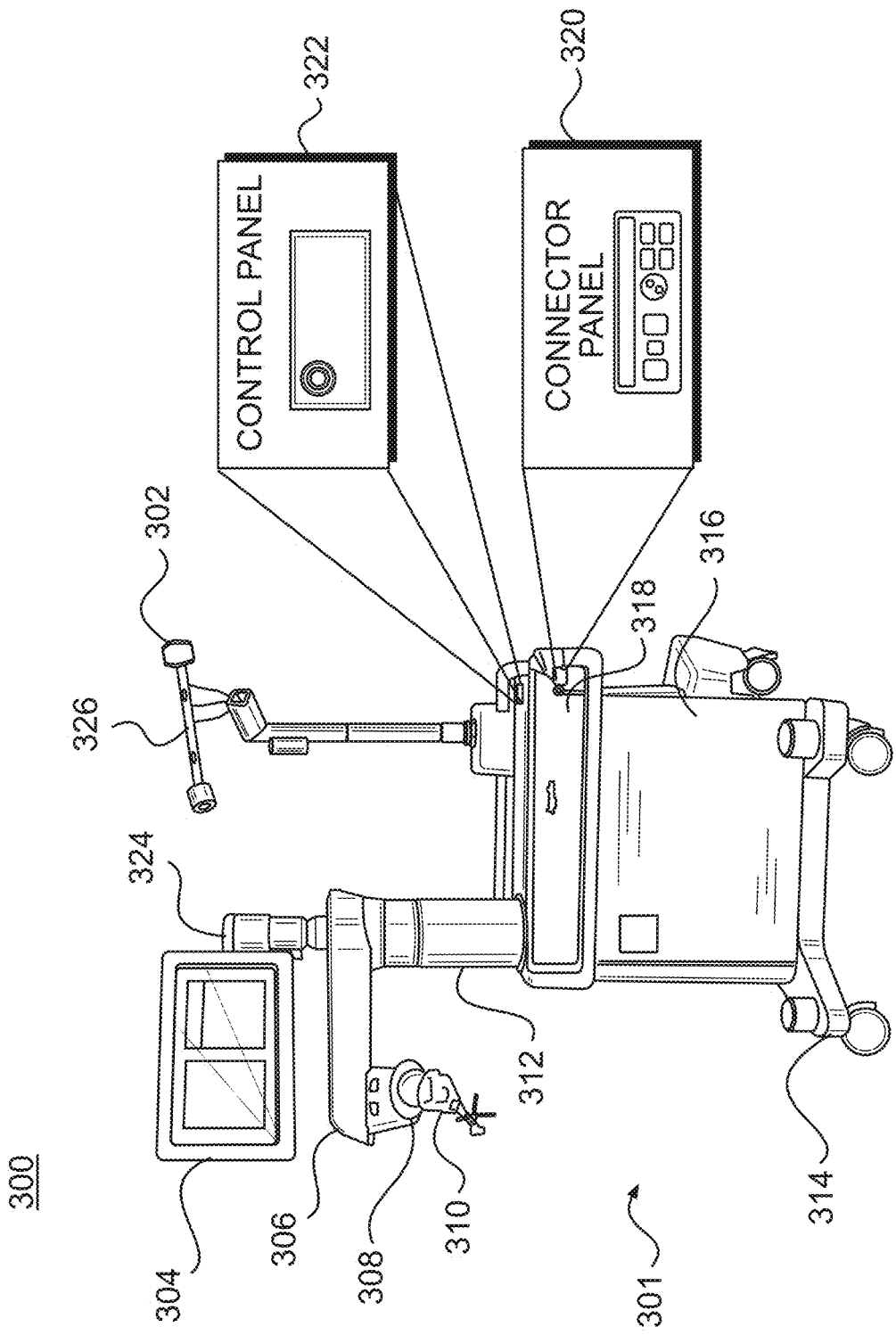
FIG. 3 illustrates a surgical robotic system in accordance with an exemplary embodiment.
Figure 4:
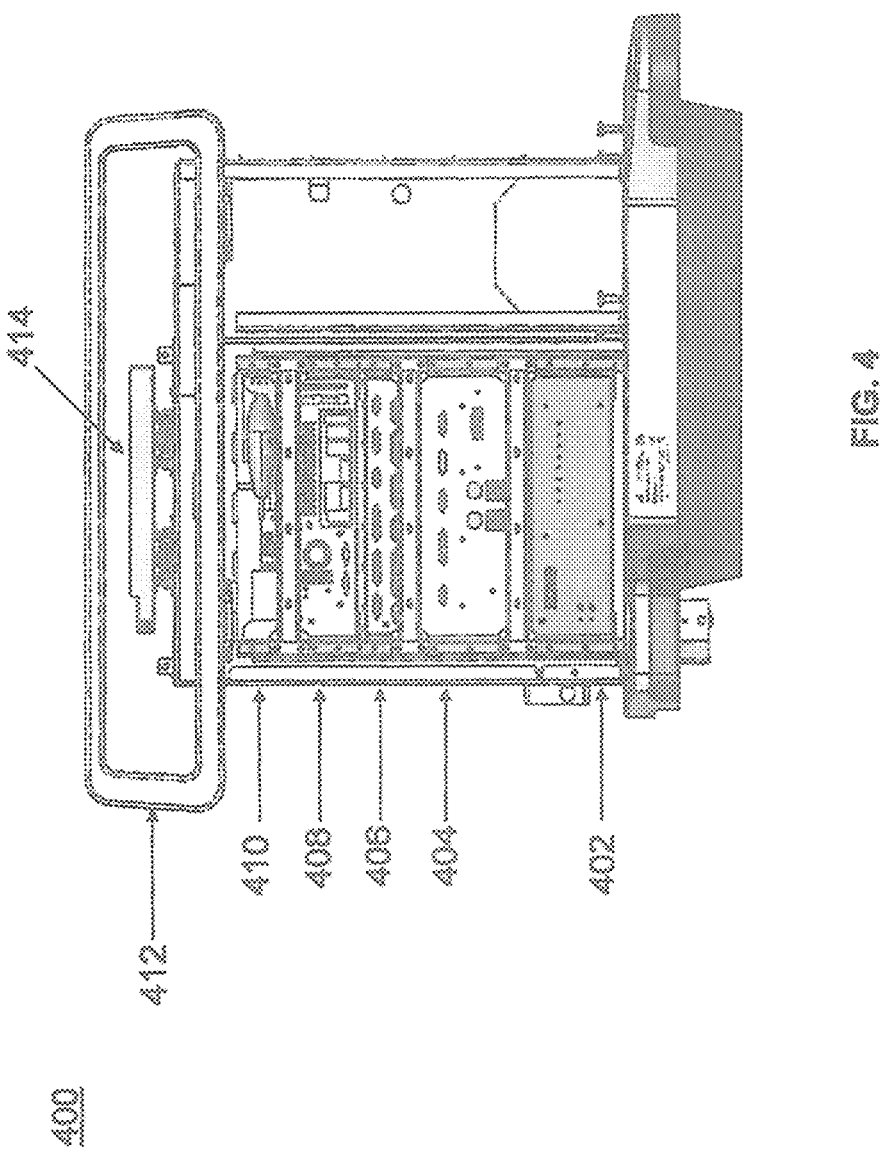
FIG. 4 illustrates a portion of a surgical robot in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2. FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
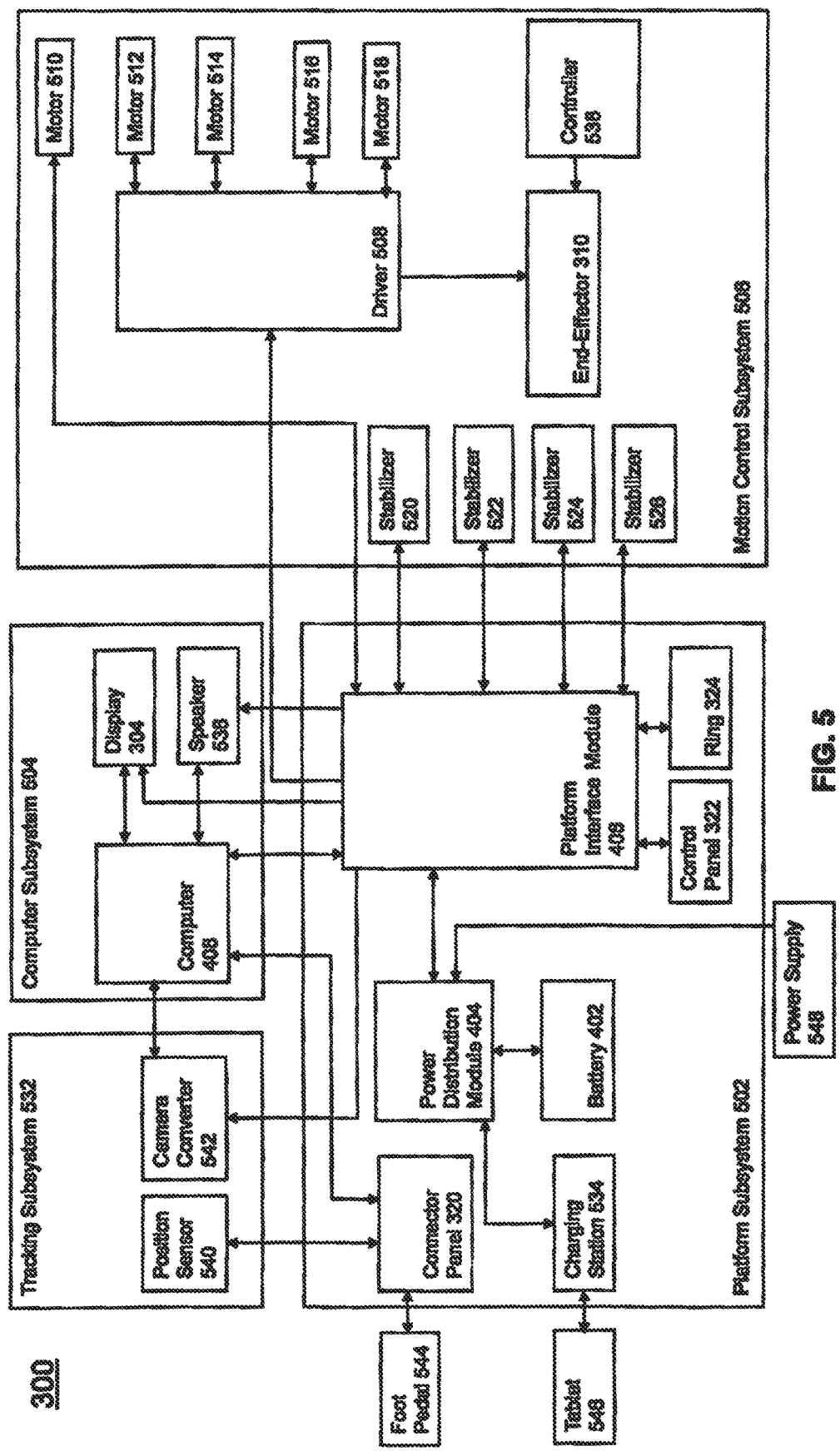
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein. Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408. [0057] Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure. Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

Figure 6:
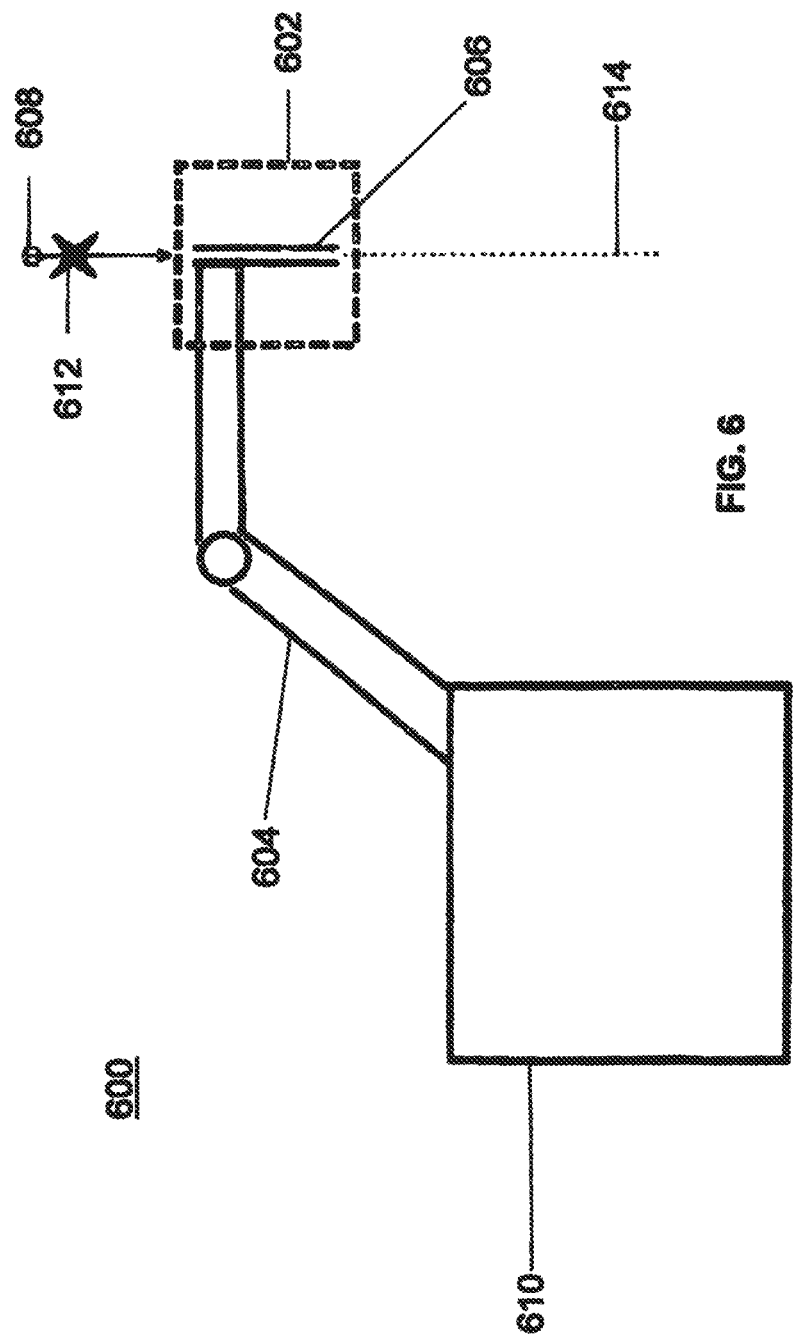
FIG. 6 illustrates a surgical robot in accordance with an exemplary embodiment.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

Figure 8:
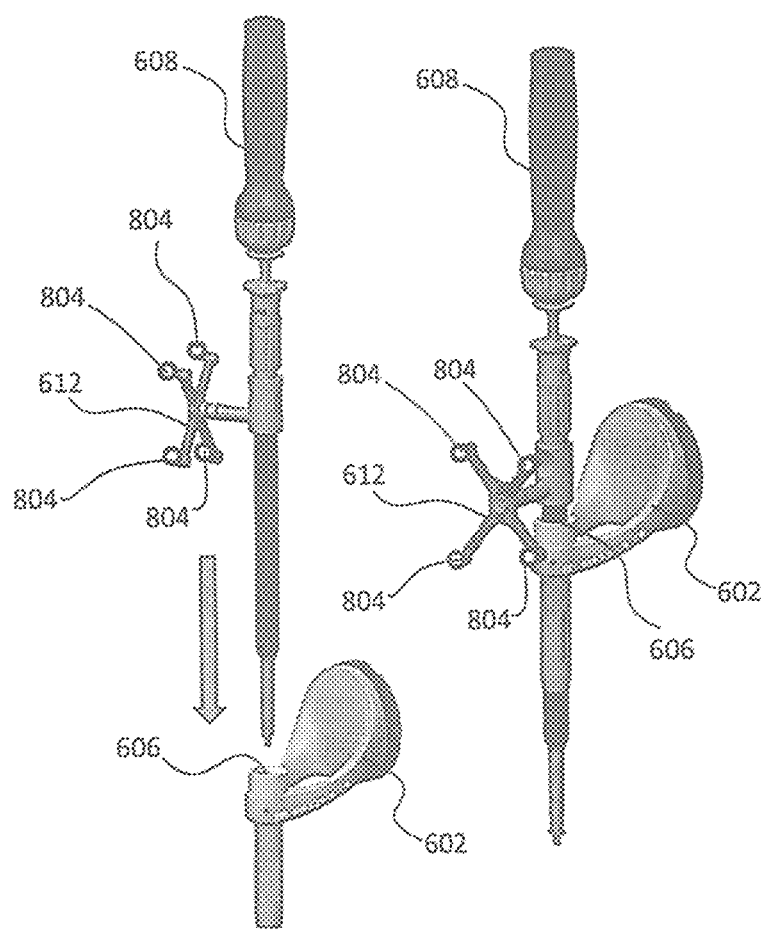
FIG. 8 illustrates a surgical instrument and the end-effector, before and after, inserting the surgical instrument into the guide tube of the end-effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

Figure 7:
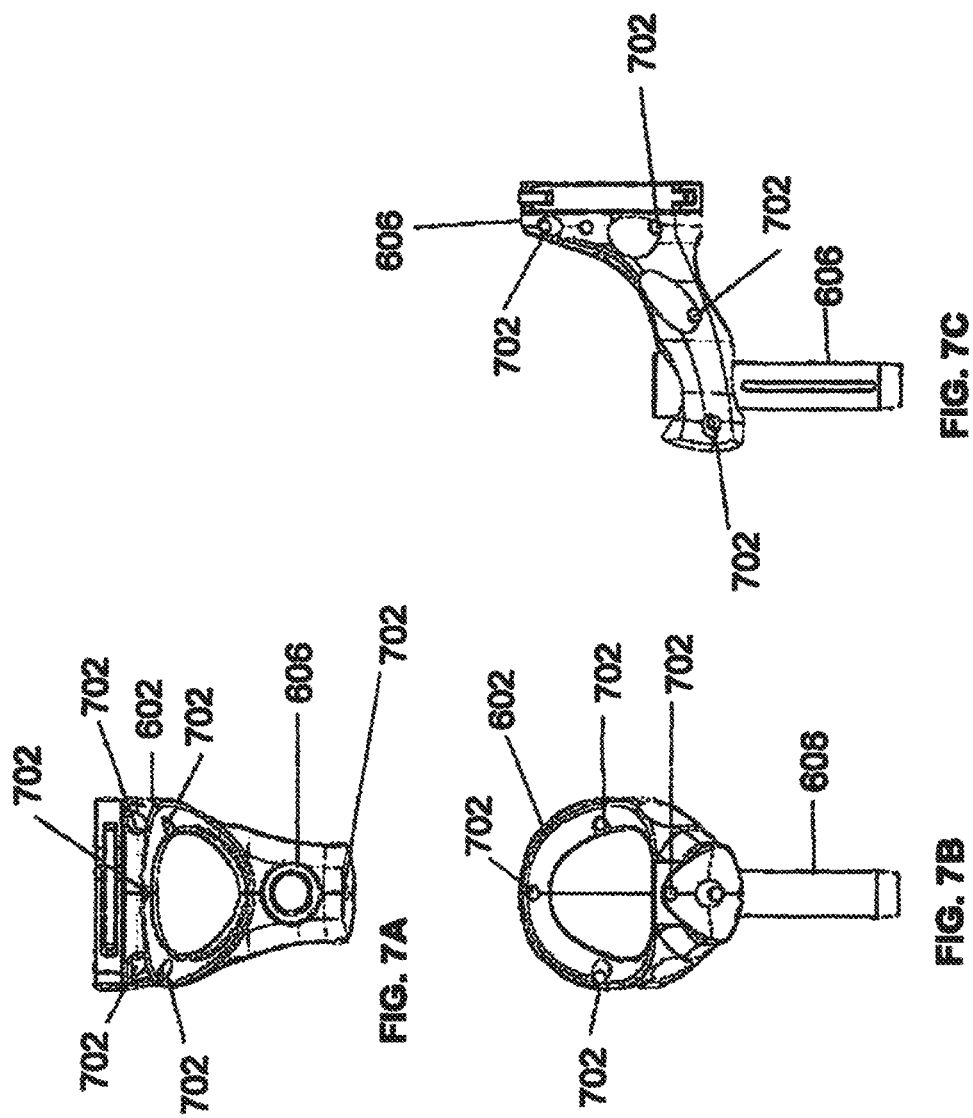
FIGS. 7A-7C illustrate an end-effector in accordance with an exemplary embodiment.

FIGS. 7A, 7B, and 7C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device 100, 300, 600. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screwdriver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screwdriver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
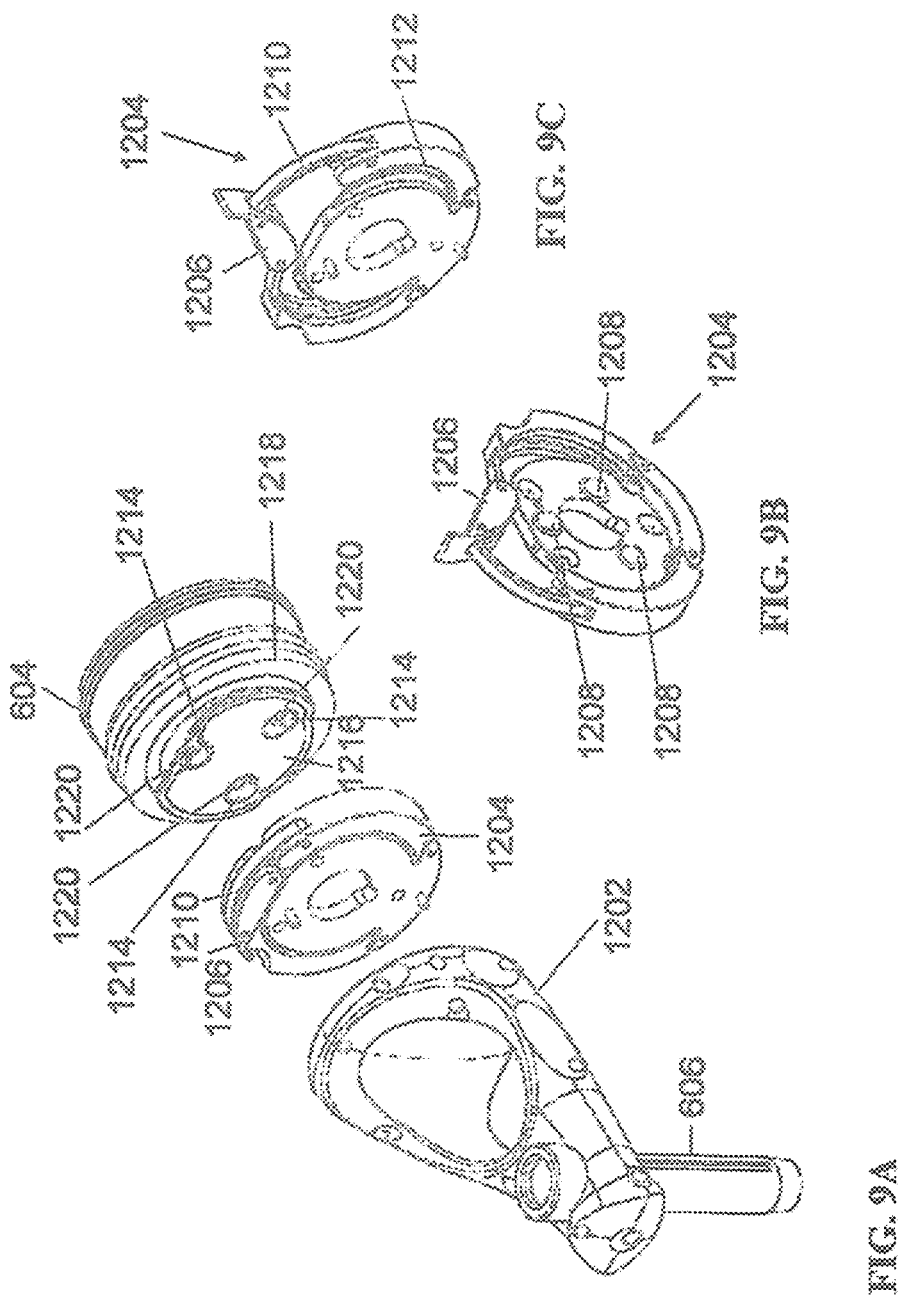
FIGS. 9A-9C illustrate portions of an end-effector and robot arm in accordance with an exemplary embodiment.

FIGS. 9A-9C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220. [0072] End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Figure 10:
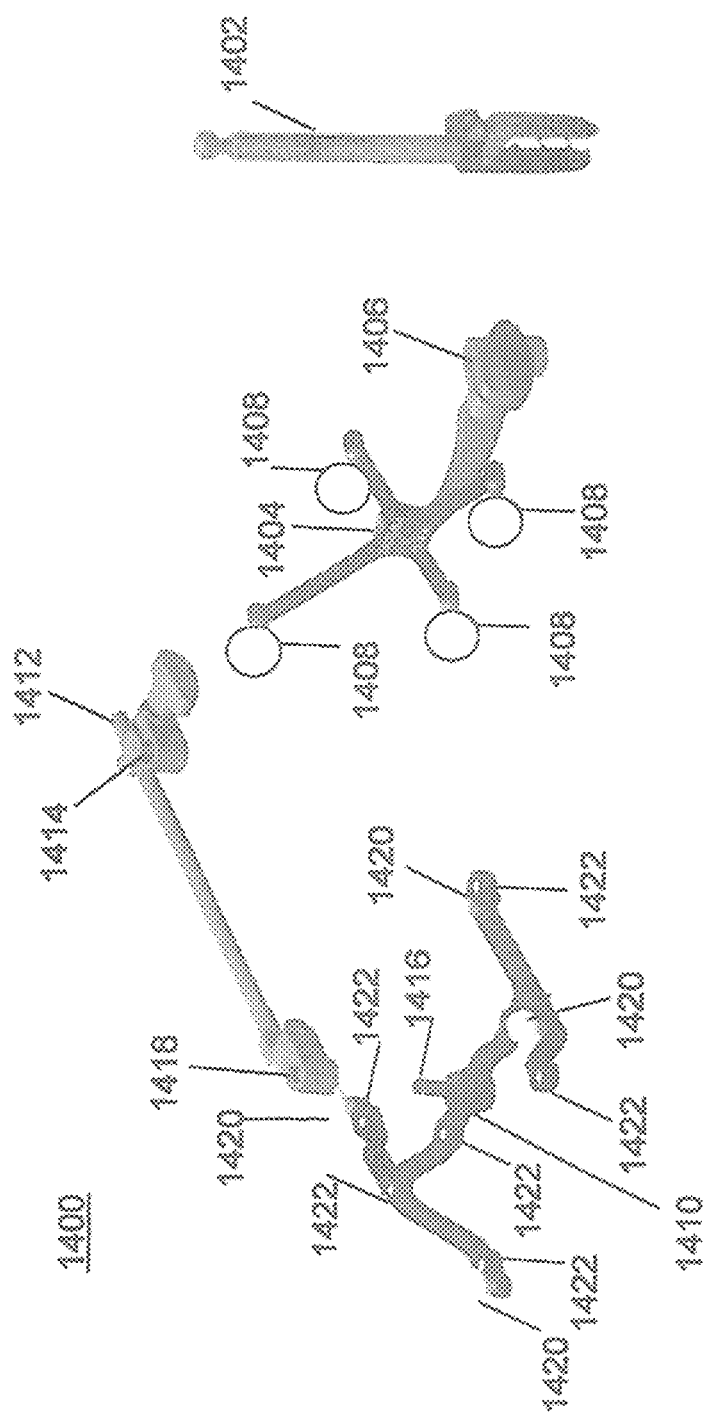
FIG. 10 illustrates a dynamic reference array, an imaging array, and other components in accordance with an exemplary embodiment.
Figure 11:
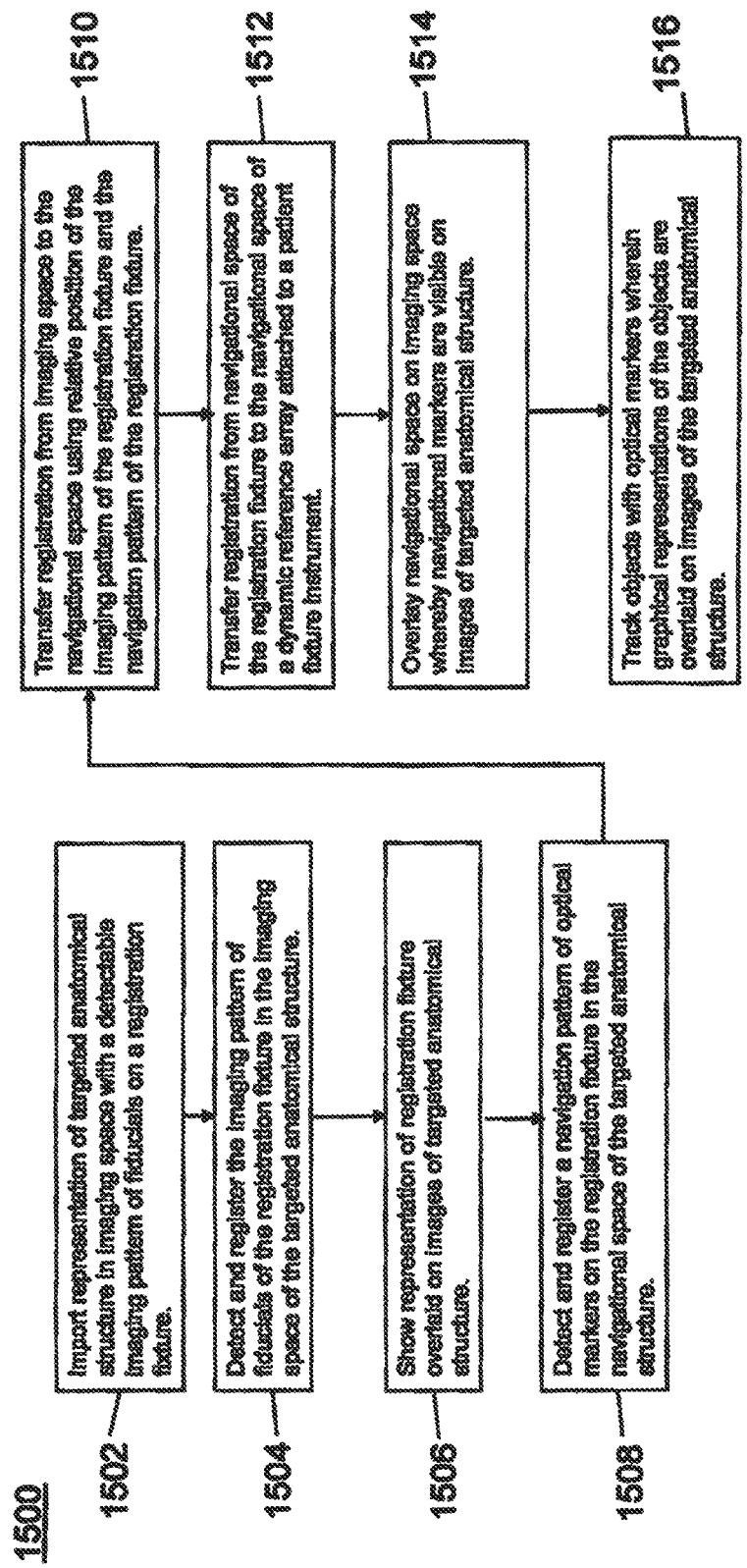
FIG. 11 illustrates a method of registration in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
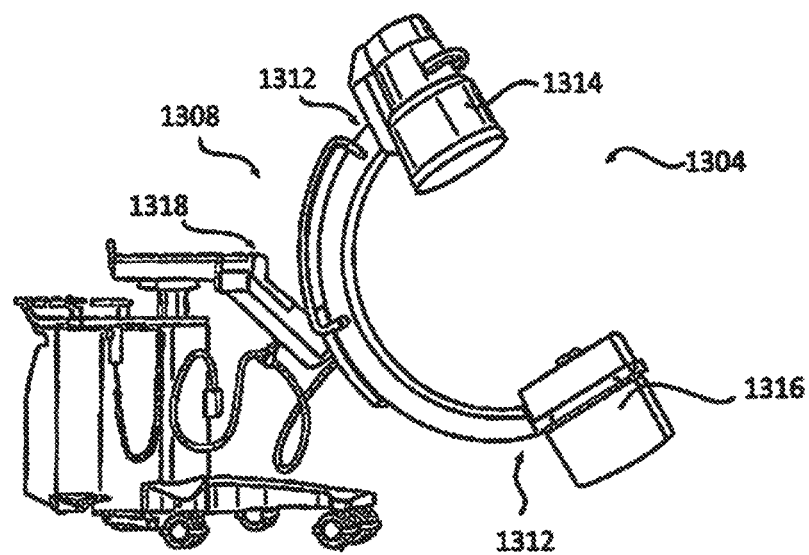
FIG. 12A-12B illustrate embodiments of imaging devices according to exemplary embodiments.
Figure 12B:
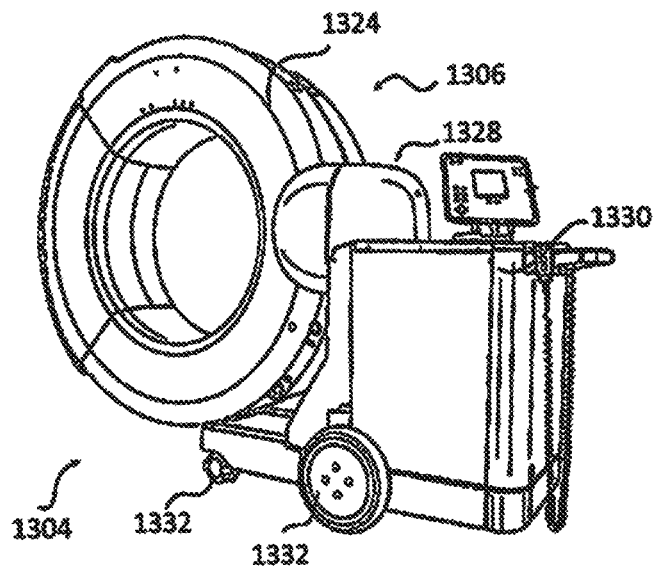

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Figure 13:
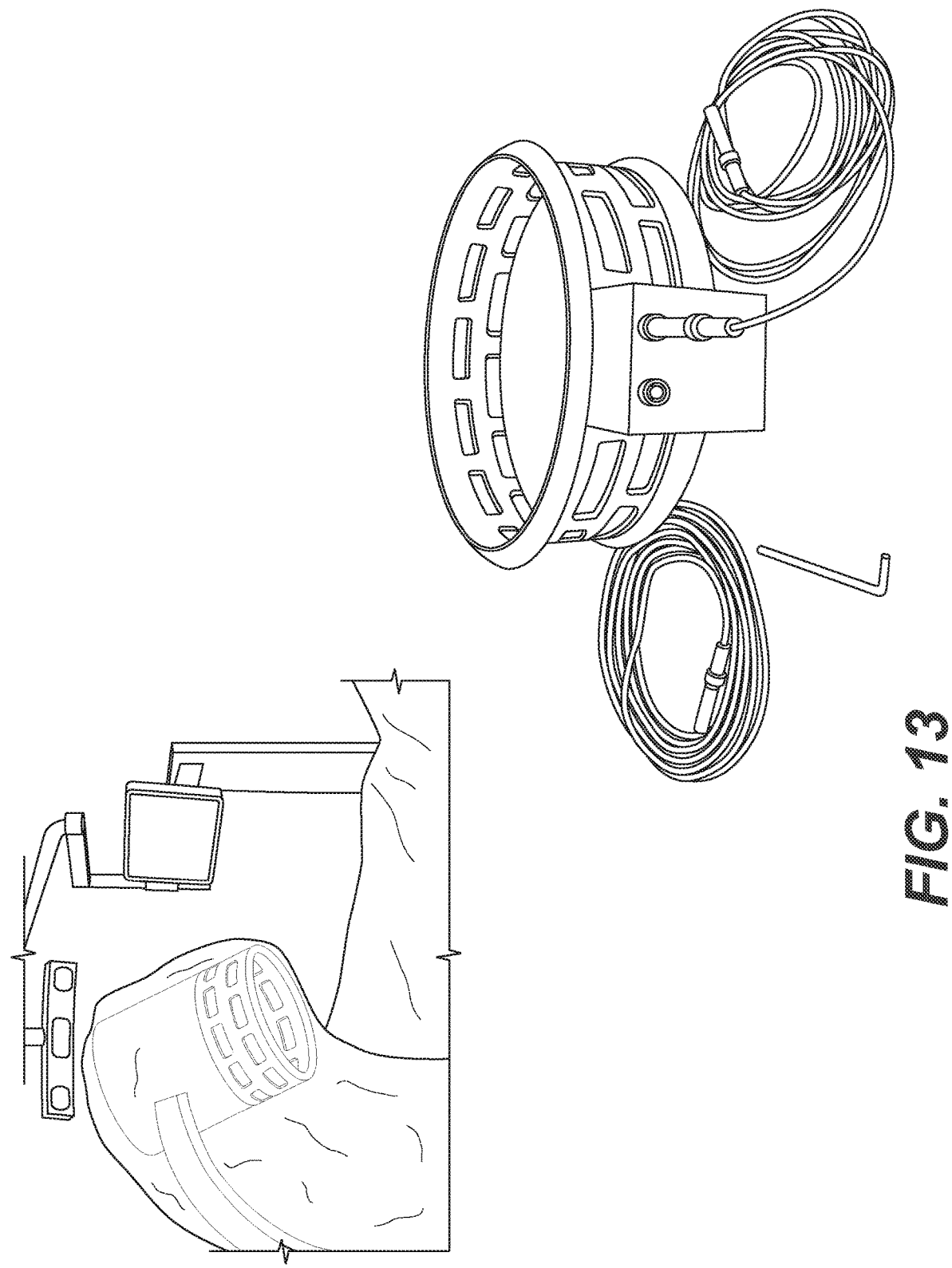
FIG. 13 shows one embodiment of a navigation fixture.

There are methods for displaying the simulated projection of a surgical tool overlaid on a fluoroscopic image to assist in surgery through one-way registration of the medical image to the tracking space. For example, a calibrating fixture may be attached to the image intensifier of a fluoroscope, such as illustrated in FIG. 13. The fixture contains rows of small metallic spheres (hereafter referred to as 'BBs') with known spacing that appear on the x-ray image, and also contains an optical tracking array that provides the three-dimensional (3D) position of the fixture in the tracking space. Through image processing and geometric computations, it can be determined how a tool placed in the path of the x-rays should appear as a projection on the x-ray image. The 3D position of the tool, which has a tracking array attached, is tracked in the coordinate system of the tracker (e.g., cameras). Then, a graphical representation of the tool is overlaid on the x-ray images to provide "virtual fluoroscopy" with roughly the same visual information that would be seen if continuous x-rays were taken while holding the tool in the surgical field. A benefit of this method is that the patient and medical staff are exposed to much less radiation as the virtual fluoroscopy can provide continuous updates of tool position overlaid on a single x-ray image.

Figure 14:
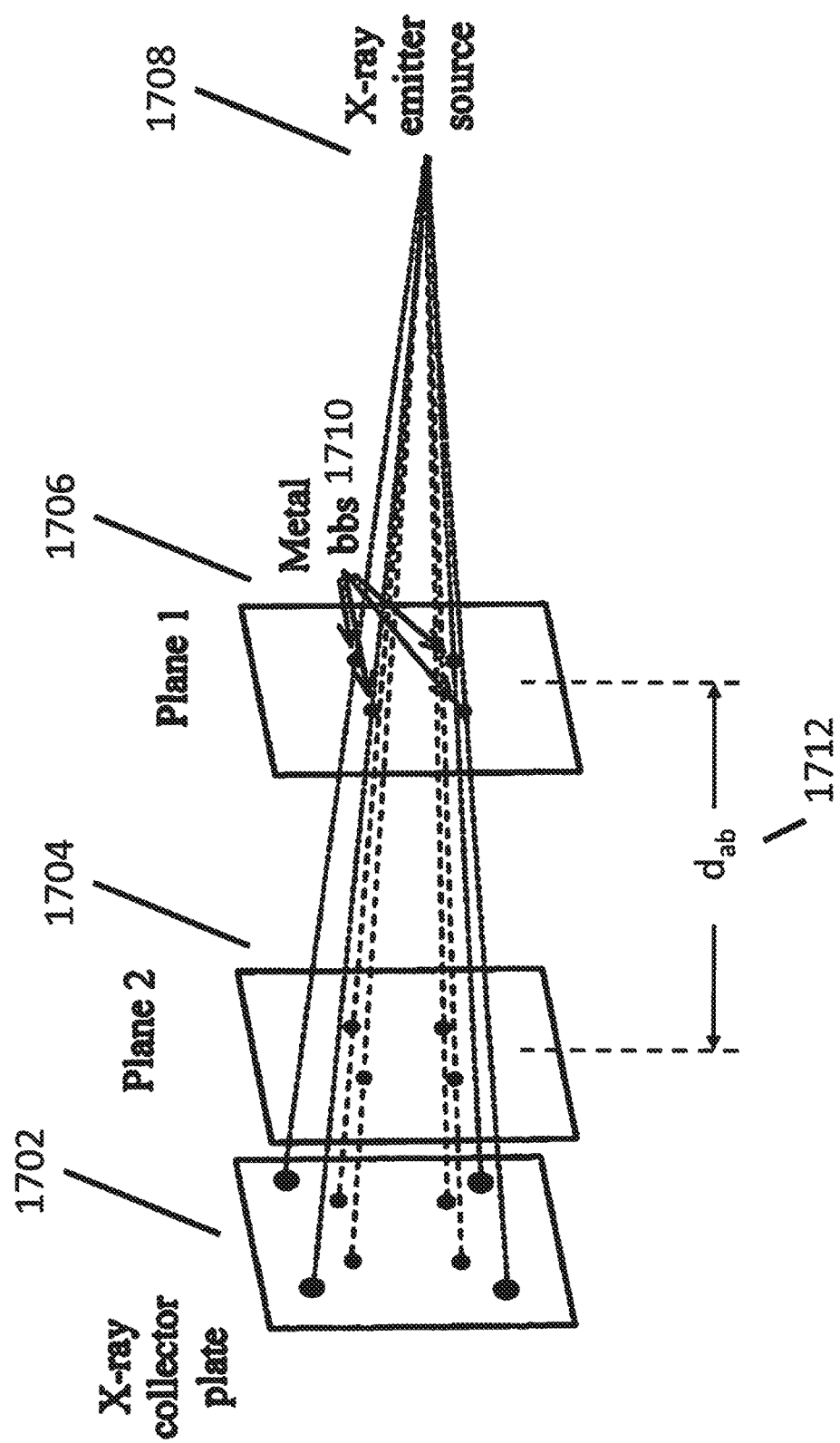
FIG. 14 illustrates an x-ray (fluoroscope) collector plate showing the theoretical projection of small metallic spheres (hereafter referred to as 'BBs') within two planes at different distances from the source.

Although this method maps 3D tool position to two-dimensional (2D) medical images, it is not necessary for that application to map points detected on the 2D medical images to the 3D tracking space, i.e., to co-register the medical image space with the tracking space. However, it is possible to obtain such mapping by considering the vectors extending from emitter to collector. FIG. 14 illustrates an x-ray (e.g., fluoroscope) collector plate 1702 showing the theoretical projection of BBs 1710 within two planes 1704 and 1706 at different distances from the source 1708. X-ray collector plate 1702, Plane 1 1706, and Plane 2 1704 are shown as being parallel and concentric. In this instance, the x-ray emitter 1708 is assumed to be a point, and rays from the source to collector travel out from this point in a conical pattern. Because of this conical pattern, the BBs 1710 from Plane 1 1706 appear magnified on the x-ray collector plate 1702 relative to the BBs 1710 from Plane 2 1704, although they are actually spaced the same in this example. This phenomenon is known as parallax.

Figure 15:
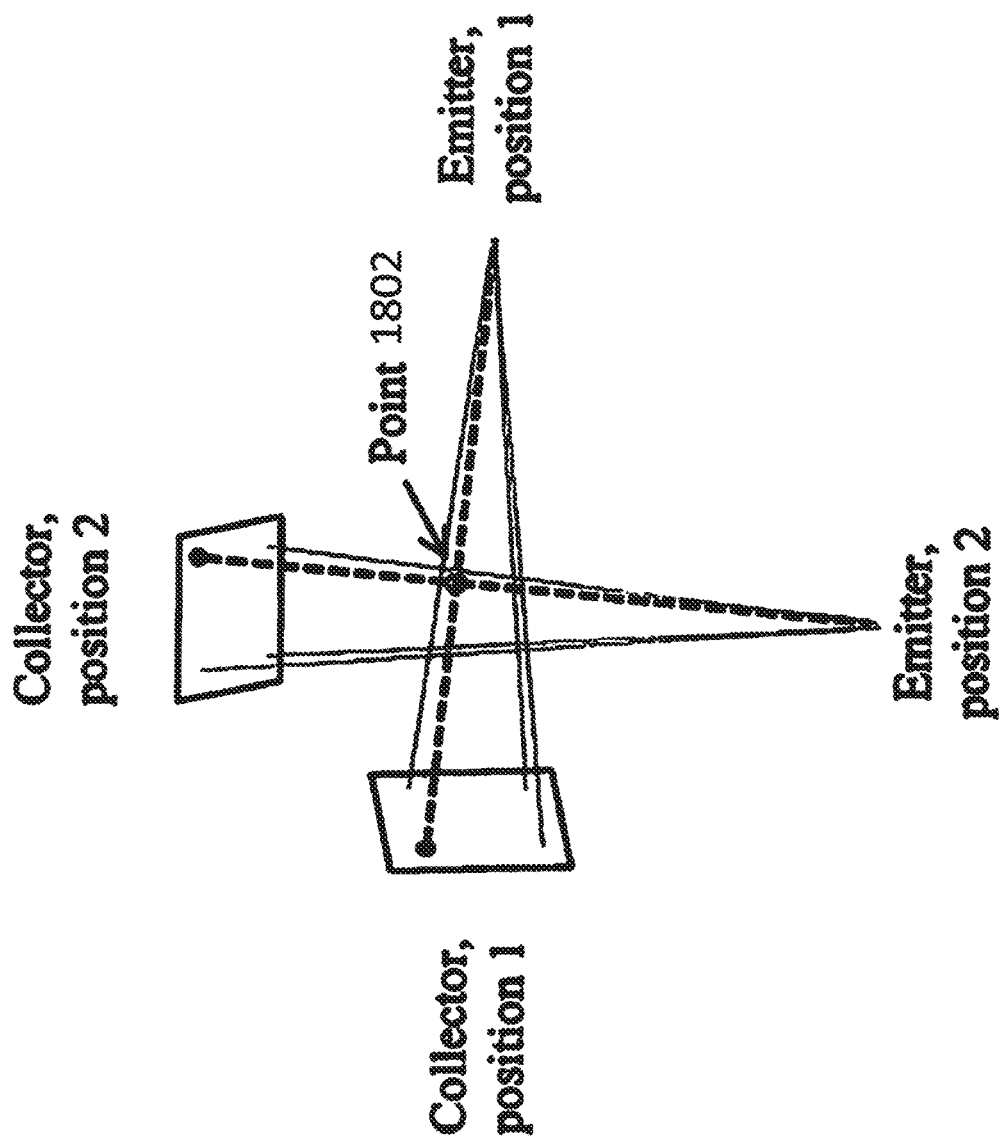
FIG. 15 illustrates two x-ray projections taken from the same radio-opaque point from two different perspectives to produce a 3D location.

Considering a case where one x-ray view is taken from a perspective substantially different than another x-ray view, such as depicted in FIG. 15, and where the exact positions of the collector and emitter in 3D are known from tracking or other means, the vectors extending in a conical pattern from emitter to collector can be traced back to where they intersect an anatomical point of interest 1802 that is present in both views. In this instance, "vectors" could mean vectors determined from visible x-ray shadows of the BBs, or any vector calculated (e.g., interpolated) to match the conical pattern deduced from the visible x-ray shadows. The 3D position of that anatomical point of interest may then be determined because there is a unique solution at the intersection of the vectors from the two views. That is, from one view, it is not possible to deduce 3D position of a reference point because the point could be anywhere along the vector from source to emitter and would appear at the same location on the collector plate. The second view provides the unique position along the vector where the point must be.

Figure 16:
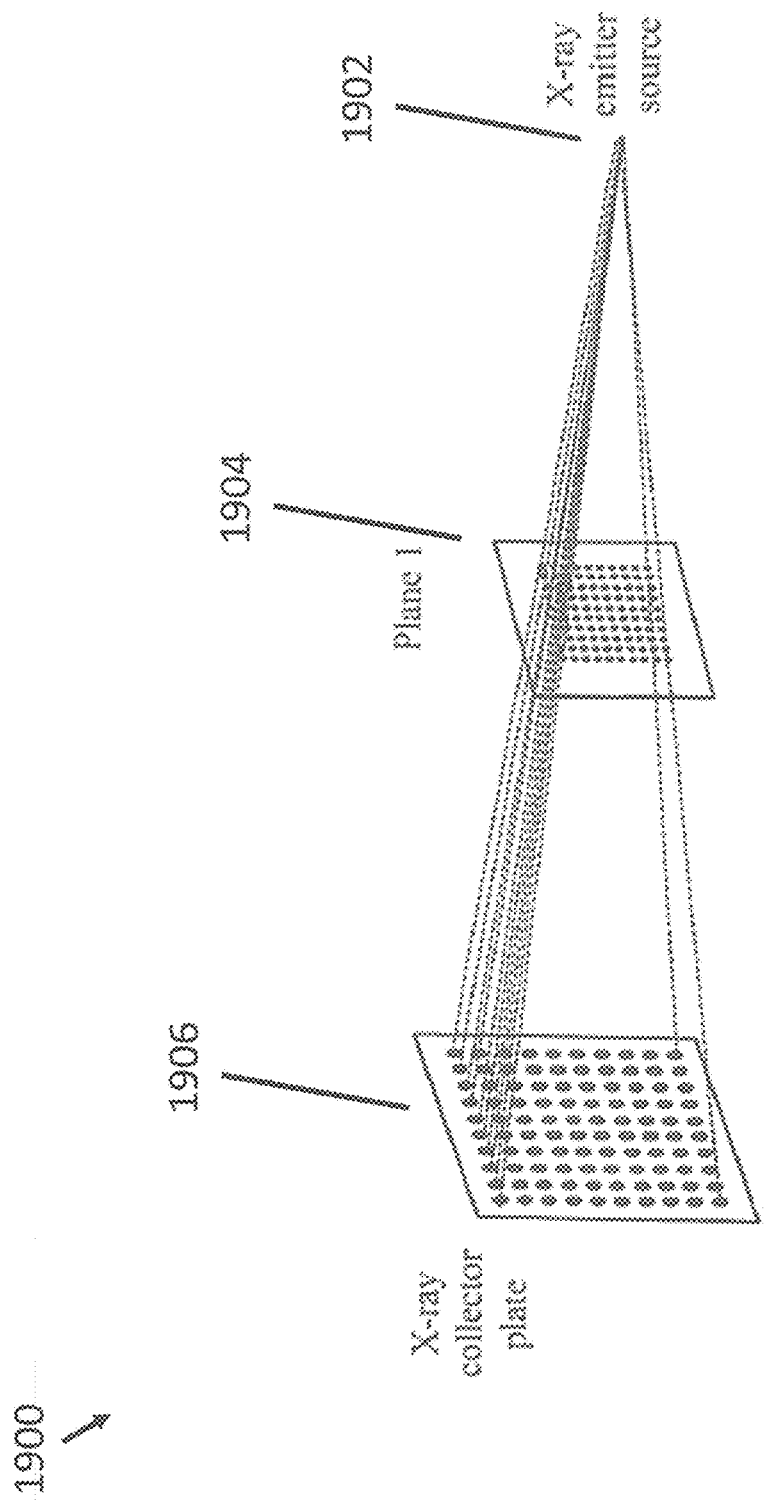
FIG. 16 illustrates an x-ray image taken through a plane parallel to the collector plate of a grid of BBs.

FIG. 14 shows just 4 BBs 1710 on two parallel planes 1704 and 1706. These BBs could provide the basis for methods to detect the position of an object in 3D from multiple 2D x-ray views. However, to provide better accuracy, a dense grid of BBs such as shown in FIG. 16 (e.g., tens or hundreds) could be used instead, which would allow vectors to be more accurately interpolated. The use of more BBs allows more accurate interpolation and ultimately better 3D accuracy, but x-ray shadows from more BBs also obstructs the surgeon from being able to visualize the anatomy of interest on the x-ray image.

Figure 17:
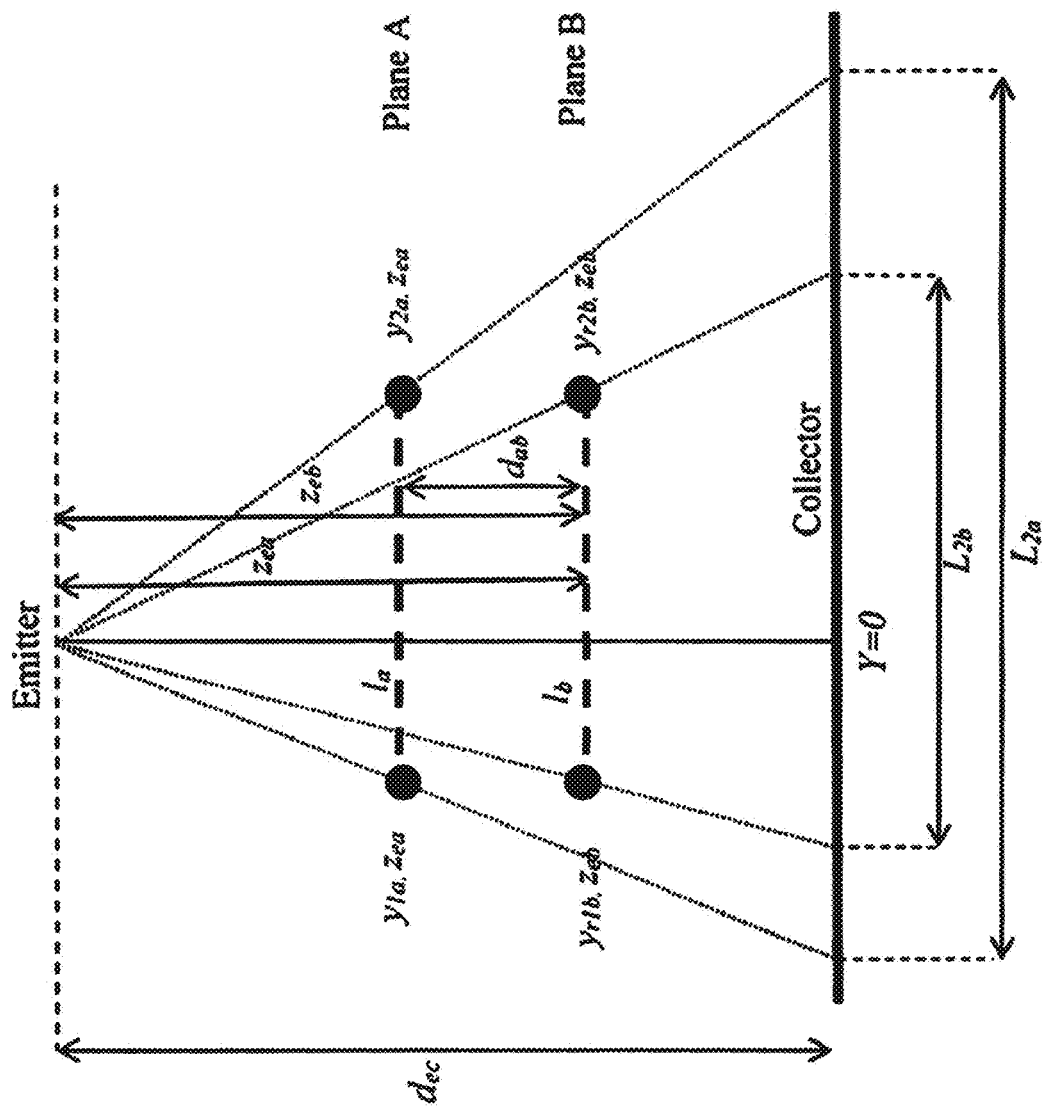
FIG. 17 illustrates key dimensions looking at a plane perpendicular to the collector plate's plane, and with BBs in the field of view whose shadows appear on the collector plate.

Implicit assumptions are that the positions of the collector plate and emitter source are known in 3D during both shots. For instance, the collector plate may have a tracking array attached and its 3D position would therefore be directly tracked. It may also be possible to place a tracker on the emitter. However, there are disadvantages to doing so, mainly that the tracking field needs to be very large to observe both trackers, where the distance between collector and emitter may typically be on the order of one meter. Tracking systems such as optical trackers may only have a tracking field less than one cubic meter. Additionally, the emitter could be positioned out of view for some clinically typical x-ray shots. The emitter source location could instead be calibrated relative to the collector array, but the extrapolated accuracy in defining the emitter location may be low with a large distance between collector and emitter and the different amounts of sag when the fluoroscope is oriented differently. Alternatively, the emitter source distance and direction relative to the collector may be calculated from fluoroscopic images of two parallel planes of BBs with known spacing $d_{ab}$, 1712, such as is shown in FIG. 14 and FIG. 17. The equations provided in Equation 1 hold based on the geometry 2000 depicted in FIG. 17.

$$\frac{kL_{2a}}{d_{ec}} = \frac{l_a}{z_{ea}}$$ Equation 1

$$\frac{kL_{2b}}{d_{ec}} = \frac{l_b}{z_{ec}} = \frac{l_b}{(Z_{ea} + d_{ab})}$$

where, $d_{ec}$ is the distance from emitter to collector in mm;

k is the scaling factor to convert pixel coordinates on the fluoro output to mm;

$l_a$ is the distance laterally in mm within Plane A between BB1a and BB2a;

$l_b$ is the distance laterally in mm within Plane B between BB1b and BB2b;

$y_{1a}$ is the distance in mm from the central beam laterally to BB1a;

$y_{1b}$ is the distance in mm from the central beam laterally to BB1b;

$y_{2a}$ is the distance in mm from the central beam laterally to BB2a;

$y_{2b}$ is the distance in mm from the central beam laterally to BB2b;

$z_{ea}$ is the distance in mm from the emitter to Plane A (BB1a and BB2a);

$z_{eb}$ is the distance in mm from the emitter to Plane B (BB1b and BB2b);

$d_{ab}$ is the distance in mm longitudinally between Plane A and Plane B;

$L_{2a}$ is the distance in pixel coordinates between the shadows of the BBs in Plane A on the collector; and $L_{2b}$ is the distance in pixel coordinates between the shadows of the BBs in Plane B on the collector.

Solving for $d_{ec}$ Produces $$\frac{d_{ec}}{k} = \frac{d_{ab}L_{2a}L_{2b}}{l_b L_{2a} - l_a L_{2b}}$$ Equation 2

Therefore, if the spacing between the planes is known and the spacing between the BBs is known, the distance from the emitter to collector can be determined through image processing of an x-ray image containing these BBs. Note that FIG. 17 indicates that the distances between shadows of two adjacent BBs in two planes are measured. In practice, the distances between several pairs of BBs on the x-ray image may be measured and these distances averaged. Additionally, FIG. 17 shows the distances between BBs on Plane A and Plane B as being the same, however, their physical distances may differ and is accounted for by $l_a$ and $l_b$ in the equations. In practice, it may be desirable to make the BBs offset rather than spaced the same and aligned to prevent their projections from partially obscuring each other.

This method for defining the position of the emitter relative to the collector makes use of the two parallel plates in defining the direction of the emitter as well as the distance. With the registration fixture mounted to the collector, the direction from emitter to collector is assumed to be perpendicular to the plane of the collector and the planes containing BBs. If this assumption is untrue, the projections of BBs from the near and far field planes will not be symmetrically overlaid on x-ray images. For a given amount of angular deviation of the x-ray plane from the BB planes, the amount of offset of BB shadows from a symmetrical projection is proportional to the distance between BB planes, with larger plane separation manifesting as larger lateral displacements of the projections on the x-ray images. Through geometry, the lateral offsets of BB shadows can be used to determine accurately the actual orientation of the BB planes relative to the collector plane and therefore the position of the emitter in 3D, or used to manually or automatically adjust the orientation of the registration fixture on the image intensifier until BB planes and collector plate are truly coplanar.

The scaling factor k is present in the above equation, but this factor is necessary for subsequent 3D to 2D mapping of the 3D coordinates of a generalized point. In general, to map a 3D point with coordinates x, y, z onto a 2D x-ray image that has the X and Y axes of the image aligned with the x and y axes of the Cartesian coordinate system, Equation 3 holds.

$$X = x\left(\frac{d_{ec}}{kz}\right)$$ Equation 3

$$Y = y\left(\frac{d_{ec}}{kz}\right)$$

Where X is the coordinate axis of the 2D x-ray image aligned with the Cartesian X-axis, Y is the coordinate axis of the 2D x-ray image aligned with the Cartesian y-axis, and z is the Cartesian axis perpendicular to the x-ray image.

If two fluoroscope shots are taken at different orientations up to 90 degrees apart, such as one common clinical anteroposterior shot and one common clinical lateral shot, then (X1, Y1) could be defined as the x-ray coordinates of a point (x, y, z) as the point appears on an x-ray image 1 (e.g., an anteroposterior image). The Cartesian coordinates of the point in a local coordinate system aligned with that x-ray plane could be defined as (x1, y1, z1). Similarly, (X2, Y2) could be defined as the x-ray coordinates of the same point as it appears on an x-ray image 2 (e.g., a lateral image). The Cartesian coordinates of the point in a local coordinate system aligned with that x-ray plane could be defined as (x2, y2, z2). Because a tracking system may be used to detect the 3D position of the x-ray collector while the fluoroscope is in each orientation, the transformation T12 from Cartesian coordinate system 1 to Cartesian coordinate system 2 is known, with T12 being a standard 4×4 transformation matrix as is commonly used in the field. There is therefore a unique solution that results in Equation 4.

$$X_1 = x_1\left(\frac{d_{ec}}{kz_1}\right)$$

$$Y_1 = y_1\left(\frac{d_{ec}}{kz_1}\right)$$

$$X_2 = x_2\left(\frac{d_{ec}}{kz_2}\right)$$

$$Y_2 = y_2\left(\frac{d_{ec}}{kz_2}\right)$$

Equation 4 and $$\begin{bmatrix} x_2 \\ y_2 \\ z_2 \end{bmatrix} = T_{12} \begin{bmatrix} x_1 \\ y_1 \\ z_1 \end{bmatrix}$$

Note that the two coordinate systems are each oriented with their z-axis perpendicular to each x-ray plane, the origin of their z-axis at each x-ray plane, and the origins of their x and y axes at the center of the x-ray plane. The direction of x and y relative to the x-ray planes may be arbitrary. By tracking the locations of the x-ray planes in 3D, using for example 3D optical tracking, the transformation from the first to the second 3D coordinate system ($T_{12}$) can be determined.

A method for defining the 3D Cartesian coordinate system associated with two fluoroscopic views may assume that the BBs are projected uniformly onto the image intensifier. However, distortion is commonly associated with images obtained from fluoroscopes, such as pincushion distortion, s-distortion, and the like. These types of distortion may be corrected using image processing before applying the methods described herein. Distortion correction may make use of the fact that the BBs are arranged in a symmetrical pattern on the registration device. Therefore, the x-rays projected through the known symmetrical pattern should create an image with matching symmetry. Spacing between BBs and alignment of rows of BBs may be determined through image processing and compared to the expected projections of the BBs. Algorithms commonly known in image processing such as affine transformations and the like may be used to force the projected x-ray image to match the known and expected symmetry. Since the same correction may also be applied to anatomical images on the x-rays, the resulting x-ray images should represent undistorted projections and should allow valid calculation of registration as described herein.

Figure 18:
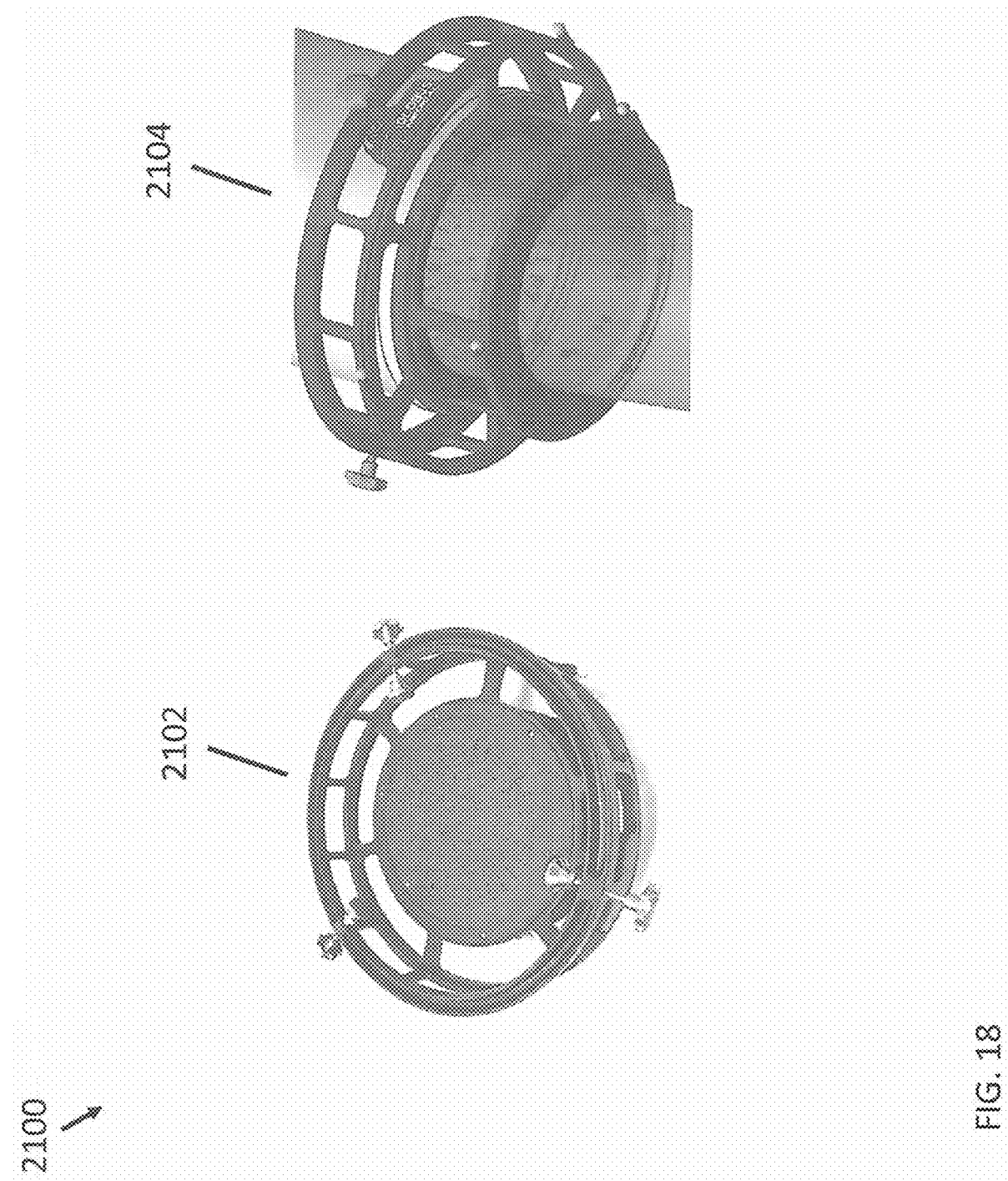
FIG. 18 illustrates a bb pattern on the two parallel plates and the design of the fixture, which mounts to the image intensifier of a fluoroscopy unit.
Figure 19:
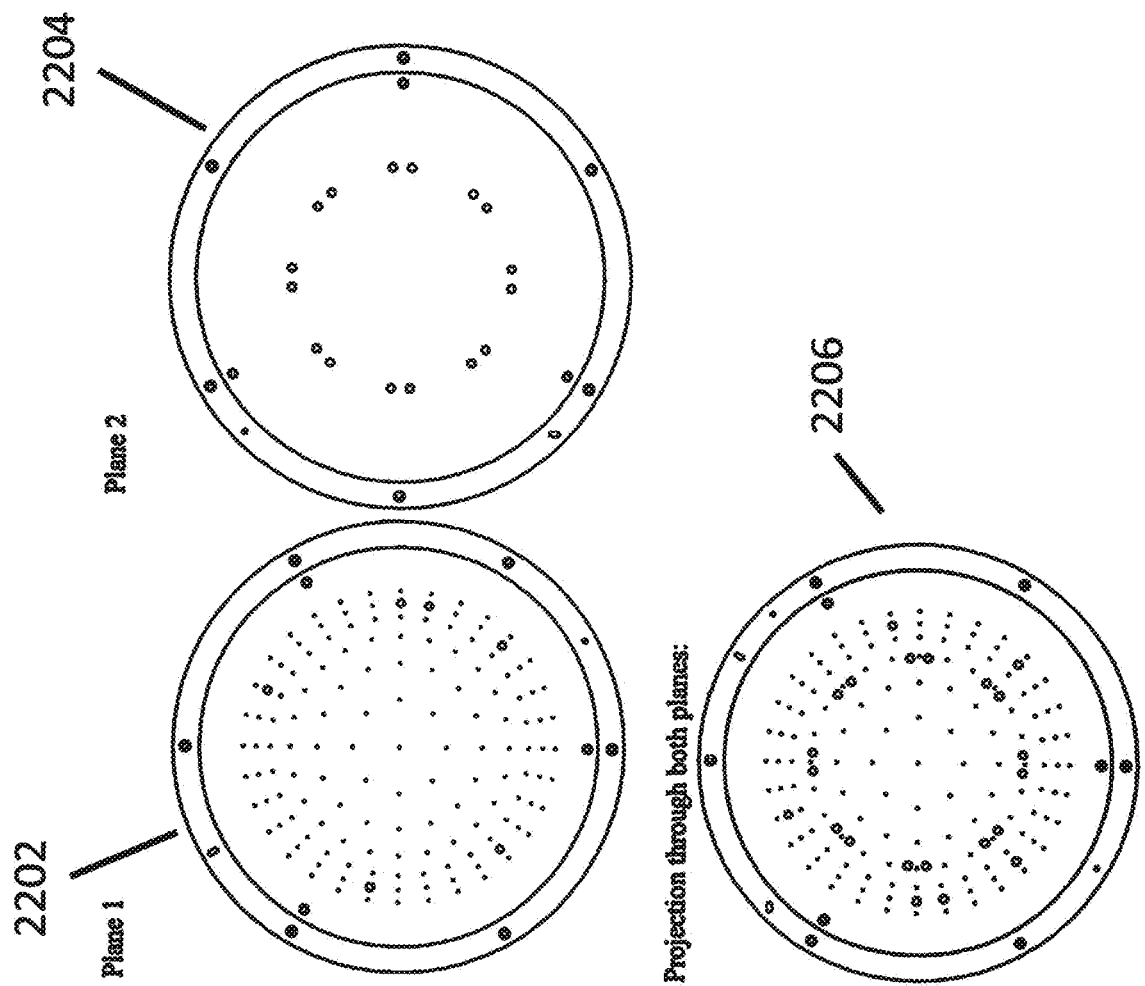
FIG. 19 illustrates a BB pattern for a registration fixture.

In embodiments, the symmetrical pattern used for correcting distortion could be a square pattern as depicted in FIG. 16, a radially symmetrical pattern in which BBs are distributed in a polar coordinate system about the center of the image, where BBs share common radii and azimuth angles, or any suitable pattern as depicted in the fixture in FIGS. 18 and 19. As long as the pattern of actual BBs embedded in the registration fixture is known, the corresponding shadows of the BBs on x-ray images can be predicted and distortion correction applied to force the image to match the expected pattern.

The process of 2D to 3D mapping of images relies on the correct interpretation of direction on the x-ray image. For example, if a 2D x-ray image is an anteroposterior image, it must be known if the 2D image represents a shot with emitter anterior and collector posterior or a shot with emitter posterior and collector anterior. Additionally, since fluoroscopic images are commonly round, there must be a way to precisely determine from the BB shadows which direction points left, right, up or down. The fixture's plane of BB's may provide information for alignment correction, such as using BB's located closest to the x-ray collector to provide information to orient the x-ray image rotationally and also with regard to reflection, e.g., the BB pattern may determine whether the positive z direction extends off the front or back of the visible plane. In embodiments, the fixture may contain an outer ring of large BBs that are arranged so it uniquely identifies aspects of alignment, such as the rotation and flip of the image. The pattern of BBs for identifying orientation and/or flip may be chosen based on the ability of the pattern to provide a unique combination of image rotation and flip and on the ability of pattern to provide redundant BB s for increased reliability of detection. Redundant BBs may be important because it is possible that not all BBs would be visible on any given x-ray shot due to obstruction of the BB shadow from tools or implants, or poor x-ray penetration through parts of the image.

In embodiments, a ring of BBs of varying spacing around the perimeter of a standard circular fluoroscopic image may be employed, such as illustrated in FIG. 19 where the shadows of the perimeter BBs form a bit code (e.g., 32 bit code). In embodiments, a first plane 2202 with a first array of points and a second plane 2204 with a second array of points may be projected to form a combined image 2206. Code lengths should be selected to enable the spacing of the BBs to be far enough apart so there is a small chance that an error in detecting a BB's location could result in it falsely falling into an adjacent bit location while still providing enough information to be robust to missing bits. If only a subset of the existing BBs is detected, with a few of the BB shadows not detectable, comparison of the subset against a known template may provide the correct image orientation and flip regardless of which BBs are missing. If a subset with a greater number of BBs missing is detected, an algorithm may determine the correct image orientation and flip. In embodiments, knowing the limitations of the algorithm, the system may require that a certain minimum number of BBs is detected before allowing the algorithm to proceed.

In embodiments, orientation matching may utilize a point match algorithm (e.g., the Kabsch point match algorithm) or other suitable point match algorithm that assumes both point sets are scaled the same. The algorithm may then determine the transformation between two point sets, where one point set comes from the orientation BB detection and the other point set comes from a fixture 3D model. The fixture's orientation markers may then be projected into image space. Since both point sets need to be scaled the same, the algorithm tests a range of projection scaling to find the best match. Once the best match is found the transform is scaled appropriately, and the algorithm assigns point correspondence between the detected image markers and the physical fixture markers. The resulting transform can then be applied to the image to rotate and/or flip it to produce alignment with the fixture.

Figure 20:
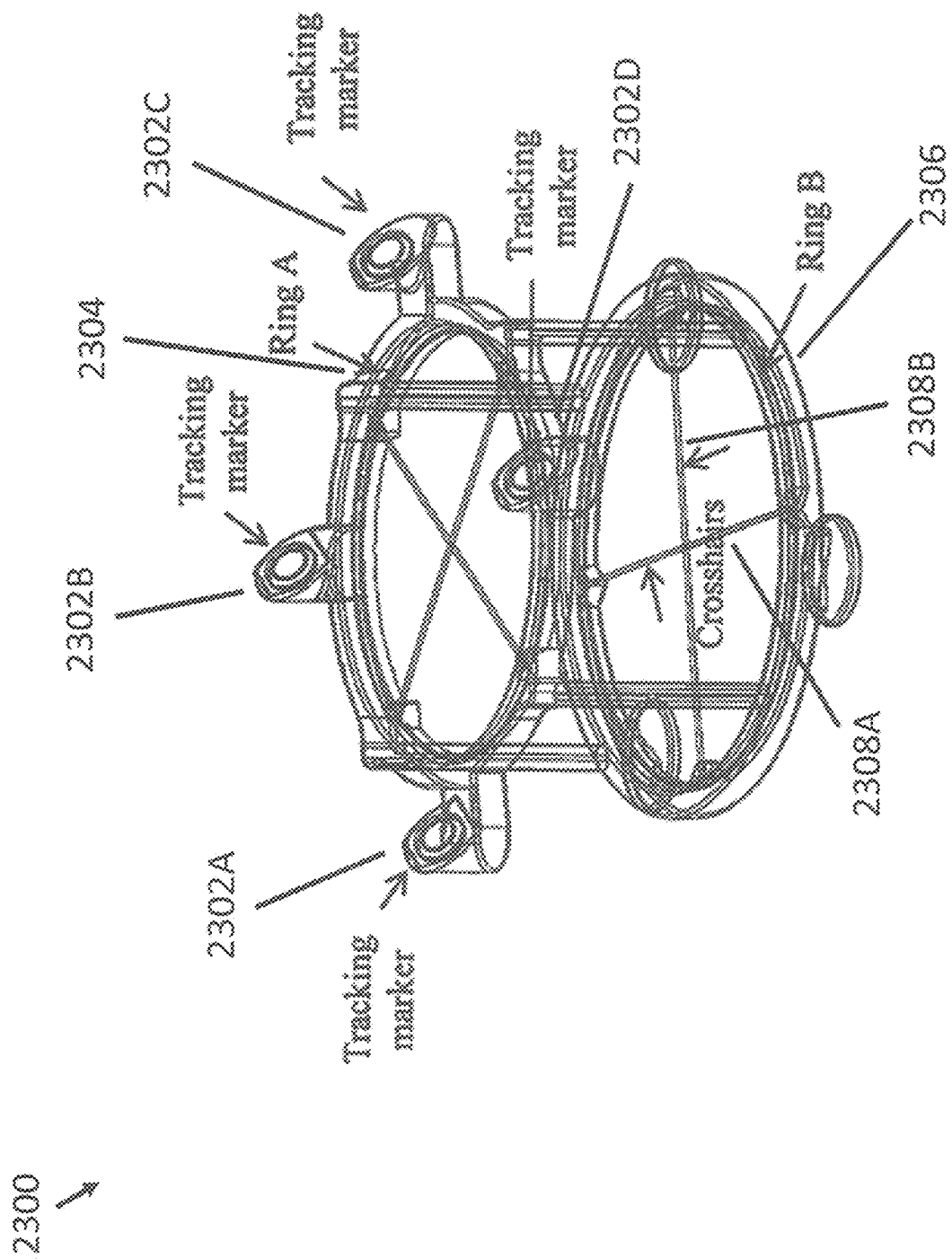
FIG. 20 illustrates a fluoro registration fixture constructed from parallel rings with crosshairs.

Ring Registration Fixture:

As an alternative to an array of BBs to establish orientation, it is possible to use rings or other shapes, such as formed from radio-opaque materials such as metal wire, as fiducials in a registration fixture. Referring to FIG. 20, a ring registration fixture 2300 is illustrated with two parallel rings 2304 and 2306 of the same or different diameters (e.g., between 50-300 mm), are positioned concentrically in parallel planes spaced apart (e.g., spaced apart by 50-300 mm). To facilitate identification of the centers of the rings 2304 and 2306, the rings may also have one or more crosshairs 2308A and 2308B formed of wire or other radio-opaque material of the same or different diameter as the rings themselves. Some desirable features of the rings include rings that are exactly circular, that their crosshairs pass through the exact center so that diameters of the projected ellipses and crosshair intersection points are accurate, and the like. Additionally, it may be desirable that the cross-section of a ring be circular instead of flattened, so that if the ring is at an angle relative to the x-ray image it is properly projected. Possible methods for fashioning rings include welding or otherwise adhering segments of wire, rapid prototyping (3D printing) using a radiopaque building material, etching in the same manner as is used for fabrication of printed circuit boards, and the like.

Figure 21:
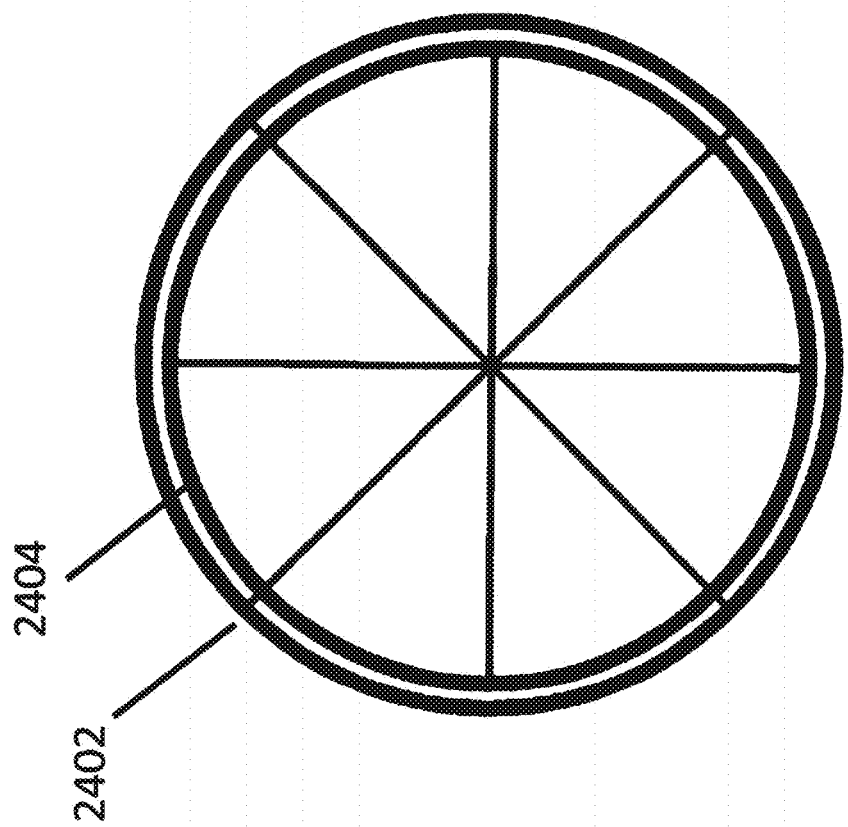
FIG. 21 illustrates an appearance of a ring registration fixture on an x-ray when the x-ray collector is parallel with the planes of the rings and the rings are concentric with the x-ray collector.
Figure 22:
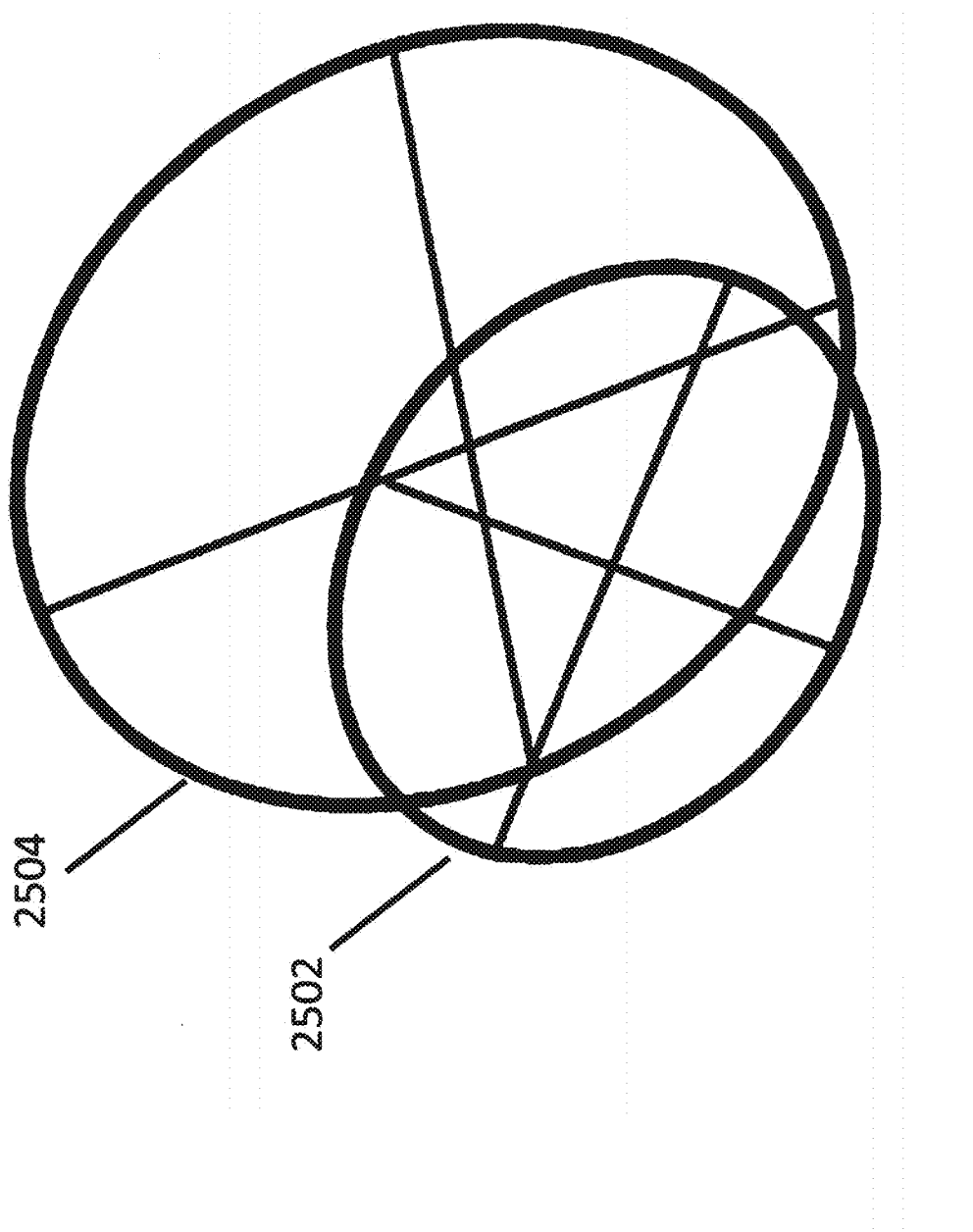
FIG. 22 illustrates a theoretical appearance of a ring registration fixture on an x-ray when the fixture is at a severe angle relative to the collector plate and the rings.

When an x-ray image is taken of the ring registration fixture 2300 while centered on a collector plate, it should appear as two concentric circles 2402 and 2404, such as shown on FIG. 21. If the x-ray image is taken while the ring registration fixture 2300 is not parallel to the collector plate or centered, it would appear as two ellipses 2502 and 2504 such as illustrated in FIG. 22.

In addition, tracking markers 2302A-D may be used as references for ring positioning of the ring registration fixture 2300 in 3D, such as utilizing an array of optical markers, a magnetic sensor, or other like 3D tracking method. For reference it may be convenient to define a local coordinate system on the registration fixture 2300. For example, a reference local coordinate system may have its origin at the center of the ring that is closer to the x-ray emitter, with the second (e.g., parallel) ring closer to the collector, and the x-axis and y-axis may be coincident with the crosshairs that identify the first ring's center, where the z-axis is coincident with the vector joining the centers of the two rings.

In embodiments, mapping points from 3D to 2D using a ring registration fixture may utilize vectors through known points on both rings that are created to form a conical pattern, where this pattern is then used to interpolate vectors through regions of interest.

In embodiments, a sequence of common transformations may be applied (i.e., rotations, translations, magnification), such as with the transformation parameters estimated from features on the images. As an example, consider a 3D coordinate system based on a two-ring fixture such that the coordinate system is centered on a first ring nearer to the emitter as a near field ring and a second ring that is nearer to the collector as a far field ring. In this example, near and far field rings may be the same diameter, where in order to map a point from this coordinate system to the coordinate system of the collector plate, a number of transformations may be applied.

Figure 23:
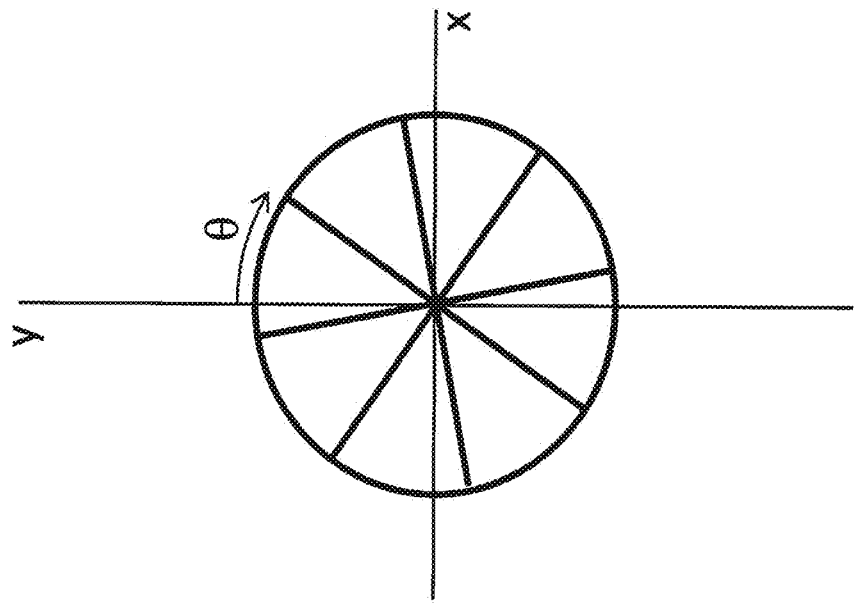
FIG. 23 illustrates a transformation step for rotation by θ about z in a coordinate system mapping process.
Figure 24:
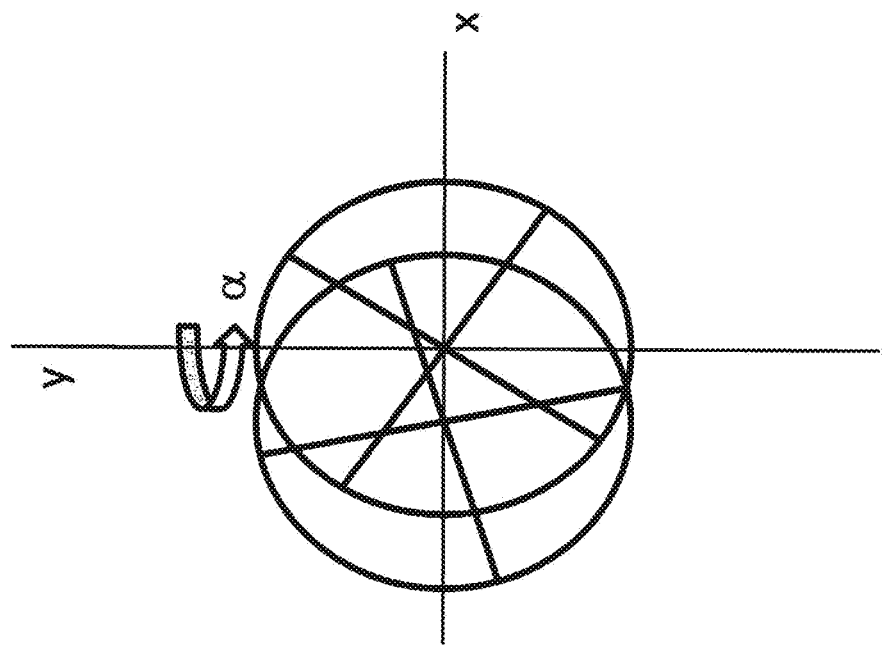
FIG. 24 illustrates a transformation step for rotation about y by α in a coordinate system mapping process.
Figure 25:
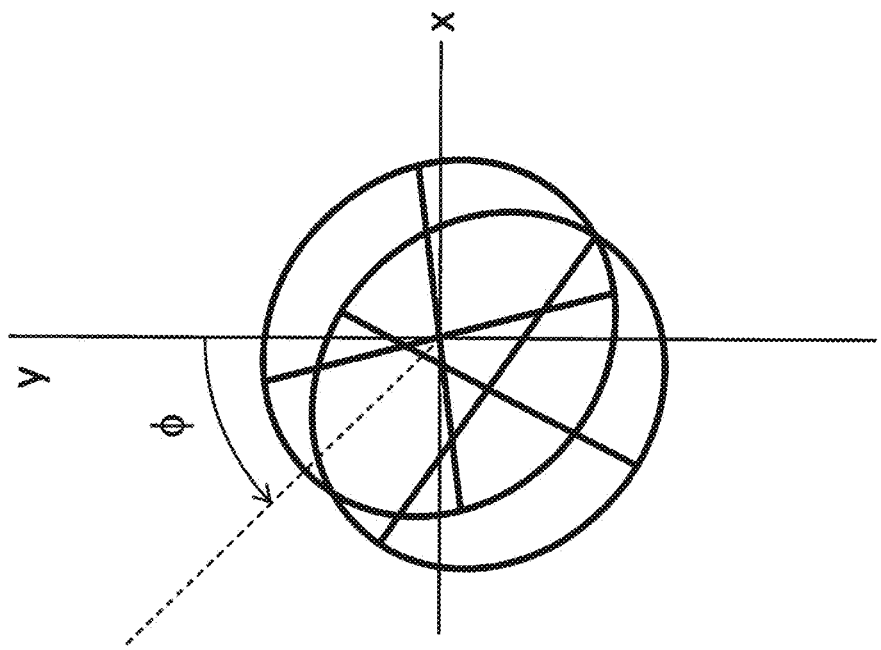
FIG. 25 illustrates a transformation step for rotation in plane to match a radiograph's perspective in a coordinate system mapping process.
Figure 26:
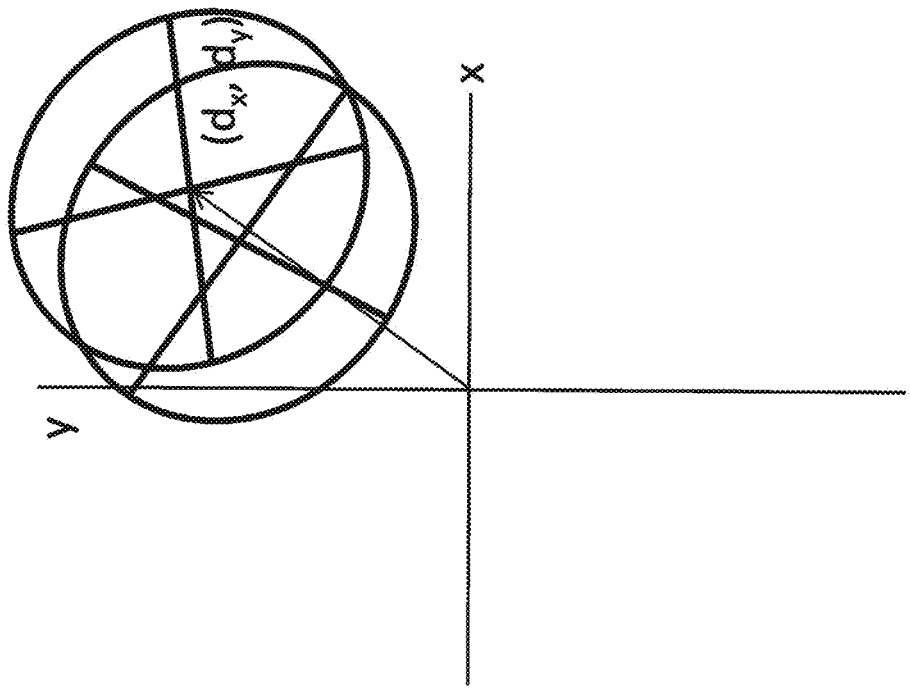
FIG. 26 illustrates a transformation step for displacement from a coordinate system center by dx, dy in a coordinate system mapping process.
Figure 27:
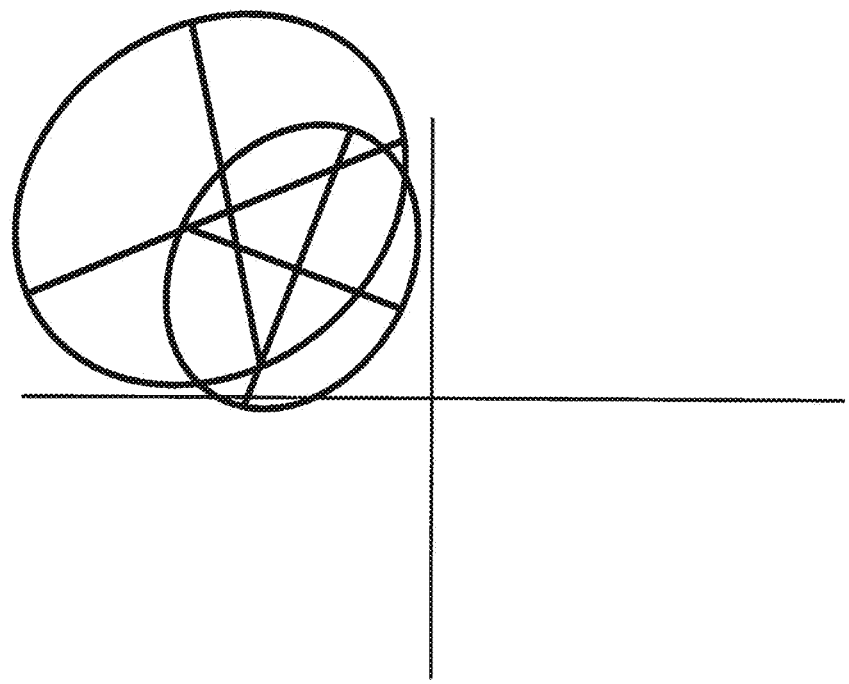
FIG. 27 illustrates a transformation step of magnification according to parallax in a coordinate system mapping process.

A non-limiting example set of illustrative transformations are depicted in FIGS. 23-27. FIG. 23 depicts a transformation step 1 rotating by θ about z (e.g., θ is the angle allowing subsequent rotation a to occur about y). Note that in this figure, the rings are viewed in 3D without parallax, and so the near and far field rings exactly overlap in the starting orientation. FIG. 24 depicts a transformation step 2 rotating about y by α. Note that rotation occurs about the center of the near field ring (e.g., the ring closer to the emitter). FIG. 25 depicts a transformation step 3 rotating in plane to match the radiograph's perspective (e.g., finding the angle in the x-y plane off of y to get to the actual axis of rotation instead of using y axis as the axis of rotation for incidence angle α). FIG. 26 depicts a transformation step 4 displacing from coordinate system center by dx, dy. FIG. 27 depicts a transformation step 5 magnifying according to parallax. In this example, with step 5 complete, the x-y plane represents the points mapped to the 2D plane. In step 5 magnification occurs according to Equation 3.

In this example, on the final image the near field ring appears more magnified than the far field ring since points on the near field ring have larger z values than the points on the far field ring. Additionally, rotation of the rings in x-y plane may appear different depending on how far the rings are from x, y=0, 0.

Thus, to go from a point in 3D that is specified in a coordinate system attached to the ring registration fixture to a point in 2D on the x-ray plane, a sequence of transformations is applied where there are five unknowns: θ, α, φ, dx, and dy. It is possible to use image processing to estimate these five unknowns from the rings themselves. Therefore, once these five parameters are defined and registration is established, any new point specified as x, y, z in the reference coordinate system may be directly mapped to the x-ray image coordinates.

Figure 28:
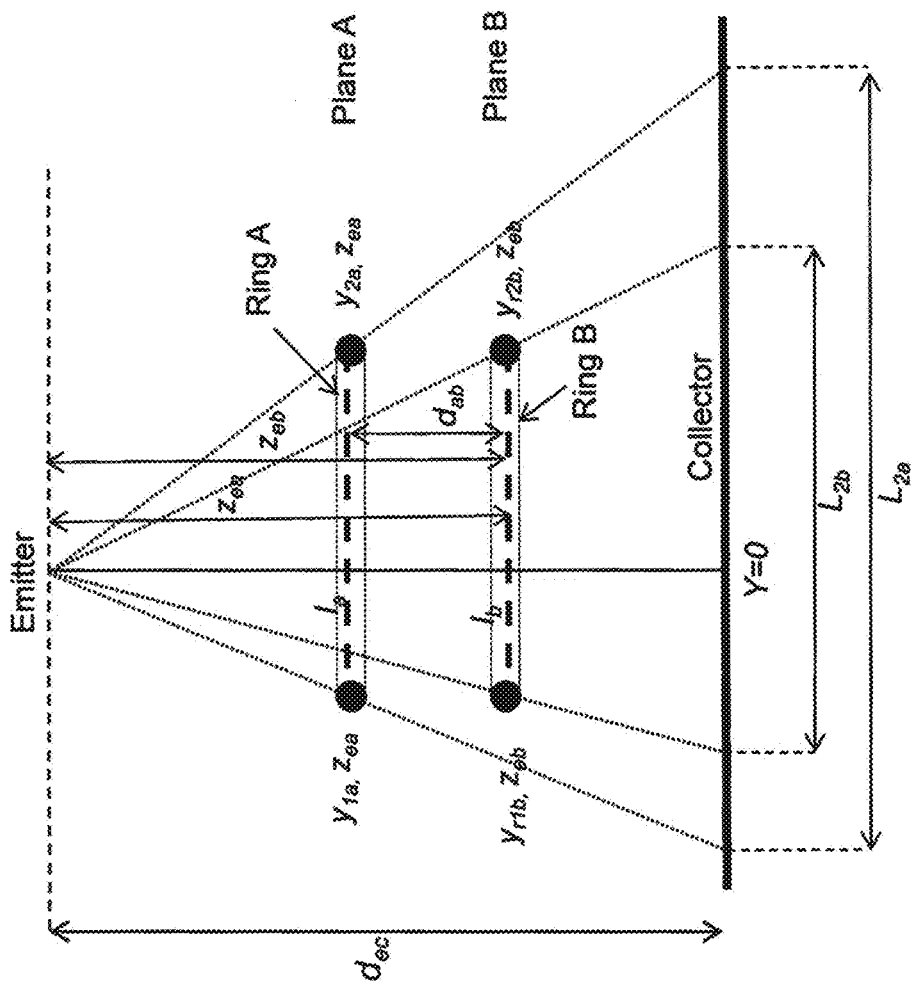
FIG. 28 illustrates a schematic of key dimensions looking at a plane perpendicular to a collector plate's plane with rings parallel to the collector in the field of view whose shadows appear on the collector plate.

For many of the calculations for determining the five parameters from the images, the ratio of $d_{ec}/k$ is needed, as was described respect to the BB fixture. This ratio may be determined similarly from an x-ray image taken of the rings while oriented parallel to the collector plate. FIG. 28 illustrates a schematic of key dimensions looking at a plane perpendicular to the collector plate's plane, and with rings parallel to the collector in the field of view whose shadows appear on the collector plate. Based on FIG. 28, the following equations can be written to determine $d_{ec}/k$:

$$\frac{d_{ec}}{k} = \frac{d_{ab}L_{2a}L_{2b}}{l_b L_{2a} - l_a L_{2b}} \qquad \text{Equation 5}$$

Where
$d_{ec}$ is the distance from emitter to collector in mm;
k is the scaling factor to convert pixel coordinates on the fluoro output to mm;
$l_a$ is the diameter of Ring A;
$l_b$ is the diameter of Ring B;
$y_{1a}$ is the distance in mm from the central beam laterally to the edge of Ring A;
$y_{1b}$ is the distance in mm from the central beam laterally to the edge of Ring B;
$y_{2a}$ is the distance in mm from the central beam laterally to opposite edge of Ring A;
$y_{2b}$ is the distance in mm from the central beam laterally to opposite edge of Ring B;
$z_{ea}$ is the distance in mm from the emitter to Plane A (to Ring A);
$z_{eb}$ is the distance in mm from the emitter to Plane B (to Ring B);
$d_{ab}$ is the distance in mm longitudinally between Plane A and Plane B;
$L_{2a}$ is the diameter in pixel coordinates of the shadow of Ring A on the collector; and
$L_{2b}$ is the diameter in pixel coordinates of the shadow of Ring B on the collector.

Figure 29:
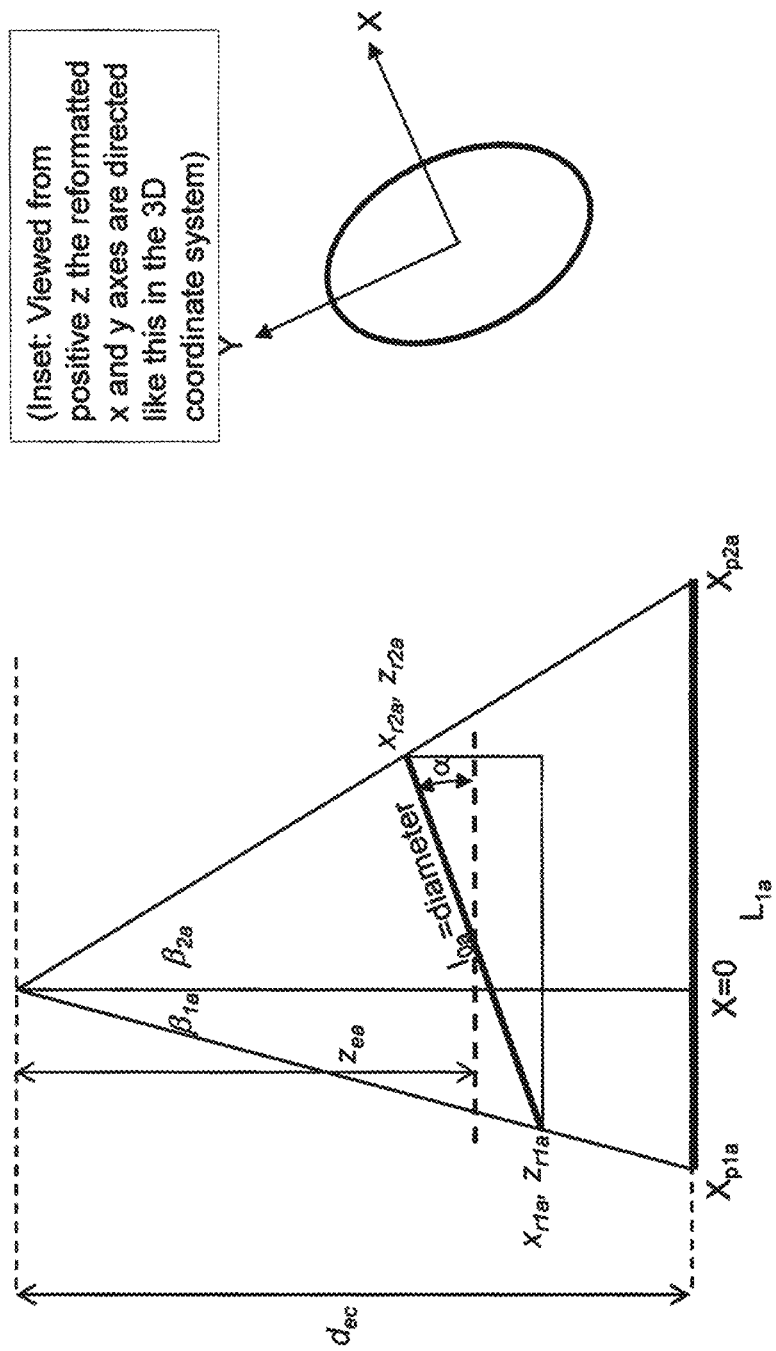
FIG. 29 illustrates a view across a ring that is at an arbitrary incidence angle to the collector plane from a perspective looking across the ring plane, where the ring plane is in and out of the page.

Non-limiting examples of how the five unknowns (θ, α, φ, dx, and dy) may be determined will now be described.
Calculating Angle of Incidence α:

Consider a conical beam hitting a plane of arbitrary angle relative to the cone and projecting the image on to the collection plate, as viewed from the perspective depicted in FIG. 29, where the view across a ring is at an arbitrary incidence angle to the collector plane from a perspective looking across the ring plane. The ring plane is in and out of the page as shown in the inset, where the view is from positive z and the reformatted x and y axes are directed as shown in the 3D coordinate system. In this example, the distance from the top of the cone (e.g., the x-ray emitter) to the collector on which the image is perceived, $d_{ec}$, is fixed. Subscript 'a' is used because there is a second ring parallel to this one with the same incidence angle $\alpha$ and diameter $l_{0b}$, this second ring having subscript 'b'. Note that the coordinate systems of the plate and the 3D space above it are positioned such that the center of the 2D image is at $X_p=0$ and the center of the 3D space is also at $x_r=0$.

Based on FIG. 29, the following equations hold:

$$\frac{kX_{p1a}}{d_{ec}} = \frac{x_{r1a}}{z_{r1a}}$$  Equation 6

$$\frac{kX_{p2a}}{d_{ec}} = \frac{x_{r2a}}{z_{r2a}}$$

Figure 30:
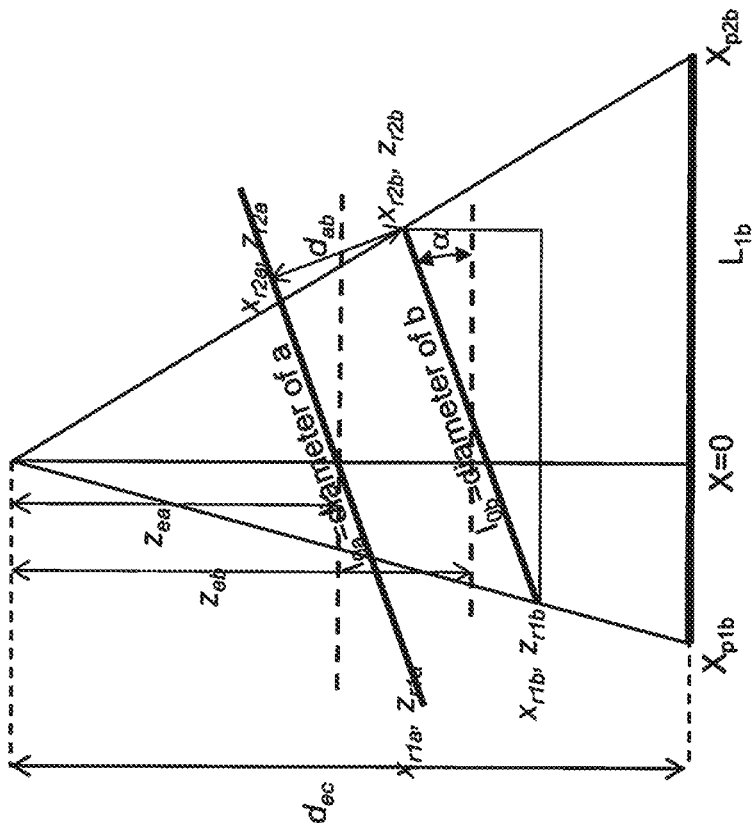
FIG. 30 illustrates a view across a pair of concentric rings that are at an arbitrary incidence angle to the collector plane from a perspective looking across a ring plane, where the ring plane is in and out of the page.

Referring to FIG. 30, now consider a fixture with two parallel rings of different diameters. The parameters $z_{ea}$ and $z_{eb}$ represent the distance in z direction from the emitter to the midpoint (intersection of crosshairs) of each ring. FIG. 30 illustrates a view across a pair of concentric rings that are at an arbitrary incidence angle to the collector plane from a perspective looking across the ring plane, where the ring plane is in and out of the page (see inset). Based on FIG. 30, the following equation holds:

$$\cos\alpha = \frac{z_{eb} - z_{ea}}{d_{ab}}$$  Equation 7

Figure 31:
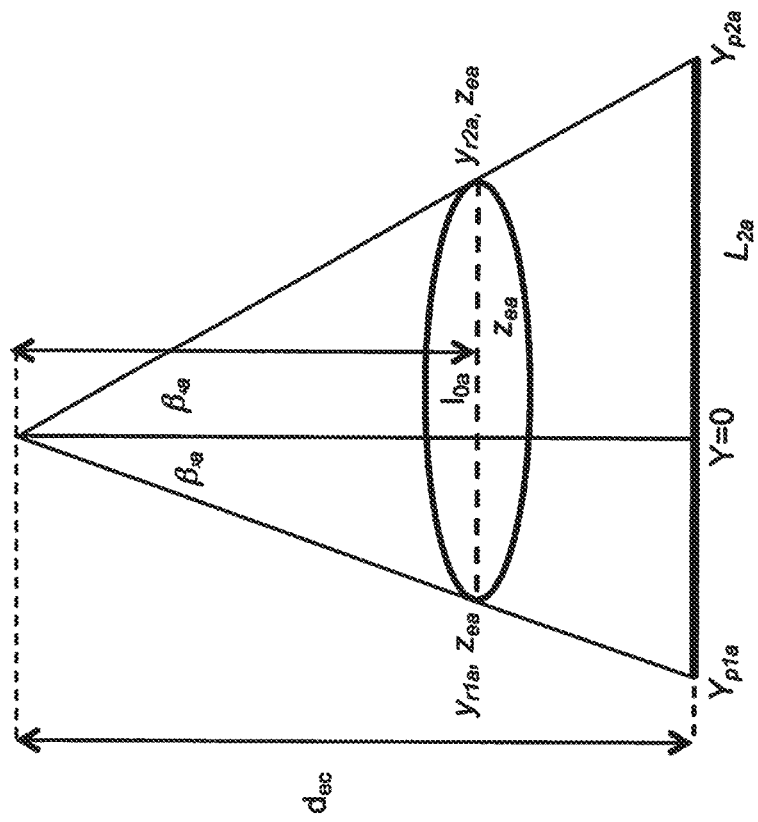
FIG. 31 illustrates a view of a ring at an arbitrary incidence angle from a rotated perspective.

To solve for $z_{ea}$ (and $z_{eb}$) consider the other perspective of the ring, as viewed across the widest part as illustrated in FIG. 31, which provides a view of the ring at an arbitrary incidence angle from a perspective rotated 90 degrees from that of FIG. 29 and FIG. 30. From this follows:

For ring a $$\frac{l_{0a}}{z_{ea}} = \frac{kL_{2a}}{d_{ec}}$$  Equation 8

For ring b $$\frac{l_{0b}}{z_{eb}} = \frac{kL_{2b}}{d_{ec}}$$  Equation 9

Or $$z_{ea} = \frac{d_{ec}l_{0a}}{kL_{2a}}$$  Equation 10

$$z_{eb} = \frac{d_{ec}l_{0b}}{kL_{2b}}$$

Plugging into equation 7, $$z_{eb} - z_{ea} = d_{ab}\cos\alpha$$  Equation 11

$$\frac{d_{ec}l_{0b}}{kL_{2b}} - \frac{d_{ec}l_{0a}}{kL_{2a}} = d_{ab}\cos\alpha$$

-continued $$\frac{d_{ec}l_{0b}L_{2a} - d_{ec}l_{0a}L_{2b}}{kL_{2a}L_{2b}} = d_{ab}\cos\alpha$$

$$\alpha = \cos^{-1}\left[\frac{d_{ec}(l_{0b}L_{2a} - l_{0a}L_{2b})}{kd_{ab}L_{2a}L_{2b}}\right]$$

Where $L_{2a}$=widest diameter of elliptical projection of ring a in pixel coordinates;

$L_{2b}$=widest diameter of elliptical projection of ring b in pixel coordinates;

$d_{ec}$=distance in mm from emitter to collector;

$d_{ab}$=shortest distance in mm from ring a to ring b;

k=conversion factor for pixels to mm;

$l_{0a}$=known actual diameter of ring a in mm; and $l_{0b}$=known actual diameter of ring b in mm.

Figure 32:
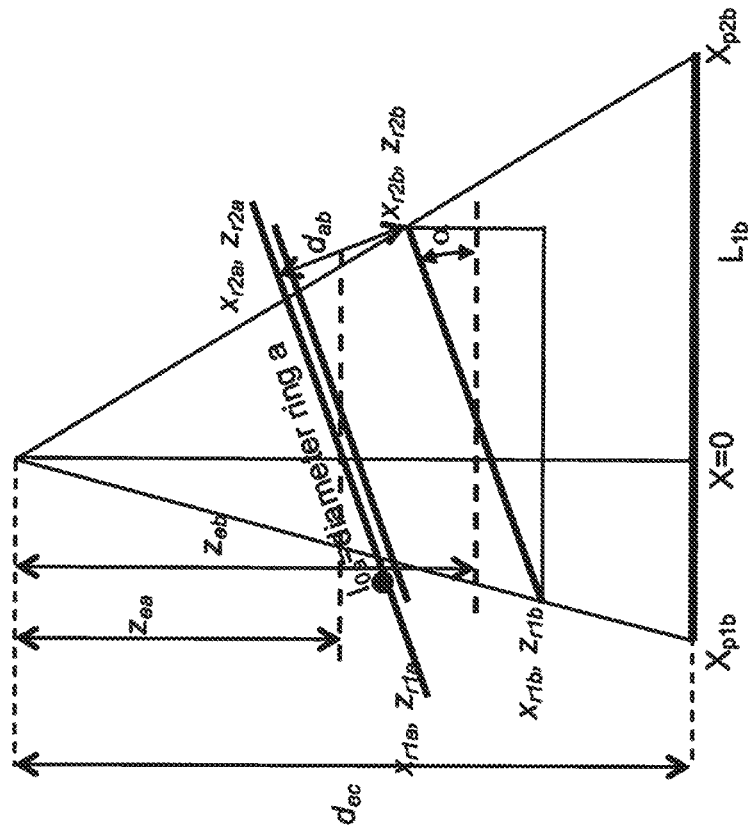
FIG. 32 illustrates a view of a pair of rings at an arbitrary incidence angle.

Equation 11 dictates that the widest and narrowest projections of the rings be measured, and slight variations may lead to discrepancies in $\alpha$. It is useful to seek an equation based on displacement of the ring centers instead, which is less sensitive to error. If the lower ring is "magnified" to match the known ratio of diameters of upper and lower rings (e.g., ratio of 1 if the rings are the same diameter), it would be the same as if the ring were moved up in the vertical direction (z direction) since scaling is done for values of each point on the ring in the coordinate system where ring points are offset from zero. FIG. 32. Illustrates a view of a pair of rings at an arbitrary incidence angle from the same perspective as FIG. 29. If the far field ring is magnified to match the magnification of the near field ring, it would be equivalent to physically moving the ring up the z-axis until $z_{ea}=z_{eb}$.

This z position becomes the z position of the major axis of both ellipses. Image processing enables the scaling of the image of the far field ellipse about the center of the image until the far field ellipse diameter relative to the near field ellipse diameter match the expected ratio. For example, if the far field ring and near field ring physically have identical diameters, the x-ray projected far field ellipse will appear smaller than the near field ellipse. Points on the far field ellipse may then be scaled so that a new image of the far field ellipse would have the same diameter as the near field ellipse. In particular, the only point that needs to be scaled may be the center of the far field ellipse, as defined by the intersection of the far field ring's crosshairs. With the far field ellipse scaled and the near field ellipse not scaled, the offset in the centers of the ellipses represents the measurement in image coordinates of the side opposite in a triangle with hypotenuse equal to the distance between rings. At this z position, the hypotenuse may be determined in image coordinates, where it is the distance between rings times the ratio of near field ellipse major axis over the near field ring diameter (or times the ratio of the scaled far field ellipse major axis over the far field ring diameter, which is by definition of the scaling factor the same). With the side opposite and hypotenuse, $\alpha$ can be found with an arcsine function.

$$\alpha = \sin^{-1}\left(\frac{D_{cab}}{L_{2a}\left(\frac{d_{ab}}{l_{0a}}\right)}\right)$$  Equation 12

Where:
- $D_{cab}$=distance in image coordinates between the center of the un-scaled near field; ellipse and the scaled far field ellipse;
- $L_{2a}$=diameter of near field ellipse in image coordinates measured in the direction of the axis of rotation (roughly equivalent to projected ellipse's major axis);
- $l_{0a}$=diameter of near field ring in mm; and
- $d_{ab}$=distance between rings in mm.

Figure 33:
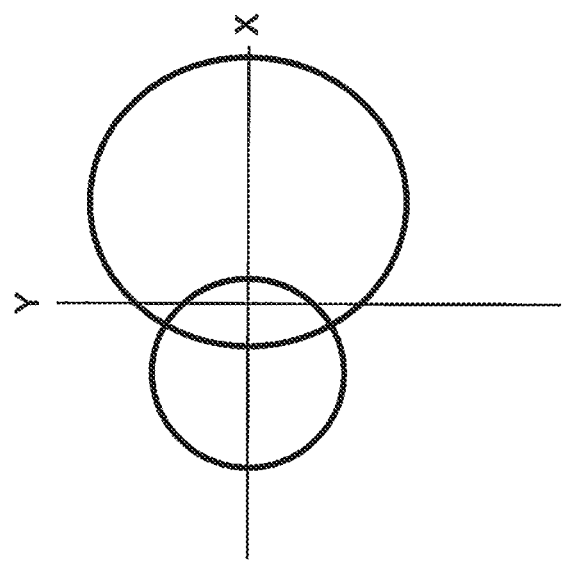
FIG. 33 illustrates a modeled appearance on an x-ray (with parallax) of two circular rings with an incidence angle of α=20° occurring about the y-axis.
Figure 34:
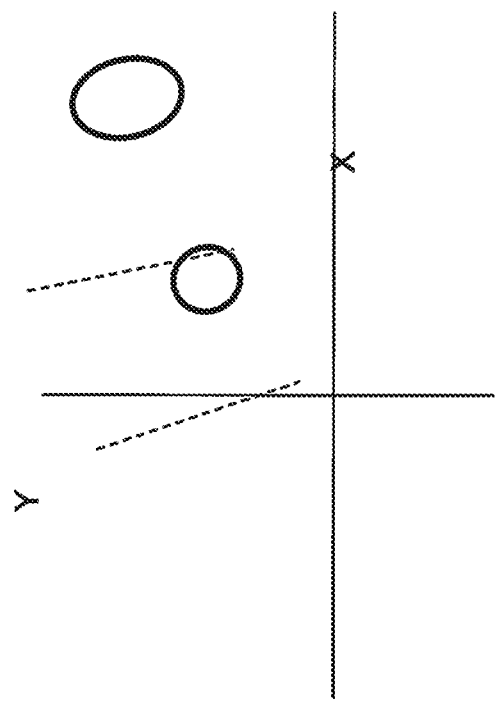
FIG. 34 illustrates a modeled appearance on an x-ray (with parallax) of two parallel circular rings with an incidence angle of α=24.5° occurring about the y-axis, where both rings are offset from the center of the x-ray, and the long axis of both ellipses appears to be angled visibly relative to the y-axis

Calculating Azimuth Angle ϕ:

It might appear that the azimuth angle ϕ (the angle required to put the axis of rotation for ring incidence on the y-axis) is just the angle relative to the major axis of one of the ellipses. For example, FIG. 33 depicts a modeled appearance on an x-ray (with parallax) of two circular rings with an incidence angle of α=20° occurring about the y-axis. The long axis of both ellipses appears to be oriented in line with the y-axis and therefore an azimuth angle of ϕ=0° would be expected. Seemingly, the orientation of the long axis of either or both ellipses can be assessed using image processing and used for determining θ. However, it can be seen that the long axes of the ellipses do not accurately reflect the azimuth angle if the ring positions are offset from the center of the image. In the example depicted in FIG. 34, which was generated from numerical data, there is clear discrepancy in the orientations of the major axes of the two ellipses. In FIG. 34 a modeled appearance is depicted on an x-ray (with parallax) of two parallel circular rings with an incidence angle of α=24.5° occurring about the y-axis. Both rings are offset from the center of the x-ray. The long axis of both ellipses appears to be angled visibly relative to the y-axis; additionally, the long axis of the larger ellipse appears to have a different azimuth angle than that of the smaller ellipse. In this case, the azimuth angle is known to be ϕ=0° but image processing would not have correctly given this angle.

An additional consideration is that for small angles, it may be difficult to accurately assess the exact direction in which the diameter is largest, thus a method for using the orientation of the major axis of an ellipse to find θ may produce a lower accuracy result. In embodiments, a method using the length of the major axis of an ellipse should produce better results.

Figure 35:
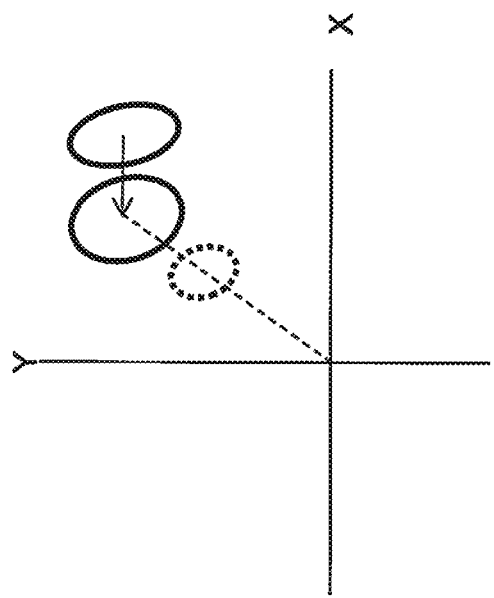
FIG. 35 illustrates a modeled appearance on an x-ray (with parallax) of two parallel circular rings with an incidence angle of α=24.5° occurring about the y-axis, where both rings are offset from the center of the x-ray, and the far field ellipse has been scaled about the center of the image until the near and far field ellipse are equal in their long axis.

In the scaling exercise described in reference to FIG. 32, it can be seen that magnification is equivalent to moving the entire ring up the z-axis. Therefore, if the far field ring is scaled appropriately, the two elliptical ring images will represent a projection at the same z coordinate of the near and far field rings. If the center of the near and far field rings are at the same z coordinate, then the vector connecting them in x and y represents the path of the axis of rotation. The actual axis of rotation should be perpendicular to this path and also in the x-y plane. Therefore, the axis of rotation may be extracted through image processing by first scaling the far field ring center then tracing the path connecting the centers of the far field and near field ring images. In an illustration, FIG. 35 depicts a modeled appearance on an x-ray (with parallax) of two parallel circular rings with an incidence angle of α=24.5° occurring about the y-axis. Both rings are offset from the center of the x-ray. The far field ellipse has been scaled about the center of the image until the near and far field ellipses are equal in their long axis. The azimuth angle is known to be ϕ=0° (i.e., rotation about the y axis—see FIG. 24) which is the correct result after scaling has been performed.

The angle θ is the angle of the near field vertical crosshair relative to Y or horizontal crosshair relative to X after accounting for the perspective. Thus, finding the locations of the intersections of crosshairs with the ellipses and then applying an inverse incidence angle would give the intersection points in a flat plane, allowing the angle θ to be determined from an arctangent of the x, y coordinates of the crosshair intersection point.

Note that it is important to know which crosshair is aligned with X or Y and which direction of a crosshair points to +X or +Y. This information can be determined from additional features on the fixture that appear on x-ray images, such as a BB or wire near the reference crosshair's positive axis or any other suitable feature.

The offset position dx, dy is the offset of the x, y coordinate of the center of the near field ring. This point can be directly tracked based on the tracker on the fixture and the corresponding point seen on the resulting x-ray. This point can serve as a registration check. That is, if a navigated probe is pointed at the center of the near field ring, an image of a probe with its tip at the projected ellipse's crosshair intersection should be seen.

If the registration fixture is attached very precisely to the image intensifier, then several of the parameters referenced above go to zero. That is, the incidence angle α, axis of rotation reference ϕ, displacements dx and dy all go to zero, simplifying the registration process. Thus, as with the BB fixture, the locations of intersections of crosshairs and rings on x-rays could be used as adjustment tools instead of for extracting transformation parameters. That is, if an x-ray shows disparity in the intersections of the ring centers and edges, such as depicted in FIG. 21, the fixture could be adjusted manually or automatically on the image intensifier until the x-rays show centering, at which point the transformations would be simplified and mapping would be at its best accuracy.

Figure 36:
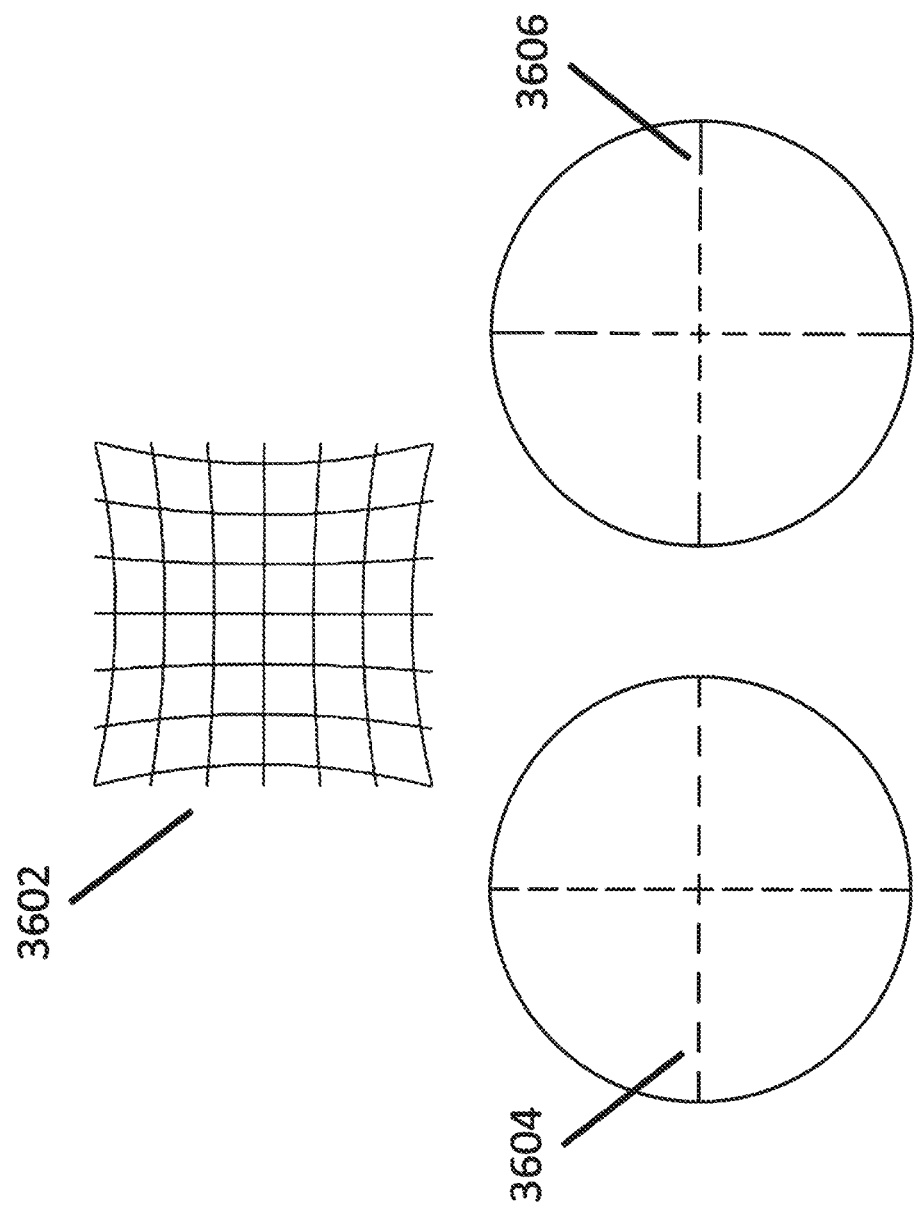
FIG. 36 illustrates a pincushion distortion.
Figure 37:
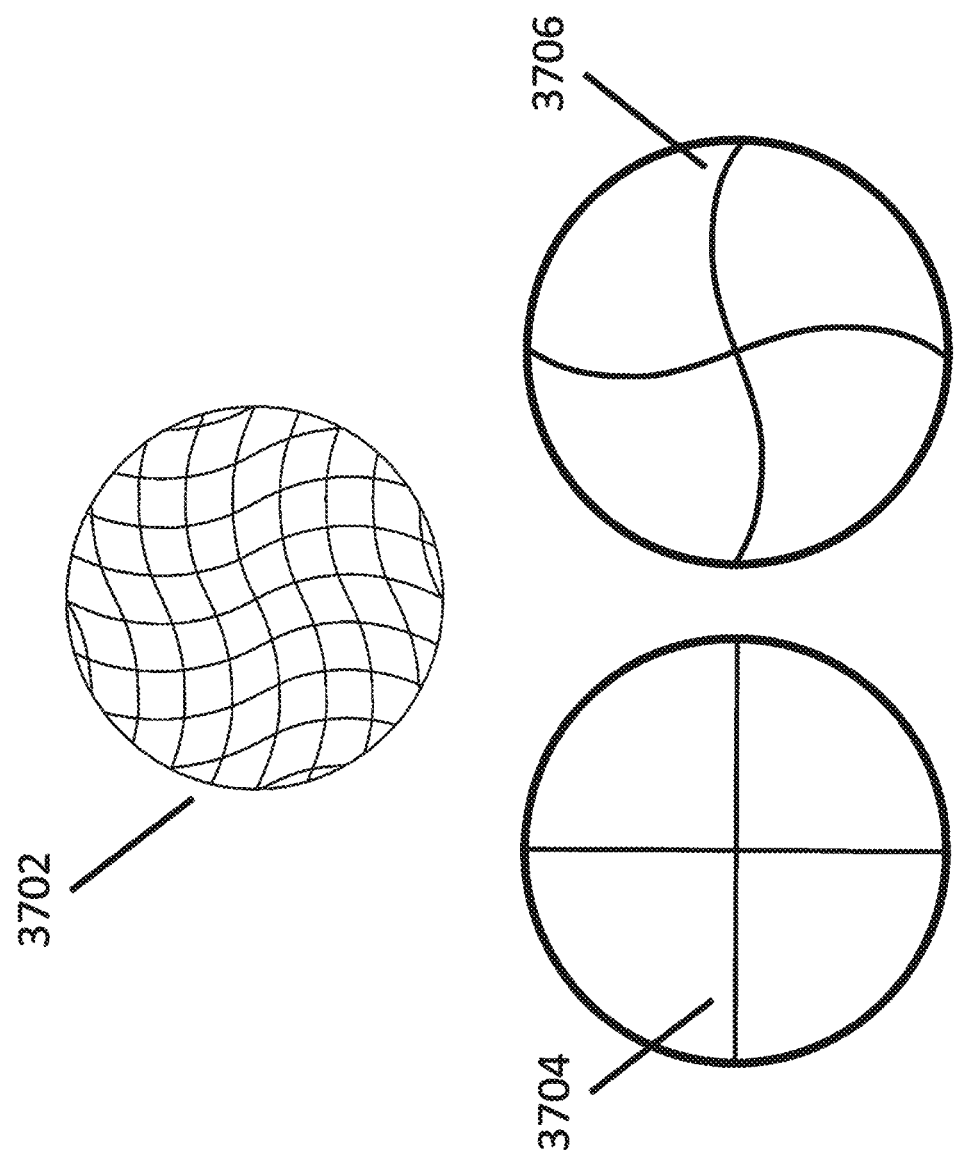
FIG. 37 illustrates an s-distortion.

When using rings in a registration fixture, correction of distortion may be achieved in a way that is similar to the correction applied for a BB fixture. In order for distortion correction to be effective, the crosshairs on the ring fixture require an additional feature in which evenly spaced markings are placed along each crosshair. These markings could be hatch marks, circles, gaps, or any such feature that appears on a visible projection on the x-ray image. Then, by considering both the linearity of the crosshairs and the spacing between indices on the crosshairs, pincushion and s-distortion may be accounted for and corrected. The FIGS. 36 and 37 show manifestations of pincushion and s-distortion on images when using ring fixtures. It is assumed that since pincushion distortion is radially symmetrical about the center of the image, it is only necessary to see one crosshair and the markings to account for the pincushion distortion and correct it, assuming the crosshair runs through the image center from one edge to the other. If pincushion distortion is not symmetrical at different angles, then additional crosshairs may be needed to assess the magnitude of pincushion in different directions.

FIG. 36 illustrates a pincushion distortion that might occur with a fluoroscope that would cause an x-ray that is shot through a square wire grid to appear as a pincushion distorted image 3602. For clarity, the pincushion pattern is shown more exaggerated than would be typical. In the lower part of the figure, a ring with crosshairs and evenly spaced gaps in the crosshairs is shown undistorted 3604 (left) and then with pincushion distortion 3606 (right). Note that the distortion has no effect on the ring but shows clearly on the spacing of the gaps in the crosshairs, with increasing spacing visible from the center outward to the ring. The magnitude of pincushion distortion is measured as the amount of increase in spacing between indices going from the center to the edge of the image. Similarly, barrel distortion would manifest as decreasing gaps in the crosshairs from image center to ring.

FIG. 37 illustrates an s-distortion that might occur with a fluoroscope that would cause an x-ray that is shot through a square wire grid to appear as is shown as an s-distorted image 3702. For clarity, the s-pattern is shown more exaggerated than would be typical. In the lower part of the figure, a ring with crosshairs is shown undistorted 3704 (left) and then with s-distortion 3706 (right). Note that the distortion has no effect on the ring but shows clearly on the crosshairs, which have taken on the s-shape. The magnitude of s distortion is measured from the amount by which the two crosshairs take on the s-shape.

3D Surgical Planning in 2D:

In the planning of medical procedures, such as in conjunction with a surgical robot platform, planning for placement of medical objects such as surgical screws may be provided in 3D based on the 2D images. For instance, in such planning a line segment drawn to represent a screw in one of the 2D views may be assumed to have a certain dimension into and out of the plane in which it is drawn (e.g., in the z dimension). It can also be assumed to have a certain starting and ending z coordinate into and out of the plane in which it is drawn. For example, if a pedicle screw is being planned on an anteroposterior and lateral x-ray image, an appropriate assumption for the z coordinates could be that the dimension of the screw on the lateral x-ray represents the maximum length of the screw. That is, the screw is not angled into or out of the plane and therefore the z coordinate of the tip and tail of the screw on the lateral image's local coordinate system are the same. The z coordinate, which is equal for tip and tail, could be assumed to be a value that would be appropriate to place the screw at the center of the anteroposterior image. That is, for the user selecting x- and y-coordinates in the lateral planar view, whatever z coordinate in the lateral image causes the screw image to appear at the center of the screen on the anteroposterior image would be used.

In embodiments, other means could be used for improved initial guesses on the unknown planning plane. For example, anteroposterior and lateral images could be used for planning, where the top of both images could be oriented to represent the rostral anatomical direction. If it is known through software prompting that the user is about to place the left screw by dropping it on the lateral image, the starting location of the screw on the anteroposterior image could be toward the left side of the screen, assuming left screen is left anatomical direction.

Once an initial position is dictated by the user in one view and guessed or otherwise specified by software in the other view, any subsequent repositioning of the screw in either view may be mapped to the other view through satisfying the forward mapping of the 3D coordinates to 2D. For example, the user may have defined the x, y, z coordinates of a screw's tip in a local Cartesian coordinate system associated with the registration fixture during a lateral x-ray. If, through software interactions, the user then selects and drags the representation of the screw tip, they must be moving the tip in the x-y plane of that Cartesian coordinate system, not in its z direction, since the x-y plane of the Cartesian coordinate system is parallel to the image plane. The x and y movements (with z movement=0) in that local coordinate system can be updated through the user interaction. Then, because the transformation between the local coordinate systems of the anteroposterior and lateral x-rays are known through tracking, the resulting x, y, z coordinates associated with the anteroposterior image's local coordinate system can also be updated, allowing mapping of the planned tip of the screw on to a new position in the anteroposterior image. Through a sequence of updating one image and then the other, the user can move the screw into a 3D position that is known relative to both tracked positions of the registration fixture and therefore known to the camera space and to the robot. The robot can then move to a position to allow the screw to be placed accurately.

Note that if the two coordinate systems of the images are perpendicular, one representing the anteroposterior and one representing the lateral x-ray, then movement of a planned representation of a screw tip or tail on the anteroposterior view in the rostrocaudal direction through software interaction would have the effect of causing the screw tip or tail representation to move rostrocaudally in the lateral view by the same amount. However, movement of the screw tip or tail left or right in the anteroposterior view may have no effect on the planned tip or tail position in the lateral image. Conversely, movement anterior or posterior of the screw tip or tail in the lateral image would have no effect on the screw tip or tail position in the anteroposterior image, but movement of the screw tip or tail position rostrally or caudally in the lateral image would cause the representation of the screw tip or tail in the anteroposterior image to change rostrocaudally by the same amount. If the two x-rays are not taken perpendicular, then movement left, right, up or down in one view of the planned screw tip or tail will cause the representation in the other view to move by at least some amount.

Although it has been described that two views are used for planning, such as one anteroposterior and one lateral x-ray, since the mapping of 3D to 2D can be created for any x-ray image it is possible to simultaneously display and update a plan on any number of x-ray images as long as the registration fixture's tracking information is acquired at the time the image is taken. For example, four images shot at 45-degree increments could be displayed in four quadrants of the screen and a planned screw could be registered to each view. Using software interactions to update the planned position in one view would cause the image in each of the other views to change.

Figure 38:
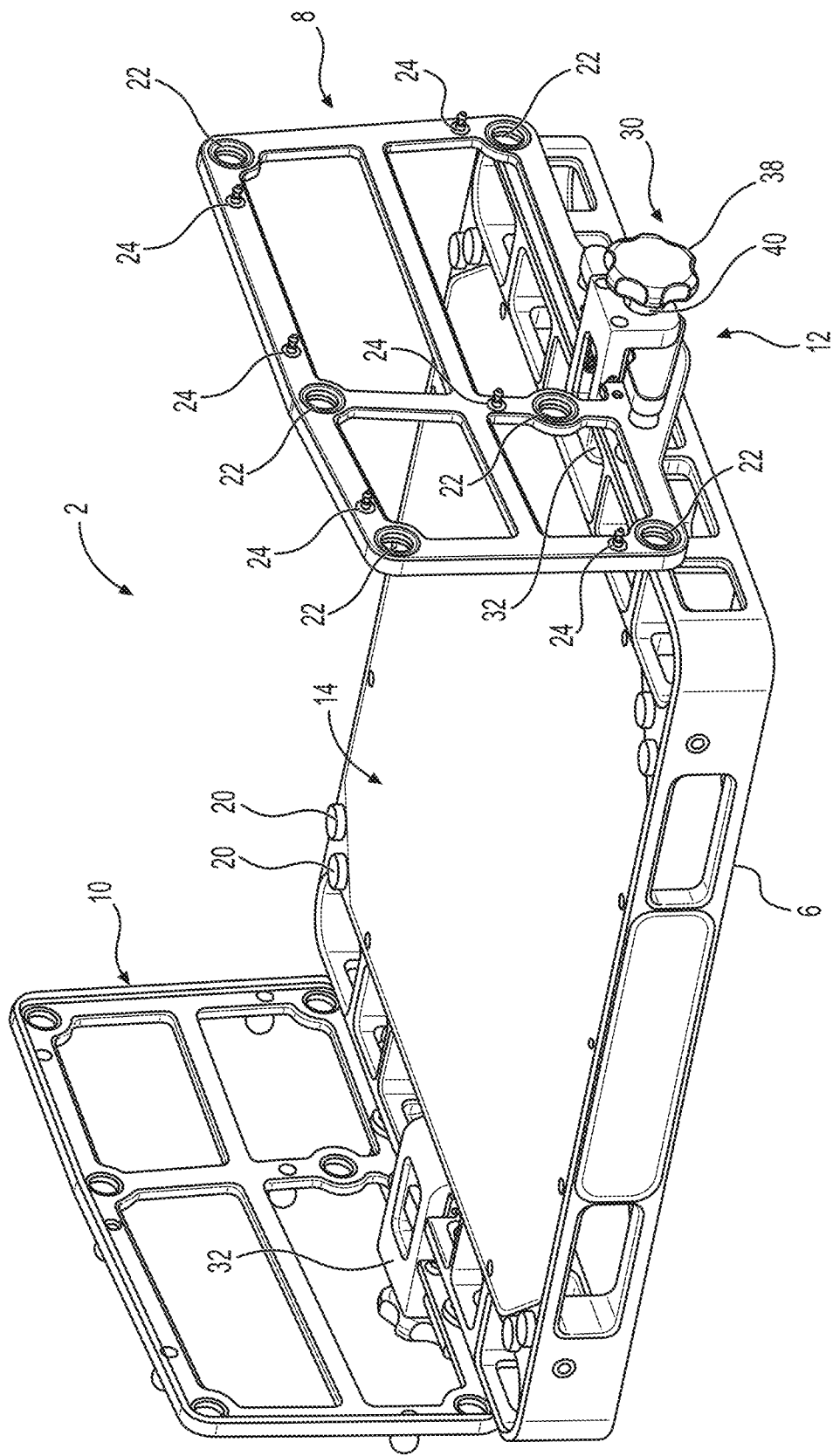
FIG. 38 is a perspective view of a novel registration fixture which is designed to be attached to a flat panel detector of a medical imaging device according to one aspect of the invention.
Figure 39:
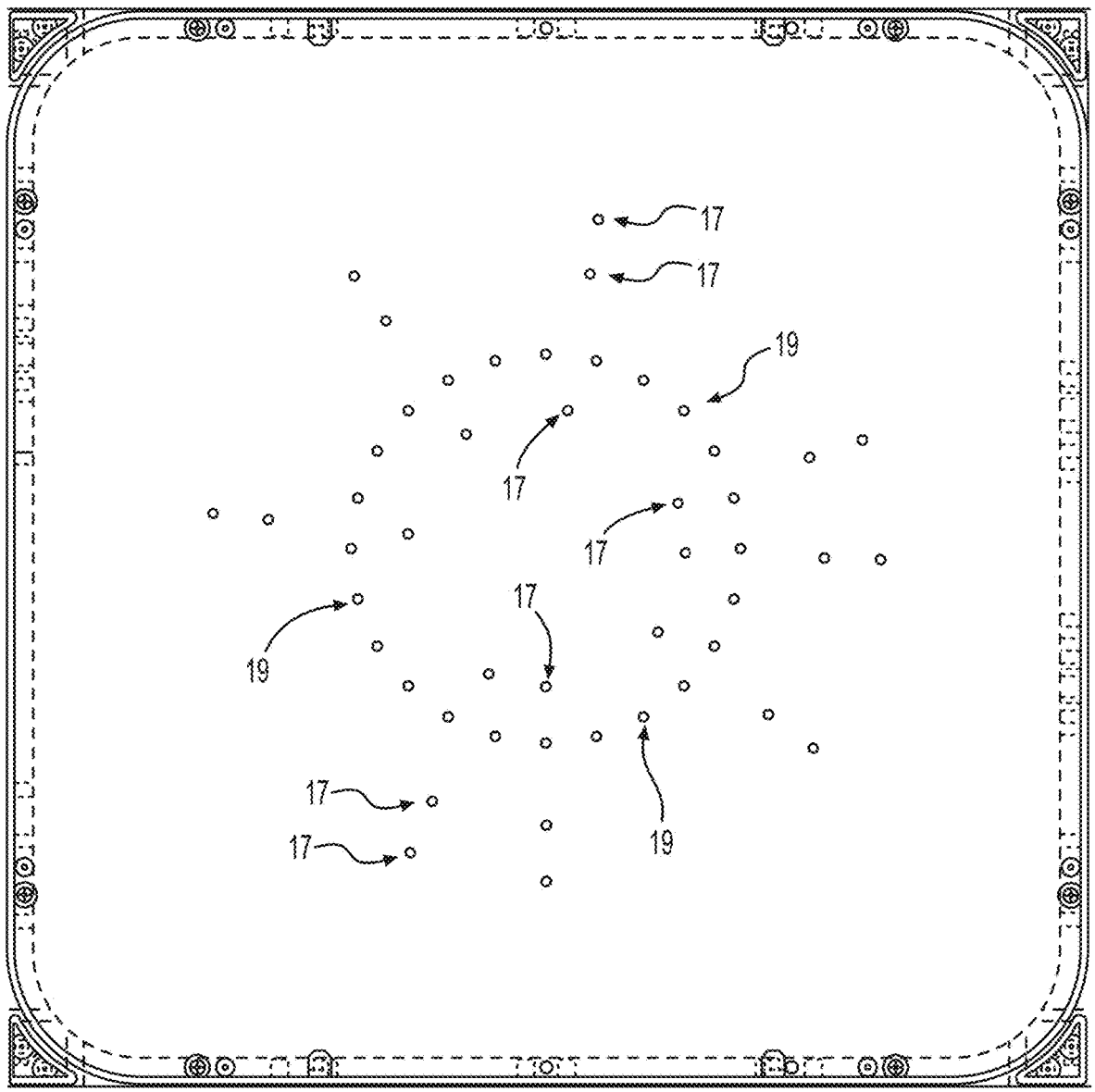
FIG. 39 is a plan view of a radiolucent plate having two sets of embedded radiopaque markers that are vertically spaced according to one aspect of the invention.

FIGS. 38-46 illustrate a novel registration fixture 2 which is configured for attachment to a flat panel detector 4 side of a medical imaging device, rather than the transmitter side. The registration fixture 2 of FIG. 38 is ideally suited for a medical imaging device that use a digital flat panel detector 4 on a C-Arm to take advantage of digital imaging technology, which include lower radiation dose and enhanced image quality as compared to an image intensifier based C-Arm systems.

The registration fixture 2 includes a base frame 6, first and second side frames 8,10 and a kinematic mount 12 that detachably attaches to the base frame 6. By definition, the kinematic mount restrains all six degrees of freedom of the side frames 8,10 relative to the base frame 6.

The base frame 6 is composed of an aluminum frame of minimized volume and weight, but can be fabricated from any of a number of reasonable cost, low density, high strength and stiffness materials.

A radiolucent plate 14 is attached to the base frame 6. In the embodiment shown in FIG. 39, the plate 16 includes two plates 14,16 that are vertically spaced from each other. An orientation plate 14 is positioned closer to the flat panel detector 4 and a registration plate 16 is positioned above the orientation plate.

Each plate is manufactured from a radiolucent material (e.g., carbon fiber, Rohacell foam, acrylic, ABS, or similar material) and houses embedded radiopaque markers 17,19 oriented in unique configurations for image processing and navigation purposes. In the embodiment shown, the radiopaque markers 17,19 are ⅛ inch stainless steel balls, but could be composed of any number of radiopaque materials and of a variety of geometries.

In one embodiment, the plates 14, 16 are mounted to a precision flat surface on the base frame 6 and a separation distance between the two plates is between 10 mm and 75 mm. In another embodiment, the range is between 25 mm and 50 mm, which may minimize obstruction within a surgical work area for the clinical team. Nevertheless, the plate separation distance can be increased or decreased to improve accuracy.

The orientation and registration plates 14, 16 are aligned with precision dowel pins 20 through a hole and slot configuration to achieve optimal plate to plate alignment precision. The hole, slot, pin configuration for the two plates are unique to prevent incorrect installation.

Figure 40A:
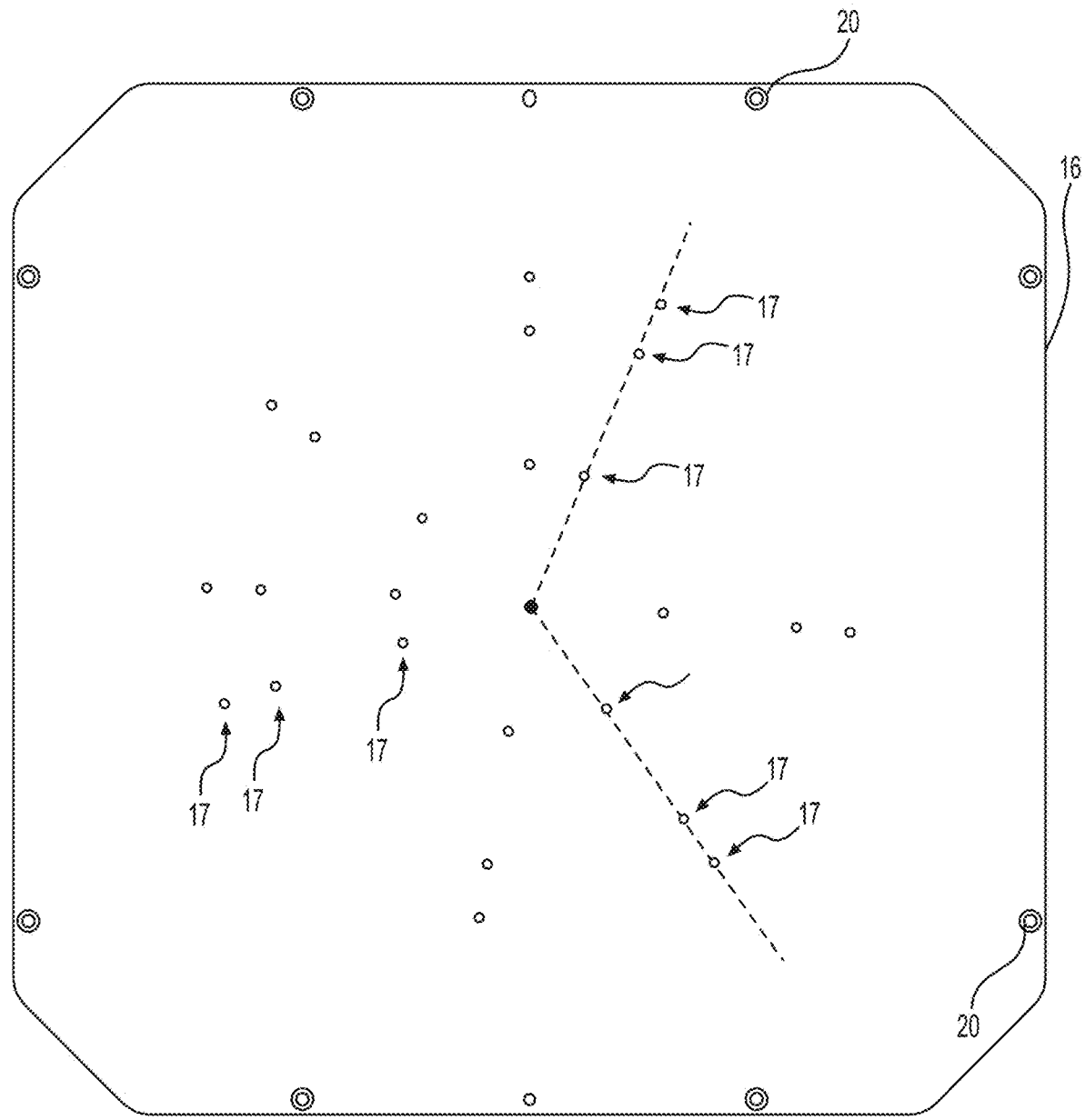
FIG. 40A is a plan view of a first plate of the radiolucent plate of FIG. 39 with a predetermined pattern of the radiopaque markers.
Figure 40B:
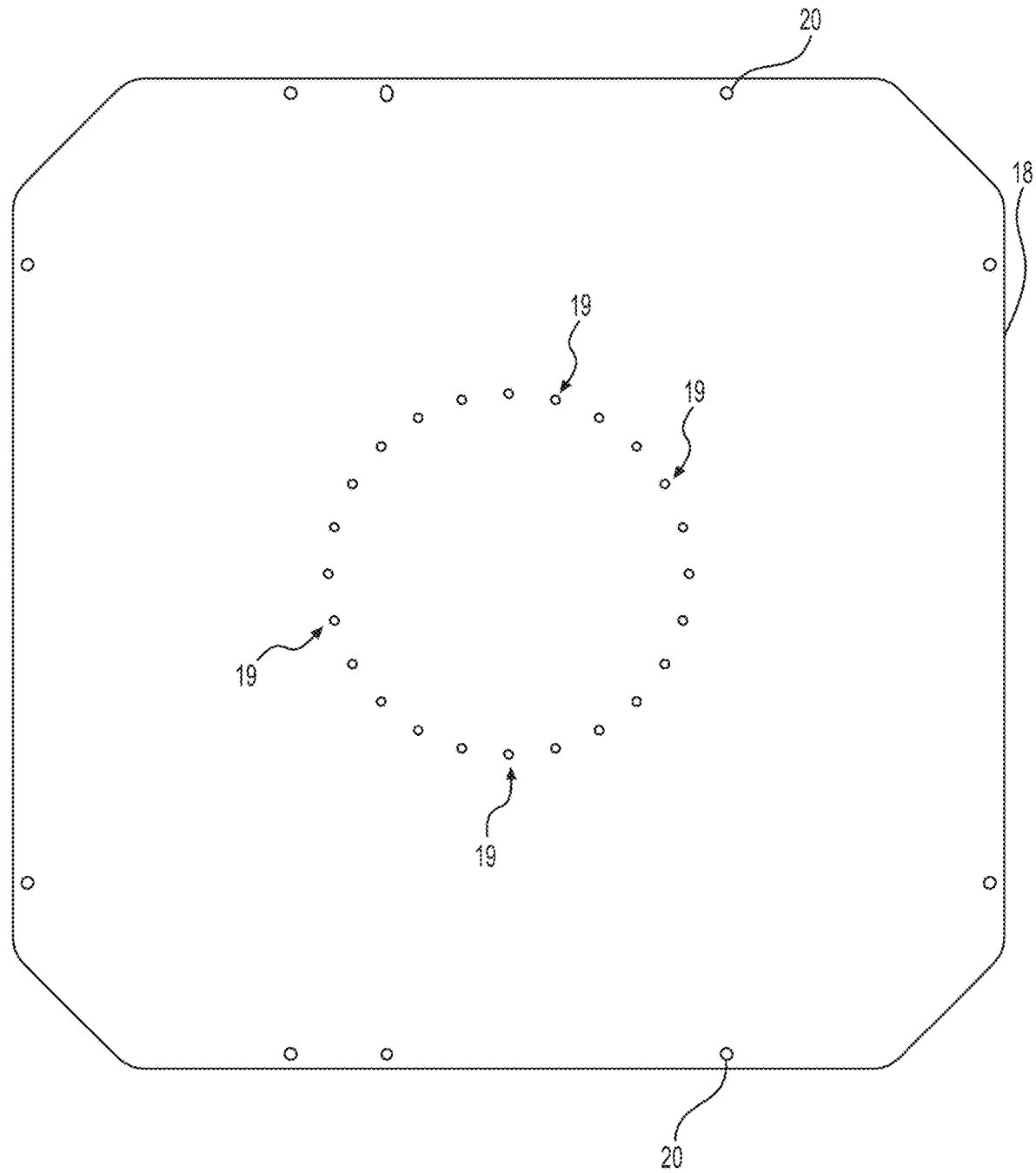
FIG. 40B is a plan view of a second plate of the radiolucent plate of FIG. 39 with a predetermined pattern of the radiopaque markers.

FIG. 40A shows the orientation plate 16 having a first set of radiopaque markers 17 in a predetermined pattern while FIG. 40B shows the registration plate 18 having a second set of radiopaque markers 19 in a predetermined pattern.

The second set of markers 19 in the registration plate 18 includes a plurality of radiopaque markers that are equally spaced from each other in a circular pattern. In the embodiment shown, there are 24 uniformly spaced markers in the registration plate 18.

The first set of markers 17 in the orientation plate 16 includes a set of markers that are spaced from each other in a circular pattern although the spacing among them is non-uniform. The circle formed by the markers 17 is smaller in diameter than the one defined by the second set of markers 19 in the registration plate 18. The two circles defined by the markers (smaller circle defined by markers 17 and larger circle defined by markers 19) are coaxial and concentric with one another.

The first set of markers 17 also includes markers (e.g., two shown for each of the corresponding non-uniformly spaced markers) that extend radially outwardly from the corresponding marker in the small circle defined by the non-uniform markers such that an imaginary line from the center of the circle crosses the radially extending markers and the corresponding marker in the circle. In the embodiment shown, there are 24 markers 17 in the orientation plate 16 (8 markers lying on the small circle and 8 subsets of 2 radially extending markers from the corresponding marker in the circle). It is important to note that the number of markers in both the registration plate 18 and the orientation plate 16 are the same at 24.

All radiopaque markers may be in the form of stainless steel balls or BBs' although they may be of any suitable radiopaque material.

The placement, size and the number of the radiopaque markers in the registration and orientation plates as described above provide optimal parameters for navigation accuracy, collimation requirements (i.e., ability to detect enough markers and place surgical implants accurately even with the presence of collimation which will truncate the patterns), minimization of anatomical obstruction to the surgeon during navigated procedures, and detection of orientation to allow navigation tracking software to deterministically detect whether the image is not flipped by 180-degrees or 90-degrees.

Although the radiolucent plate 14 is described with reference to a flat panel registration fixture 2, they may be implemented as part of a registration fixture (such as shown in FIG. 18) which is configured to be attached to a transmitter side of the imaging device.

The side frame has a plurality of optical tracking markers and is adapted to detachably mount to the base frame 6 without piercing a sterilizing drape to be interposed between the base frame 6 and the side frame.

As shown in FIG. 38, each side frame includes six flat disk markers and six spherical markers that are in fixed relationship with the radiopaque markers. The side frames 8,10 may be constructed from aluminum or any number of materials providing adequate strength, stiffness, weight, and optical properties relative to system accuracy requirements.

The side frames 8,10 may be bead blasted and black anodized to reduce potential reflections, among many surface treatment options. In the embodiment shown, the two side frames 8,10 are oriented 180-degrees from one another, and extend perpendicularly from the base frame 6. Each side frame 8, 10 may contain mounting features to enable the use of both flat tracking disks 22 and spherical markers 24 (only the posts are shown in FIG. 38) in order to allow both NIR and visible light tracking.

The flat disk markers 22 and spherical markers 24 are interspersed with each other. In one embodiment, the pattern and spacing of the markers 22,24 on one side frame 8 is identical to that of the other side frame 10 when viewing from their respective side (i.e., 180 degrees from each other).

The side frames 8,10 are self-aligning and oriented precisely to the base frame 6 through the use of a kinematic mount configuration 12.

Each side frame 8, 10 is designed to be non-interchangeable through the incorporation of a physical keying feature, which prevents users from accidental incorrect installation.

Figure 42:
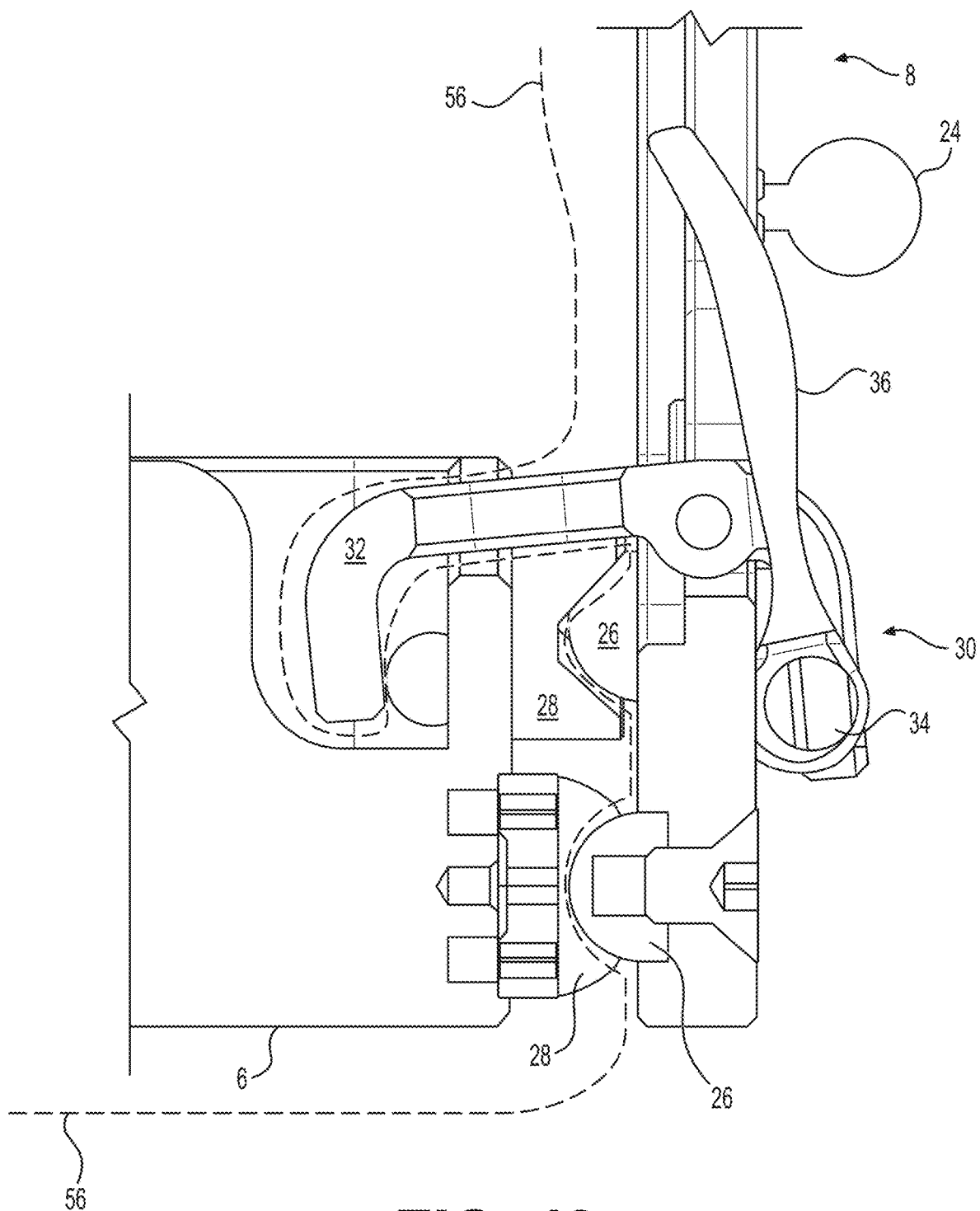
FIG. 42 is a side view of a kinematic mount of the side frame of FIG. 41 illustrating a non-piercing clamp.
Figure 43A:
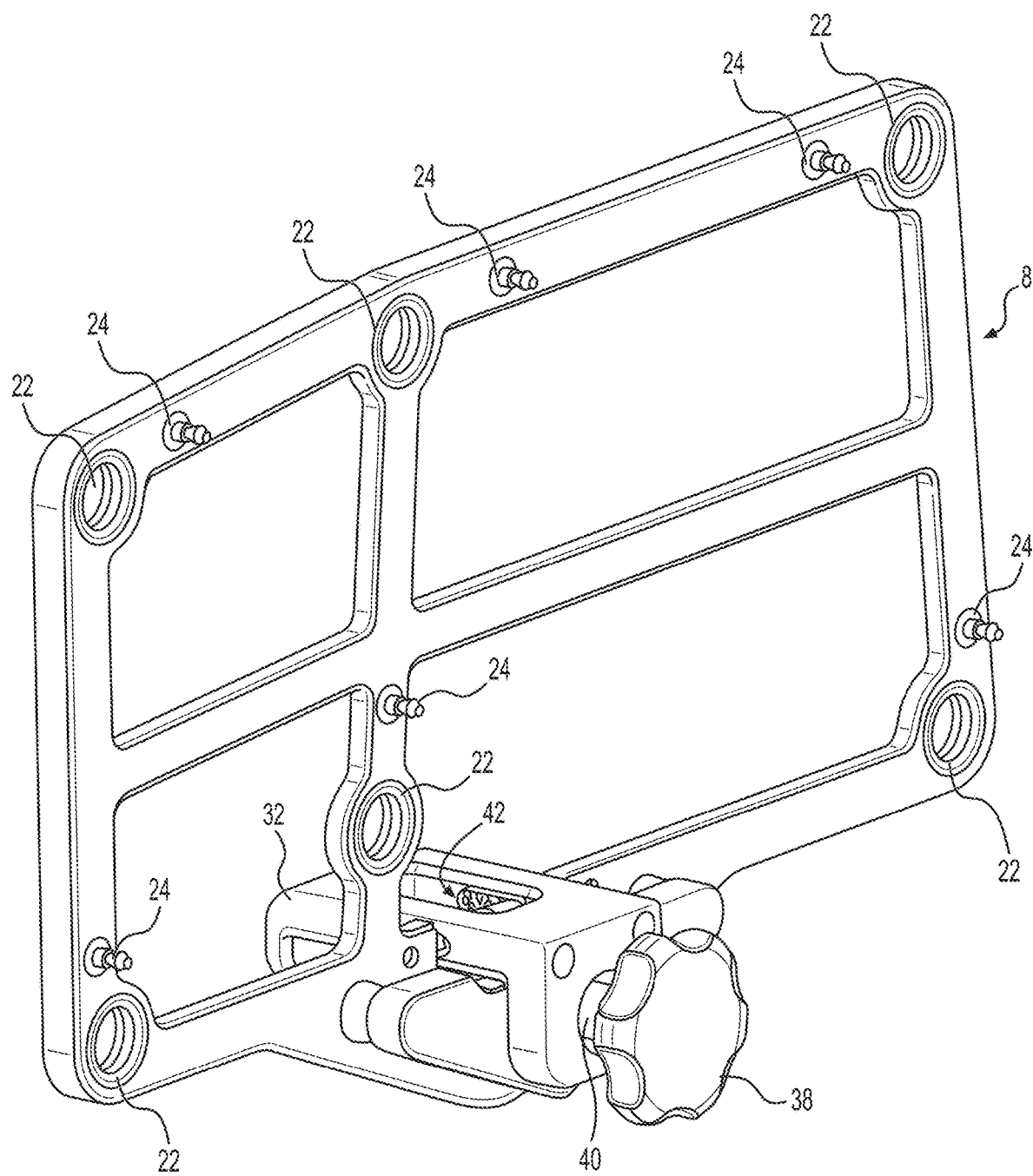
FIG. 43A is an outer perspective view of an alternative non-piercing kinematic clamp of the registration fixture of FIG. 38.
Figure 43B:
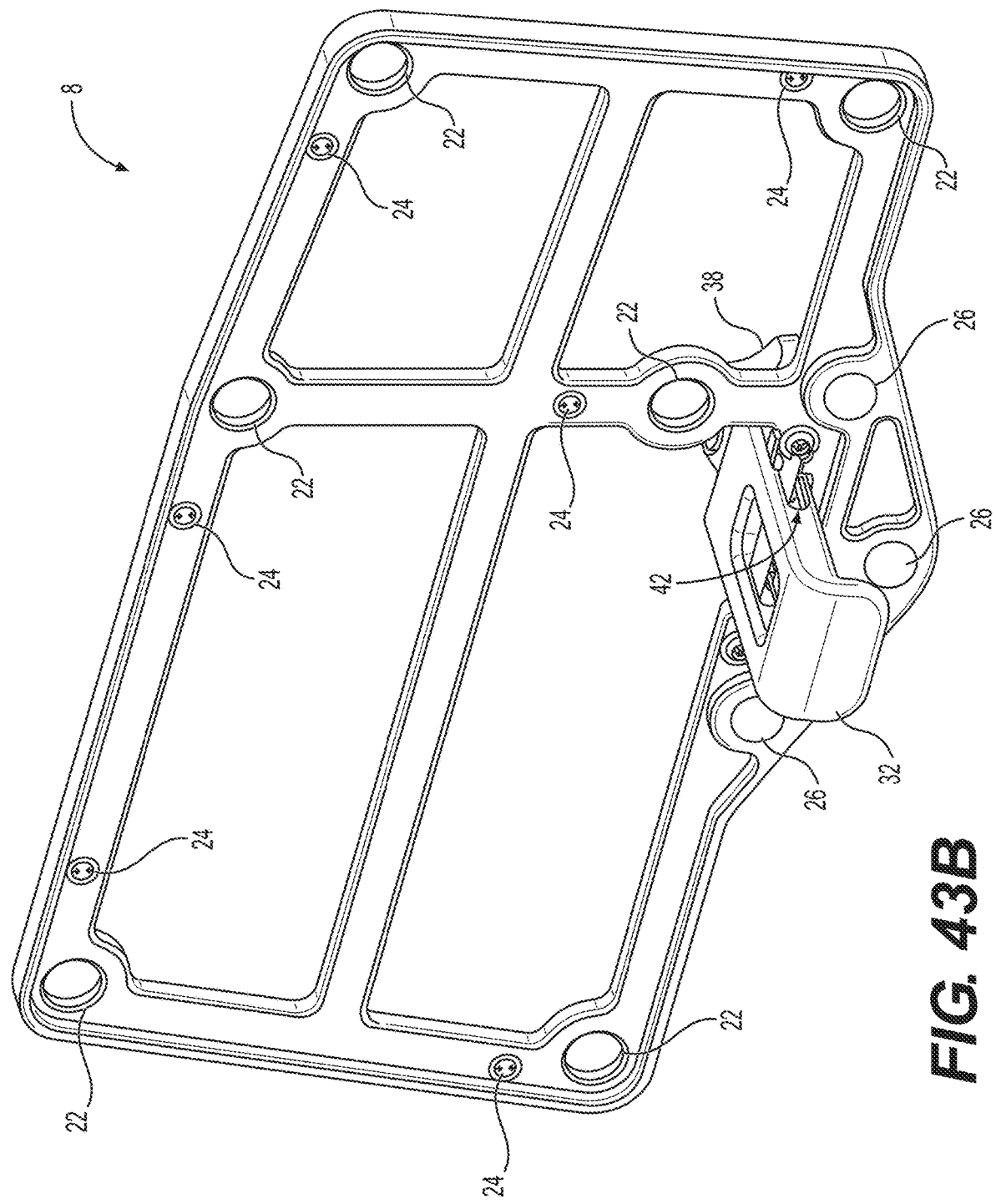
FIG. 43B is an outer perspective view of an alternative non-piercing kinematic clamp of the registration fixture of FIG. 38.
Figure 44:
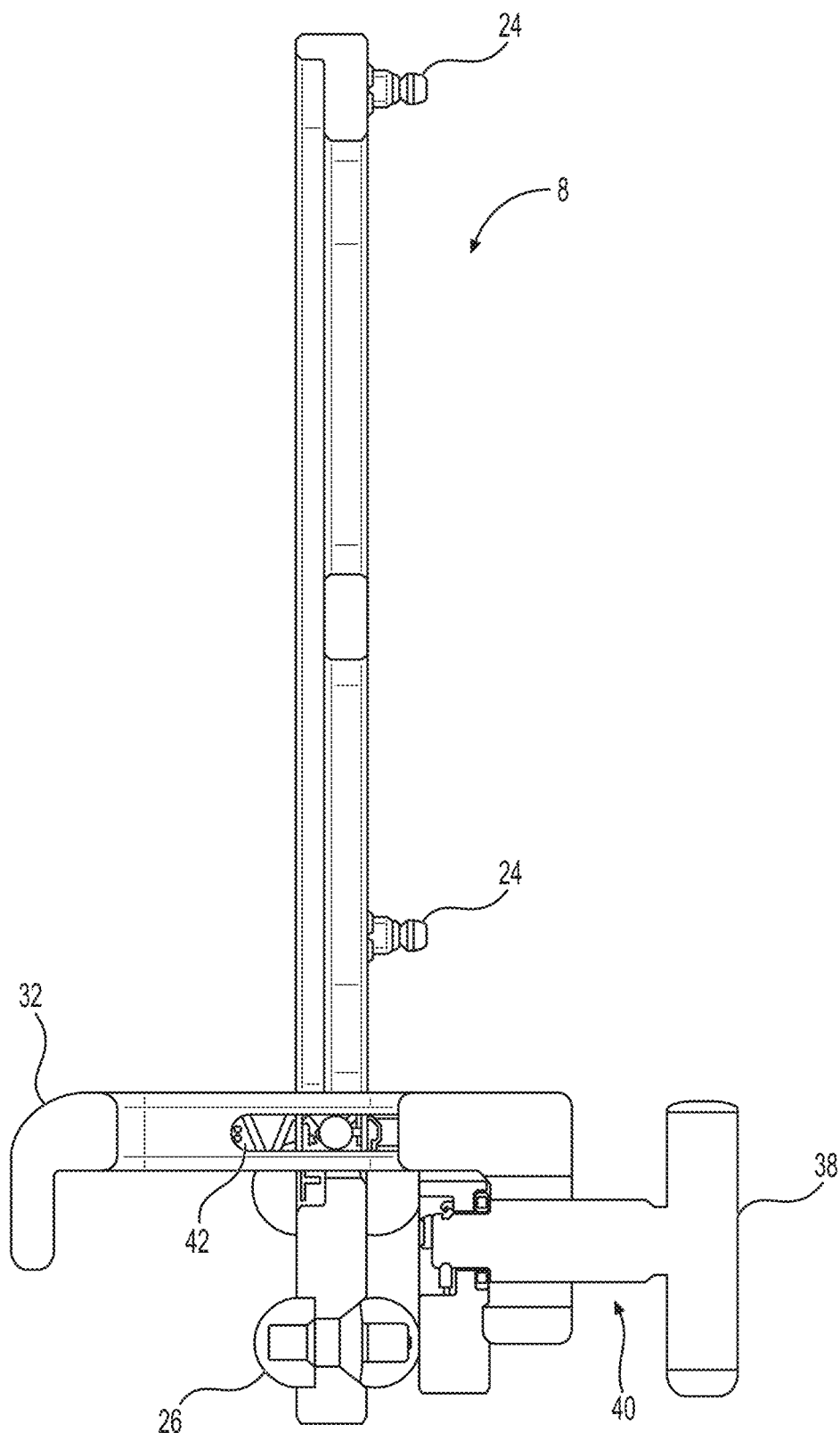
FIG. 44 is a cross-sectional view of the side frame of FIG. 43A.

As shown in FIGS. 38, 41 and 42, the base frame 6 includes three spaced apart kinematic mount points 28 (recesses shown as three vee blocks) configured to mount to corresponding kinematic mounts points 26 (shown as three truncated spherical balls) on the base frame 6 by self-alignment.

As shown in FIG. 42, a non-piercing clamp 30 includes a rotary pin 34 and a camming handle 36 coupled to the rotary pin and configured to move or translate the U-shaped clamp 32 so as to press the U-shaped clamp against the base frame 6. The U-shaped clamp 32 has a slot 42 (see FIG. 43A) that receives a part of the side frame 8 to allow a translational or sliding movement relative to the side frame in order to compress or release the base frame 6. In an alternate embodiment as shown in FIG. 38, the U-shaped clamp 32 is mountable over a side wall of the base frame 6 and a handle 38 having a threaded shaft 40 threadably coupled to the U-shaped clamp such that rotation of the handle presses the U-shaped clamp against the base frame 6 in order to fix the side frame 8 to the base frame 6.

The first side frame 8 extends laterally on one side of the base frame 6 and its tracking markers 22,24 face away from the base frame 6 in a first direction away from the base frame while the second side frame 10 extends laterally on the other side of the base frame 6 and its tracking markers 22,24 face away from the base frame 6 in a second direction opposite the first direction.

As shown in FIG. 38, the first and second side frames 8,10 are parallel to each other when mounted to the base frame 6. In the embodiment shown, the two side frames 8,10 are mounted perpendicularly to the base frame 6.

In one embodiment, the spherical tracking markers 24 of the side frames 8,10 are adapted to reflect infrared light (NIR) while flat disk markers 22 are adapted to reflect visible light and in some embodiments also the infrared light (NIR).

In order to facilitate the ability to mount to a variety of flat panel C-Arm detector housings, multiple flexible ratchet strap configurations have been designed and implemented.

Figure 45:
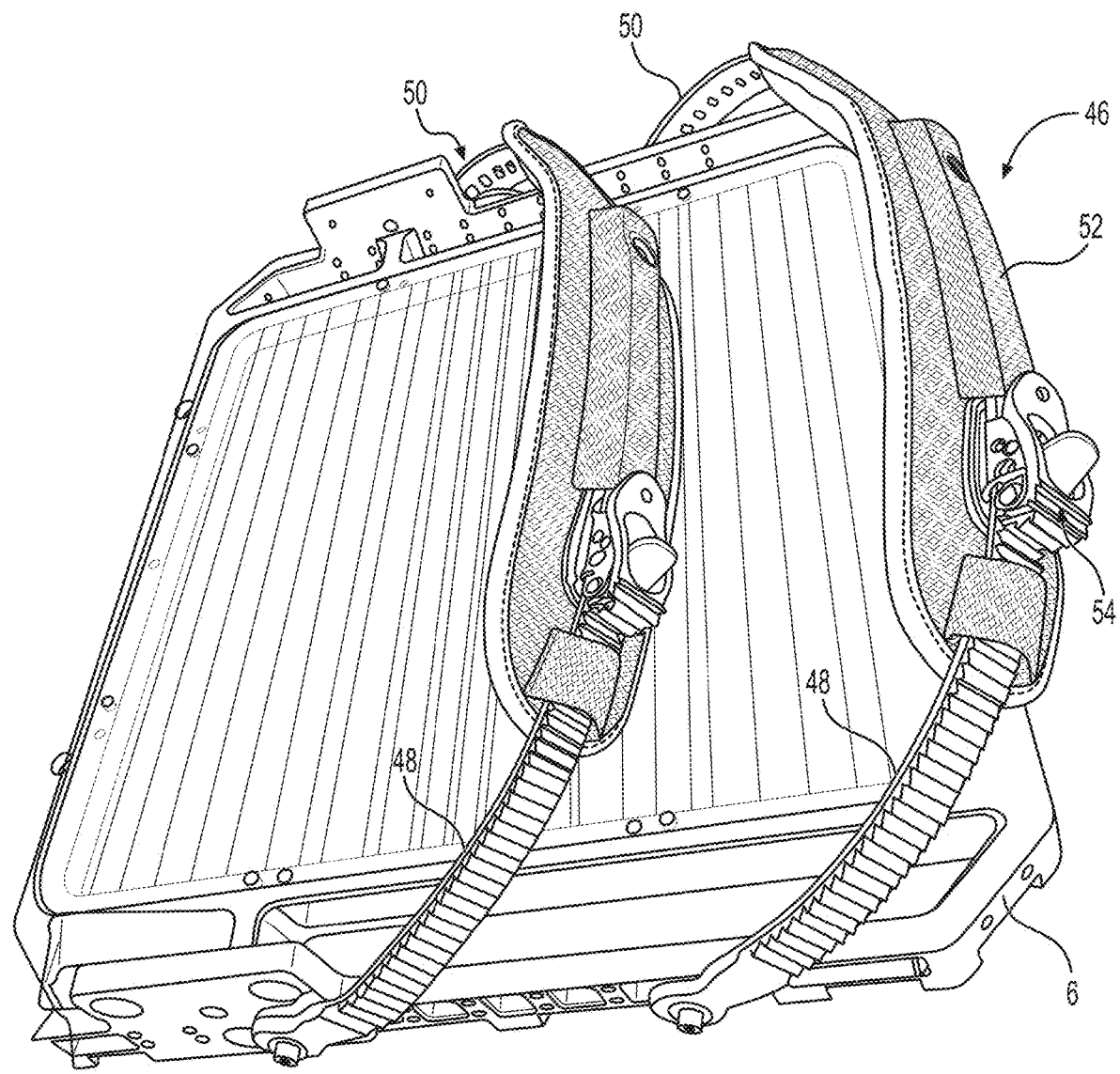
FIG. 45 is a perspective view of the base frame of FIG. 38 with a set of straps and a ratchet for attachment to the flat panel detector.
Figure 46:
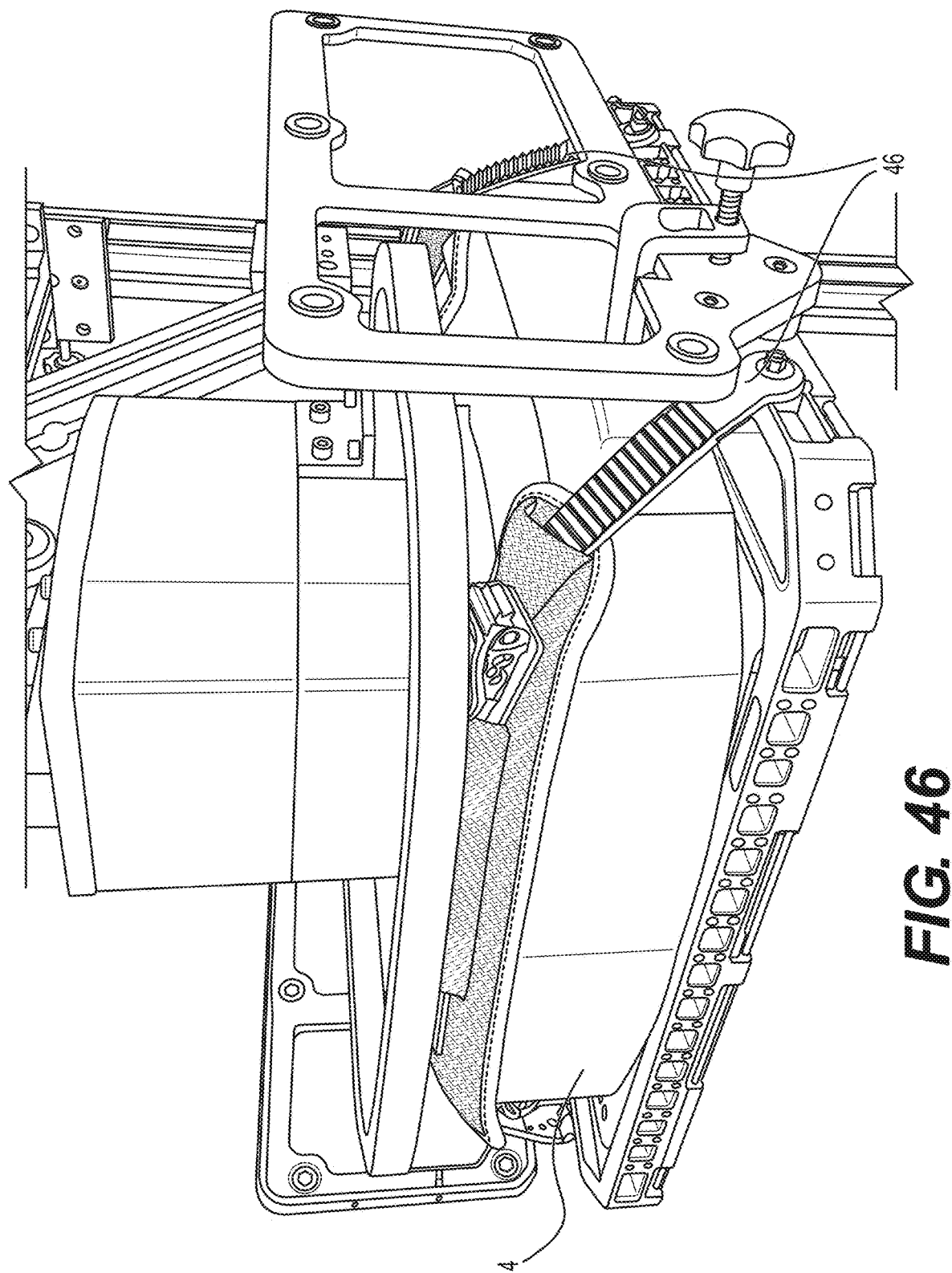
FIG. 46 illustrates the base frame of FIG. 38 as attached to the flat panel detector with the straps and ratchet as shown in FIG. 45.

FIG. 45 shows a ratchet strap assembly 46 including a set of straps 48,50, a pad assembly 52 and a ratchet 54 for attachment to the flat panel detector 4. FIG. 46 illustrates the base frame 6 of FIG. 38 as attached to the flat panel detector 4 with the ratchet strap assembly 46 as shown in FIG. 45. One end of a first strap 50 is rotationally attached to the base frame 6 and the other end is attached to the ratchet 54 through the pad assembly 52. One end of a second strap 48 (ladder strap) is rotationally coupled to the base frame 6 and the other side is coupled to the ratchet 54 for sliding adjustment relative to the first strap 50. The ratchets 54 allow adjustment of the straps 48,50 to fit over a variety of flat panel detectors 4. The ratchet strap assemblies 46 are available, for example, at M2 Inc. of Colchester, VT. The straps 48,50 extend from the base frame 6 and is configured to wrap around an underside of the flat panel detector 4 to temporarily fix the base frame 6 to the detector panel of the x-ray medical imaging device during use.

In one configuration, the first strap 50 of the ratchet strap assembly is composed of an extension component containing multiple thru holes to facilitate adjustability (FIG. 45). In another configuration, one end of the first strap 50 is attached to a hook component such as a spring loaded carabiner that attaches to a ring or a handle disposed behind the flat panel detector 4.

A flat panel detector registration fixture 2 as described above provides the following advantages.

Image collimation is possible while still allowing adequate orientation and registration fiducial marker detection for navigation and image processing requirements. Collimation has major advantages with respect to image quality as visualization of patient anatomy in certain scenarios can be extremely challenging without such collimation.

Optical tracking arrays mount to a precision kinematic mount configuration utilizing a clamp that prevents piercing of sterile drape. The clamp is designed in a u-shaped geometry which moves by either a camming handle integrated as actuator or a threaded handle (acting as a leadscrew) for rigid mounting to the base frame 6. Such mounting strategy protects the integrity of the sterile drape.

Non-piercing side frames 8,10 with optical tracking markers facilitate clamping of a separable, sterile, and autoclavable side frame which is unlike the conventional design that uses drape-piercing mount methodology. Side frames 8,10 containing optical tracking markers are separable from the base frame 6, utilize disposable markers, and are machine washable and autoclavable. The separable nature of the side frames 8,10 allows increased optimization for improved accuracy: size, segment length optimization, positioning relative to potential operating room obstructions.

Optical tracking arrays incorporate both passively tracked disks and spheres into single frame assembly to facilitate tracking utilizing NIR (spherical markers) and visible light technology (flat disk markers).

Novel radiopaque fiducial pattern is incorporated into orientation and registration plates to facilitate image processing and navigation workflows.

Ratchet strap mounting configuration utilizing a non-deterministic, compliant strap to facilitate fluoroscopy fixture mounting to a variety of c-arm detector panel geometries. Ratchet strap includes an adjustable extension component fastened in series to a compliant pad with spring-loaded mechanical ratchet, which interfaces with flexible ladder strap belt assembly. Ladder strap may optionally contain a hook or carabiner component for mounting to captive C-Arm handles. Optional design safety elements incorporated on belt assembly include hard stops.

Modular ratchet strap assembly has the ability to be adjusted along the perimeter of fluoroscopy fixture through utilization of self locking clevis pin, incorporating spring loaded wedge or equivalent locating and self-locking feature. Clevis pin incorporation facilitates easy user adjustment of ratchet strap assembly considering a variety of C-Arm detector housings.

Orientation and registration plate spacing has been minimized to between 25 mm to 50 mm in one embodiment to minimize obstruction within surgical work volume for clinical team, as compared to conventional fluoro fixtures with 100 mm or greater plate separation distance. This plate separation may be decreased or increased to improve accuracy, but has been minimized in order to maximize available workspace for clinical surgical team.

Finding True Fluoro Fixture Location

As explained above, one part of the above algorithm for registering the CT image to the tracking cameras is to accurately track the location of the image plane and emitter relative to the patient tracker so that the DRRs are generated with correct corresponding configuration of the virtual emitter and virtual collector relative to the CT volume. One way that software can track the image plane is by tracking a fixture directly attached to the face of the image collector of the C-arm. The emitter location is then accurately determined by using a "pinhole camera" algorithm where the shadows of two planes of BBs passing through the fixture are analyzed to determine where the emitter must have been relative to the collector to create such shadows. One underlying assumption of CT-fluoro registration processes is that the far BB plane of the tracked fluoro fixture, which is up against the physical collector of the C-arm, can be considered to be coincident with the X-ray image plane, even though the BB plane is really several centimeters from the hardware that detects the X-rays.

Note that in the analysis of emitter location based on projections of two planes of BBs, computational approaches are used for which open-source software is available for camera calibration functions. In one computational approach, the geometric locations of the BBs in 3D on the fixture in Cartesian coordinates (x, y, z positions in mm) are called the object points and the projected shadows of the BBs on 2D X-rays in pixel coordinates are called the image points.

Referring to FIG. 17, X-ray shadow locations are illustrated from two planes of BBs. No matter where the collector is positioned below the two BB planes (near Plane A and far Plane B), the ratio of $L_{2b}/L_{2a}$ remains constant. Therefore, the far plane (Plane B) can be considered to be the actual image plane. One complicating factor is that the BB plane of the fluoro fixture may not be attached to the C-arm exactly parallel to the image plane. In such a case, it is no longer valid to make the simplification that the BB plane and image plane are coincident. However, by correcting for the angle of the BB plane, it is still possible to accurately find the location of the emitter relative to the fluoro fixture and closest image plane.

In treating the optics such that the image plane is considered parallel and coincident with the fluoro fixture, the known location of the tracking array is used to directly determine the position of the image plane (fixture plane) relative to the cameras. Since the center BB of the image plane is considered the origin (0,0,0) of the fluoro fixture, the tracked pose of the sphere/disc optical array represents the tracked pose of the image plane.

With a tilted image plane, however, the actual position of the image plane is not actually at the location in space extrapolated from the markers attached to the fixture. There is instead a rotation about an axis of rotation and through the origin of the image plane (BB plane) that must be considered. That is, having an angled fixture on the C-arm would be the same as having a non-angled fixture on the C-arm with its BB locations and array location shifted by a rotation about an axis that lies on the image plane. To compensate for the rotation, the following algorithm can be used:

1. Find the axis of rotation of the fixture on the image plane and the degrees of rotation about this axis;
2. Apply this rotation to the object points so that calibration now relies on rotated object points. Rotation is applied around the origin of the fixture.
3. Apply this rotation to the extrapolated location of the tracking array so that the tracked position represents the location of the image plane, not the fixture plane. Rotation of the tracking array is also applied around the origin of the fixture.
4. Determine the projection matrix as usual using a calibration algorithm but with rotated object points.
5. Send modified projection matrix and modified tracked array position to a registration algorithm.

Step 1 can be solved knowing the rotation matrix returned by the calibration algorithm. This rotation matrix can be considered a sequence of three planar rotations: (1) a rotation about the fixed Z axis followed by (2) a rotation about the fixed X axis, followed by (3) a second rotation about the fixed Z axis. In other words, rotate the image to dial in the azimuth and then apply the tilt; then rotate the resulting image to the perspective desired. Since rotations about moving axes are the opposite order of rotations about fixed axes, this rotation sequence is the same as (1) a rotation about the fixed Z axis followed by (2) a rotation about the fixed X axis followed by (3) a rotation about the fixed Z axis.

To proceed to the next phase of the algorithm, the object points may be modified by a sequence of three rotations to move them to a location where the image points actually produced would show no tilt angle. This sequence of rotations is similar to the rotation sequence of three rotations previously described, but is slightly different because the z rotation previously used to compensate for screen rotation is now used to compensate for the tilt azimuth. The direction of the tilt to be applied is chosen (rotation about z), the tilt is then applied (rotation about x), and then a compensatory rotation is applied such that there is no twist of the joint. The first and third (z) rotations should sum to zero.

These modified object points are used to compute a modified projection matrix and to compute a modified fixture tracking array location. With modified projection matrix and fixture tracking matrix, a new projection matrix is computed and sent to the registration algorithm in place of the projection matrix from the old algorithm. This new projection matrix represents a projection onto the true image plane instead of onto the fixture plane, giving better accuracy in the final fluoro-CT registration.

Alternative Fixture Tilt Solution

In the above analysis, the fixture tilt is determined using a calibration function and manipulating the resulting projection matrix. If all that is needed is the fixture tilt, which may be used to, for example, provide a warning to the user that the fixture is tilted to indicate that it needs adjustment, another approach can be that is based on the projected appearance of rings. Using rings may be more robust than the above-described method because it is possible that rings are less susceptible to shape changes from pincushion and S-distortion than raw individual BB positions.

Figure 47A:
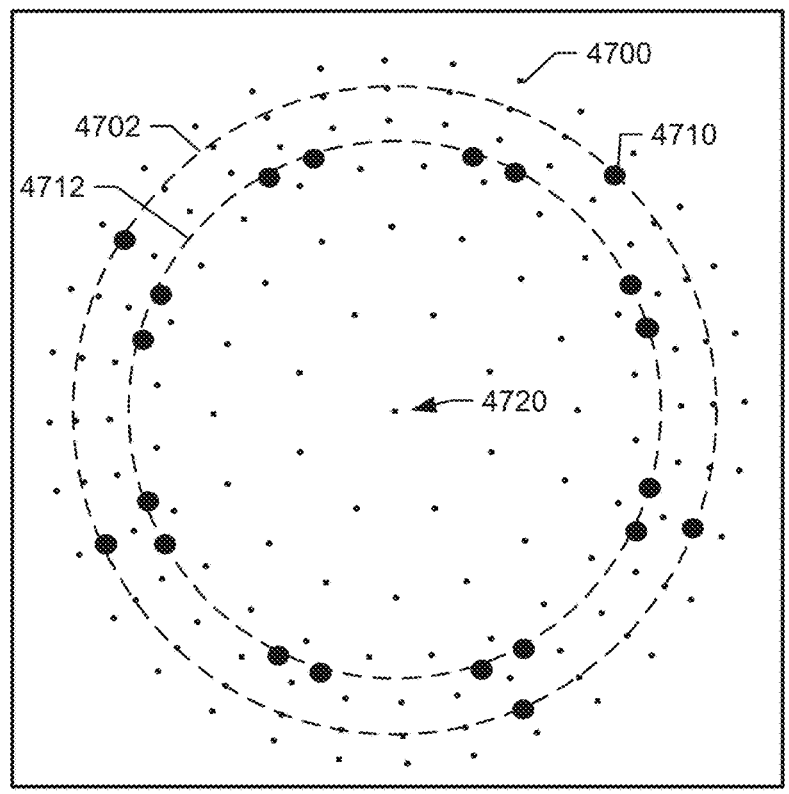
FIGS. 47A and 47B illustrate X-ray images taken with 9-inch and 12-inch fluoro fixtures, respectively, from Globus Medical, Inc. attached to a C-arm.
Figure 47B:
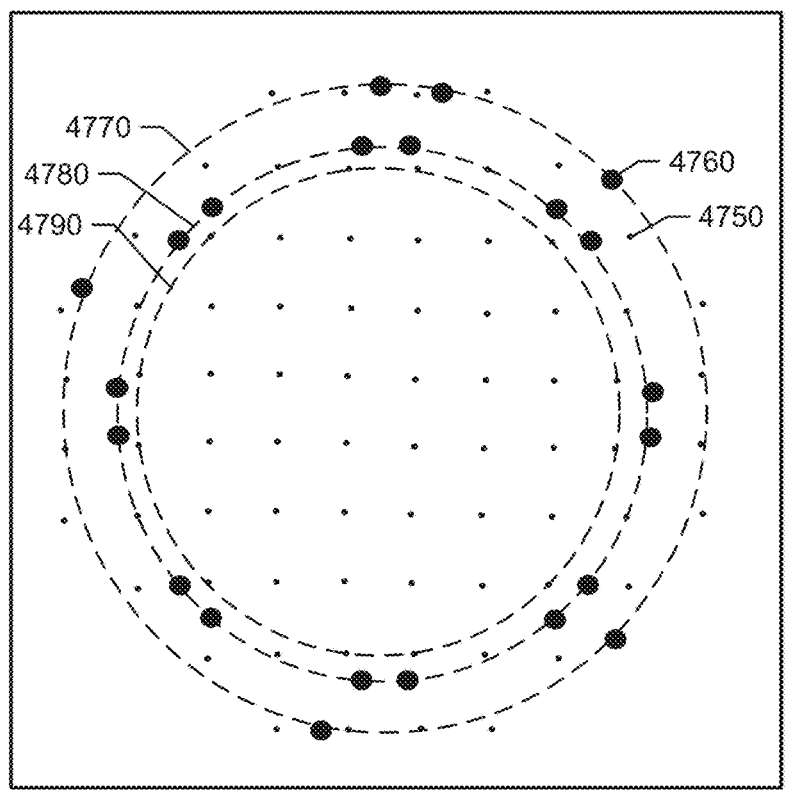

This approach can be effective using the 9" and 12" fluoro fixtures, e.g., from Globus Medical, Inc., because in both fixtures the patterns of BBs can be interpreted as ring-shaped when processing the image. FIGS. 47A and 47B illustrate X-ray images taken with 9-inch and 12-inch fluoro fixtures, respectively, from Globus Medical, Inc. attached to a C-arm. The illustrated BBs (black circles) are imaged shadows cast from a first set of BBs on an orientation plane and from a second set of BBs on a registration plane.

More particularly, FIG. 47A illustrates first and second sets of BBs arranged according to some embodiments, such as for a 9" fixture configured for use during registration of a medical image to a three-dimensional tracking space. FIG. 47B illustrates first and second sets of BBs arranged according to some other embodiments, such as for a 12" fixture configured for use during registration of a medical image to a three-dimensional tracking space.

Referring to the embodiment of FIG. 47A, a first set of BBs 4700 or other radiopaque markers on an orientation plate are arranged along radial lines which extend from a center location 4720, the radial lines are angularly spaced apart about the center location 4720. FIG. 47A further illustrates a second set of BBs 4710 or other radiopaque markers arranged along two circles 4702 and 4712, where the second set of BBs are on a registration plate that is spaced apart from the orientation plate. The registration plate and the orientation plate can be attached to a base frame of a registration fixture which is adapted to be mounted to an x-ray medical imaging device, such as to a flat panel detector of the x-ray medical imaging device.

Referring to the embodiment of FIG. 47B, a first set of BBs 4750 or other radiopaque markers are arranged on an orientation plate. FIG. 47B further illustrates a second set of BBs 4710 or other radiopaque markers arranged along three circles 4770, 4780, and 4790, where the second set of BBs are on a registration plate that is spaced apart from the orientation plate. The registration plate and the orientation plate can be attached to a base frame of a registration fixture which is adapted to be mounted to an x-ray medical imaging device.

In FIGS. 47A and 47B, the BBs of the first set (4700 and 4750) are illustrated as being smaller than the BB s of the second set (4710 and 4760), although in some other embodiments the BBs of the first set are larger or the same size as the BBs of the second set. Using different size BBs between the first and second sets facilitates distinguishing between the sets of markers during processing of an image.

In the example embodiment of FIGS. 47A and 47B, 16 BBs 4710 and 4760 on the respective registration plates (also called "registration BBs") are identified during processing of an image as being arranged along a circle-shaped (also "ring-shaped") configuration, shown as circle 4712 in the 9" fixture configuration of FIG. 47A and as circle 4780 in the 12" fixture configuration of FIG. 47B. In the 9" fixture configuration of FIG. 47A, the set of BBs 4700 of the orientation plate (also called "orientation BBs") on the dewarping plane are arranged in a circle and additional dewarping BBs 4700 on the same plane are on the same circle 4702, allowing further refinement of the circle shape.

Alternately, if anatomy or metal artifact blocks much of the circle 4702 shown in FIG. 47A, a different circle could be formed from a set of small diameter grid BBs at a different radius since the grid BBs 4750 of FIG. 47B and orientation BBs 4700 of FIG. 47A are on the same plane.

In the 12" fixture configuration of FIG. 47B, there are no additional dewarping BBs on the same circle 4770 as the first set of BBs of the orientation plate, but different subgroups of dewarping (grid) BBs could potentially be candidates for circles. Although the circle 4770 for the 12" fixture formed from the large diameter second set of BBs 4760 of the orientation plate might be considered the primary intended circle, other circles formed from BBs at different radii would also be suitable candidates. Note that a circle 4790 including 12 grid BBs 4750 may be formed as a suitable alternative to the circle 4770, which only uses 6 BBs 4760 of the second set. The second set of BBs in this alternate ring have a nominal radius of 94.257 mm from the center, in accordance with one embodiment.

A geometric analysis of the rings in the path of the X-rays is represented schematically (FIG. 30). If the far plane ring is "magnified" to match the known ratio of diameters of upper and lower rings (e.g., 1 if they are the same diameter), it would be the same as if the line in the schematic of FIG. 30 representing ring B were moved up in the vertical direction since scaling is done for values of each point on the ring in the coordinate system where ring points are offset from zero. Note that due to parallax, this shift alters the projected center of the ring.

This z position becomes the z position of the major axis of both ellipses. Therefore, with the far field ellipse scaled and the near field ellipse not scaled, the offset in the centers of the ellipses represents the measurement in image coordinates of the side opposite in a triangle with hypotenuse equal to the distance between rings. At this z position, it is easy to find the hypotenuse in image coordinates: it is the distance between rings in mm times the ratio of near field ellipse major axis over near field ring diameter (or times the ratio of scaled far field ellipse major axis over far field ring diameter, which is by definition of the scaling factor the same).

The arcsine function of Equation 12 described above can be used to solve for $\alpha$ using the the side opposite and hypotenuse. These operations can be applied while each image is processed from the fluoro C_arm, to provide immediate feedback to the user on whether the fixture is tilted.

In a further embodiment, the operations may generate a warning notification to a user when the tilt angle of the fixture satisfies a notification rule, e.g., exceeds a threshold fixture tilt angle. The warning notification may correspond to displaying a warning message informing the user that the fixture is not properly mounted to the flat panel detector of the C_arm and/or may correspond to generate an audible warning and/or activating/deactivating a light. The operations may further disable operation of the C_arm for use in performing imaging until the tilt angle of the fixture is determined to satisfy an imaging operation rule, which may correspond to the notification rule.

Improved Collimation

When capturing a fluoroscopy (fluoro) image for use in a registration algorithm, the surgeon or radiology technician may need to collimate the field to create an image that has even contrast and is not overly dark or bright in certain areas. Collimation is blocking of the X-ray path using a lead curtain and is adjustable on the console of most C-arms. When less than the full-size image is captured, fewer BB shadows are available for the analysis of the emitter location using, e.g., a pinhole camera model.

In order to improve the ability to detect a partially collimated image, multiple rings of orientation BBs may be included on an orientation plate of a flat panel fluoro fixture (FPFF), which is an non-limiting example type of a registration fixture.

A registration fixture for registration of a medical image to a three-dimensional tracking space, can include a base frame, an orientation plate, and a registration plate. The base frame is adapted to be mounted to an x-ray medical imaging device. The orientation plate is attached to the base frame and has a first set of BBs (or other radiopaque markers) arranged along at least four radial lines which extend from a center location, and where the radial lines are angularly spaced apart about the center location, and at least three of the BBs are arranged along each of the radial lines. The registration plate is attached to the base frame and spaced apart from the orientation plate. The registration plate has a second set of BBs (or other radiopaque markers) arranged along a circle.

Although some embodiments are described as using BBs, these and other embodiments may more generally use any type of radiopaque markers. The radiopaque markers are not restricted to being round and are not restricted to being discontinuous spaced apart marker structures. The radiopaque markers can have any shape, such as oblong, square, etc. The radiopaque markers may be spaced apart thicker cross-sectional regions of a continuous material plate, where the thicker cross-sectional regions are configured to be more radiopaque than the plate regions intervening between the thicker cross-sectional regions. The thicker cross-sectional regions are configured to have their locations recognized through image processing of an image of the plate by an x-ray medical imaging device. Accordingly, all references to "BBs" herein can be replaced by the term "radiopaque markers" in accordance with these and other embodiments of the present disclosure.

Figure 48:
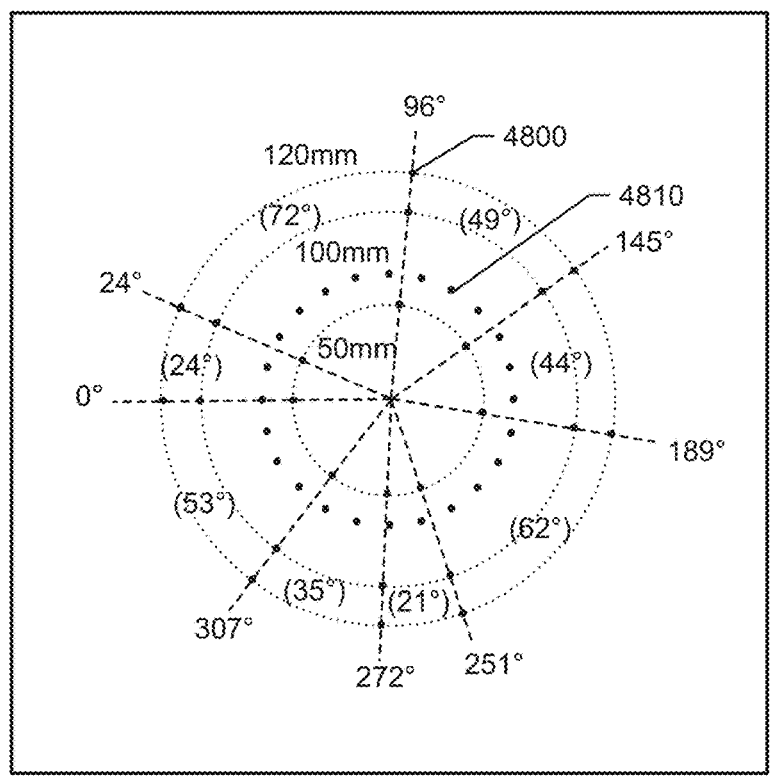
FIGS. 48 and 49 illustrate top-down views of a first set of BBs on the orientation plate and a second set of BBs on the registration plate, and where the first and sets of BBs are oriented according to some embodiments.
Figure 49:
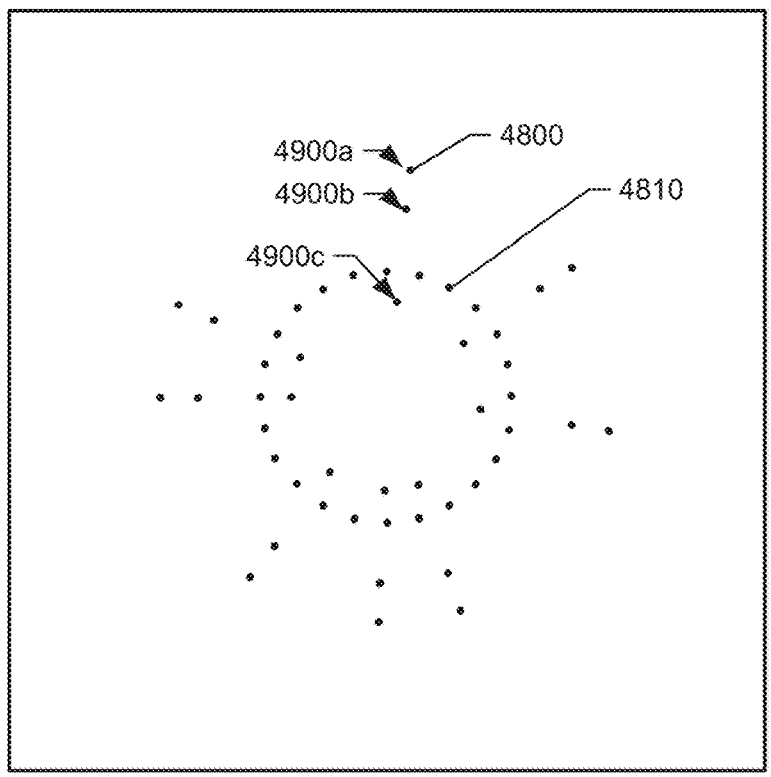

FIGS. 48 and 49 illustrates a top-down view of a first set of BBs 4800 on the orientation plate and a second set of BBs 4810 on the registration plate, and where the first and sets of BBs are oriented according to some embodiments.

Referring to FIG. 49, the first set of BBs 4800 on the orientation plate are arranged along eight radial lines which extend from a center location, and where the center location of the radial lines does not necessarily correspond to a center of the orientation plate. The eight radial lines are angularly spaced apart about the center location at, for example, 0°, 24°, 96°, 145°, 189°, 251°, 272°, and 307° as shown in FIG. 48. Three of the radiopaque markers 4900a, 4900b, 4900c of the first set are arranged along each of radial lines at three different radii from the center location. In some embodiments, the radial lines are angularly spaced at least 20 degrees apart. The radial lines may be non-uniformly angularly spaced, and angles between two adjacent pairs of radial lines differ by at least 2 degrees. In other words, the radial lines can be arranged to have unique angles between adjacent radial lines which differ by at least 2 degrees, such that a maximum of two arms can match under any possible combination of a rotation and mirroring when processing the image.

In some other embodiments, the orientation plate is configured with fewer than eight radial lines or with more than eight radial lines. In some embodiments, the first set of radiopaque markers are arranged along at least eight radial lines which extend from the center location, the radial lines are angularly spaced apart about the center location, and at least three of the radiopaque markers of the first set are arranged along each of radial lines. In one embodiment, the first set of radiopaque markers are arranged along six radial lines, such as for a 9" fixture or a 12" fixture. In another embodiment, the first set of radiopaque markers are arranged along seven radial lines. The radial lines may be arranged with different unique angles between adjacent pairs of radial lines. The first set of radiopaque markers on each of the radial lines may be arranged with different minimum spacing therebetween and with different radial locations along the radial lines. In another embodiment, the radial lines are uniformly angularly spaced at least 20 degrees apart about the center location.

The orientation of the first set of BBs of the orientation plate illustrated in FIGS. 48 and 49 may provide an optimized balance between the number of BBs in the first set, the number of radial lines ("arms"), and the locations of the BBs along the radial lines. Having a large number of radial lines (e.g., 8) and the BBs of the first set located at three different radii was determined to possibly provide an optimized balanced for a 9" or 12" registration fixture based on the following four considerations.

As a first consideration, there should not be a sufficient number of BBs in the first set of the orientation plate to allow reliable registration while avoiding an excessive number of BBs in the first set in order to avoid additional unnecessary registration fixture cost, manufacturing complexity, image processing complexity, and obscuring of imaged patient anatomy. Increasing the number of BBs in the first set can generally improve registration accuracy, particularly when the BBs in the first set have a large spread in the image, e.g., corresponding to the area formed by a polygon with the outer BBs as vertices.

As a second consideration, the pattern of BBs in the first set of the orientation plate should be able to be recognized through image processing while subjected to significant collimation. It is desirable to have the pattern of BBs widely dispersed, but with many radial lines (arms) still recognizable through image processing even if the horizontal, vertical, or both portions of the image have been collimated. It is also possible for non-vertical/horizontal collimations to be created on some systems, so at least some BBs in the first set should be near the center location from which the radial lines virtually extend.

As a third consideration, the pattern of BB s in the first set of the orientation plate should provide a uniquely recognizable pattern during processing of the image even with some of the BBs in the first set are not recognizable, e.g., missing from the image, and so the pattern of BBs in the first set can be unambiguously recognized at any rotation and with the pattern of BBs in the first set being potentially flipped, e.g., since some C-arm x-ray medical imaging devices may optionally flip the image during software processing such as along with color inversion and other image processing steps.

As a fourth consideration, the second set of BBs of the registration plate should be distinctly separated geometrically from the first set of BBs of the orientation plate (e.g., along the parallel planes of the orientation and registration plates), even if the emitter is located off-center or the fixture is tilted. The separation allows simpler and more accurate detection of the second set of BBs of the registration plate because they will not intersect either the innermost or the middle ring of BBs in the first set of the orientation plate.

With continued reference to FIGS. 48 and 49, the illustrated BB patterns can be highly resistant to collimation, by allowing a sufficient number of the BBs in the second set of the registration plate and a sufficient number of the BBs in the first set of the orientation plate orientation BBs to be recognized during processing of the image. A best-fit circle can be fitted to each set of BBs even if not all BBs are recognizable or captured in the image, and the angles of the radial lines relative to each other can be determined relative to the center location of the orientation circle. The illustrated layout of BBs allows for determination of the pattern with as few as three BBs in the first set of the orientation plate and three BBs in the second set of the registration plate, due to the unique angles between the arrangements of the BB s in the first set along the radial lines.

In some embodiments, an improvement to the ability to accurately recognize the circles of BBs during processing may be obtained by including at least four BBs in the first set of the orientation plate and at least six BBs in the second set of the registration plate. However, in some situations, more than these numbers of BBs will be available, even when collimated in more than one direction and/or when rotated. In FIG. 49, for instance, there are 14 BBs in the first set of the orientation plate and/or 14 BBs in the second set of the registration plate visible in the horizontal collimation and 14 BBs in the first set of the orientation plate and/or 16 BBs in the second set of the registration plate visible in the vertical. Even if both are collimations are combined, the inner region still contains eight BBs in the first set of the orientation plate and six BBs in the second set of the registration plate, which are sufficient to register the image accurately, but possibly with less accuracy than the full image because only a portion of the complete sets of BBs are recognizable in the image.

The example pattern shown in FIG. 49 for the first set of BBs on the orientation plate and the second set of BBs on the registration plate, was designed using a Python programming language script that iterated through random patterns to identify patterns that had only two collisions, where BBs of the first set are aligned with BBs of the second set in a direction normal to the orientation plate and the registration plate. After checking about 1.5 million potential patterns and finding 128 potentially matching patterns, the matching patterns were then visualized via a flag in the script as PNG images, and a candidate with a spread was selected visually as providing better collimation resistance but potentially more ambiguity under low resolution, higher tilt, etc., and which resulted in the illustrated pattern.

In some other embodiments, the first set of radiopaque markers may be arranged along a plurality of concentric circles. The first set of radiopaque markers may include at least 24 radiopaque markers arranged along at least three concentric circles. The second set of radiopaque markers may include at least four radiopaque markers. The second set of radiopaque markers may include at least 24 radiopaque markers. The orientation plate and the registration plate may be attached parallel to each other on the base frame.

In a further embodiment, the first set of radiopaque markers include at least 24 radiopaque markers arranged along at least three concentric circles, and the second set of radiopaque markers are arranged along the circle with a center location which is aligned, in a direction normal to the orientation plate and the registration plate, with the center location of the at least three concentric circles of the at least 24 radiopaque markers of the first set.

In a further embodiment, the orientation plate and the registration plate are parallel to each other, and none of the radiopaque markers of the first set are aligned with any of the radiopaque markers of the second set in a direction normal to the orientation plate and the registration plate.

In a further embodiment, the registration fixture includes a side frame adapted to detachably mount to a plurality of optical tracking markers and adapted to detachably mount to the base frame.

Figure 50:
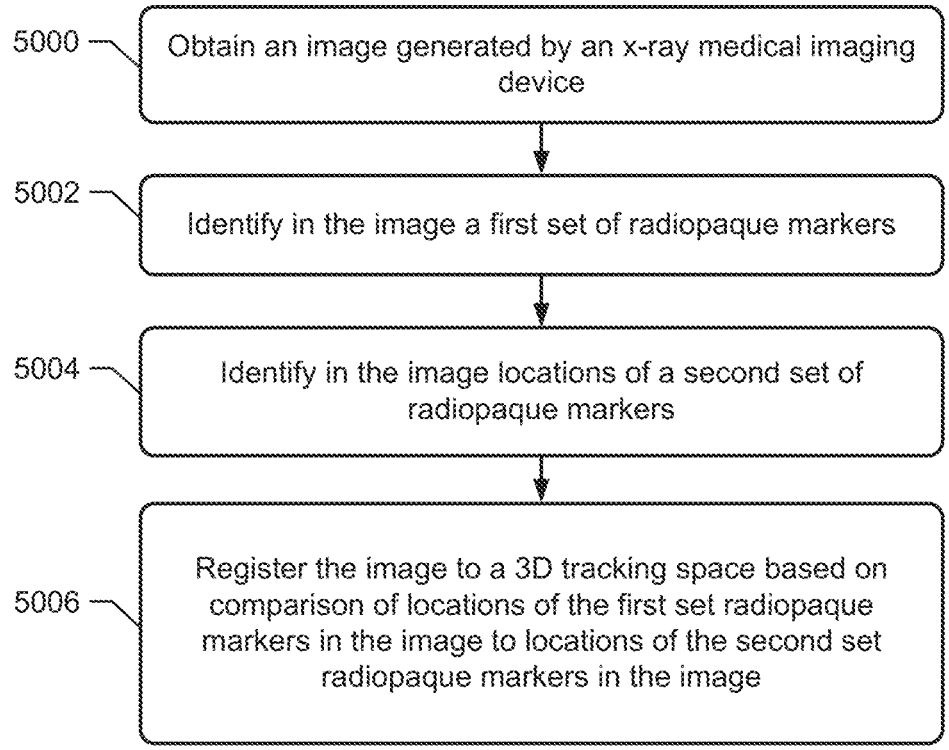
FIGS. 50 and 51 illustrate flowcharts of operations that may be performed by a surgical navigation system in accordance with some embodiments.

A further embodiment is directed to a surgical navigation system for registration of a medical image to a three-dimensional tracking space. The surgical navigation system includes at least one processor, and at least one memory storing instructions executable by the at least one processor to perform operations. FIG. 50 illustrates a flowchart of operations that may be performed by a surgical navigation system in accordance with some embodiments. Referring to FIG. 50, the operations include to obtain 5000 an image generated by an x-ray medical imaging device. The operations identify 5002 in the image a first set of radiopaque markers based on recognizing the first set of radiopaque markers are arranged along at least four radial lines which extend from a center location, based on recognizing the radial lines are angularly spaced apart about the center location, and based on recognizing at least three of the radiopaque markers are arranged along each of the radial lines. The operations identify 5004 in the image locations of a second set of radiopaque markers based on recognizing the second set of radiopaque markers are arranged along a circle. The operations register 5006 the image to a three-dimensional tracking space based on comparison of locations of the first set radiopaque markers in the image to locations of the second set radiopaque markers in the image.

Figure 51:
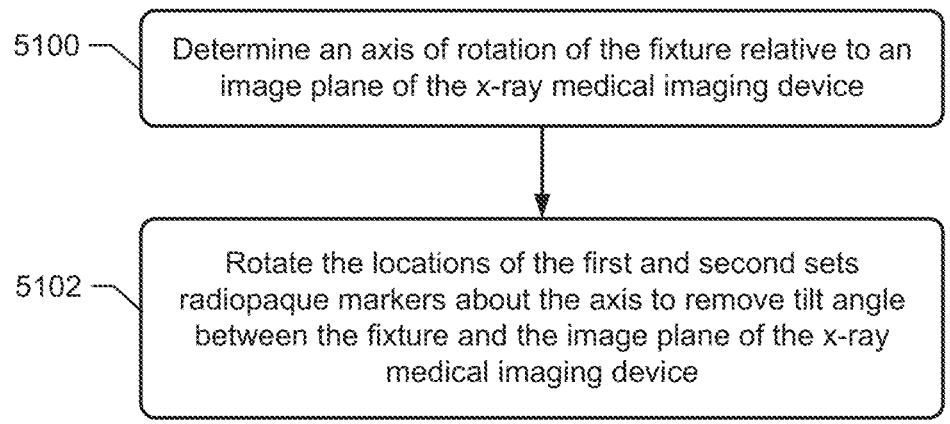

FIG. 51 illustrates a flowchart of operations that may be further performed by the surgical navigation system in accordance with some embodiments. Referring to FIG. 51, in a further embodiment based on the 5 steps described above for compensating for a tilted image plane, the operation to register 5006 the image to the three-dimensional tracking space based on comparison of locations of the first set radiopaque markers in the image to locations of the second set radiopaque markers in the image, includes to determine 5100 an axis of rotation of the fixture relative to an image plane of the x-ray medical imaging device, and rotate 5102 the locations of the first and second sets radiopaque markers about the axis to remove tilt angle between the fixture and the image plane of the x-ray medical imaging device.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. A surgical navigation system for registration of a medical image to a three-dimensional tracking space comprising:
at least one processor; and
at least one memory storing instructions executable by the at least one processor to perform operations including to
obtain an image generated by an x-ray medical imaging device,
identify in the image a first set of radiopaque markers based on recognizing the first set of radiopaque markers are arranged along at least four radial lines which extend from a center location, based on recognizing the radial lines are angularly spaced apart about the center location, and based on recognizing at least three of the radiopaque markers are arranged along each of the radial lines,
identify in the image locations of a second set of radiopaque markers based on recognizing the second set of radiopaque markers are arranged along a circle, wherein the first set of radiopaque markers are on an orientation plate, the second set of radiopaque markers are on a registration plate spaced apart from the orientation plate, and the orientation plate and the registration plate are attached to a base frame of a fixture mounted to the x-ray medical image device, and
register the image to a three-dimensional tracking space based on comparison of locations of the first set radiopaque markers in the image to locations of the second set radiopaque markers in the image.

2. The surgical navigation system of claim 1, wherein the operation to register the image to the three-dimensional tracking space based on comparison of locations of the first set radiopaque markers in the image to locations of the second set radiopaque markers in the image, comprises to:
determine an axis of rotation of the fixture relative to an image plane of the x-ray medical imaging device; and
rotate the locations of the first and second sets radiopaque markers about the axis to remove tilt angle between the fixture and the image plane of the x-ray medical imaging device.

3. The surgical navigation system of claim 1, wherein the operation to identify in the image the first set of radiopaque markers, comprises to:
recognize the first set of radiopaque markers are arranged along at least eight radial lines which extend from the center location and are angularly spaced apart about the center location, and where at least three of the radiopaque markers of the first set are arranged along each of radial lines.

4. The surgical navigation system of claim 1, wherein the operation to identify in the image the first set of radiopaque markers, comprises to:
recognize the first set of radiopaque markers are arranged along a plurality of concentric circles.

5. The surgical navigation system of claim 4, wherein the operation to identify in the image the first set of radiopaque markers, comprises to:
recognize the first set of radiopaque markers includes at least 24 radiopaque markers arranged along at least three concentric circles.

6. The surgical navigation system of claim 1, wherein the operation to identify in the image the second set of radiopaque markers, comprises to:
recognize the second set of radiopaque markers includes at least four radiopaque markers.

7. The surgical navigation system of claim 1, wherein the operation to identify in the image the second set of radiopaque markers, comprises to:
recognize the second set of radiopaque markers includes at least 24 radiopaque markers.

8. The surgical navigation system of claim 1, further comprising:
the registration fixture including the base frame, the orientation plate attached to the base frame, and the registration plate attached to the base frame and spaced apart from the orientation plate.

9. A registration fixture for registration of a medical image to a three-dimensional tracking space comprising:
a base frame adapted to be mounted to an x-ray medical imaging device;
an orientation plate attached to the base frame and having a first set of radiopaque markers arranged along at least four radial lines which extend from a center location, the radial lines are angularly spaced apart about the center location, and at least three of the radiopaque markers are arranged along each of the radial lines; and
a registration plate attached to the base frame and spaced apart from the orientation plate, the registration plate having a second set of radiopaque markers arranged along a circle.

10. The registration fixture of claim 9, wherein:
the first set of radiopaque markers are arranged along at least eight radial lines which extend from the center location;
the radial lines are angularly spaced apart about the center location; and
at least three of the radiopaque markers of the first set are arranged along each of radial lines.

11. The registration fixture of claim 9, wherein:
the radial lines are non-uniformly angularly spaced at least 20 degrees apart.

12. The registration fixture of claim 11, wherein:
angles between two adjacent pairs of radial lines differ by at least two degrees.

13. The registration fixture of claim 9, wherein:
the radial lines are uniformly angularly spaced at least 20 degrees apart about the center location.

14. The registration fixture of claim 9, wherein:
the first set of radiopaque markers are arranged along a plurality of concentric circles.

15. The registration fixture of claim 14, wherein:
the first set of radiopaque markers includes at least 24 radiopaque markers arranged along at least three concentric circles.

16. The registration fixture of claim 9, wherein:
the second set of radiopaque markers includes at least four radiopaque markers.

17. The registration fixture of claim 9, wherein:
the second set of radiopaque markers includes at least 24 radiopaque markers.

18. The registration fixture of claim 9, wherein:
the orientation plate and the registration plate are parallel to each other;
the first set of radiopaque markers includes at least 24 radiopaque markers arranged along at least three concentric circles; and
the second set of radiopaque markers are arranged along the circle with a center location which is aligned, in a direction normal to the orientation plate and the registration plate, with the center location of the at least three concentric circles of the at least 24 radiopaque markers of the first set.

19. The registration fixture of claim 9, wherein:
the orientation plate and the registration plate are parallel to each other;
none of the radiopaque markers of the first set are aligned with any of the radiopaque markers of the second set in a direction normal to the orientation plate and the registration plate.

20. The registration fixture of claim 9, further comprising:
a side frame adapted to detachably mount a plurality of optical tracking markers and adapted to detachably mount to the base frame.

* * * * *